(12) United States Patent
Haas et al.

(10) Patent No.: US 11,174,496 B2
(45) Date of Patent: Nov. 16, 2021

(54) GENETICALLY MODIFIED ACETOGENIC CELL

(71) Applicant: Evonik Operations GmbH, Essen (DE)

(72) Inventors: Thomas Haas, Münster (DE); Thomas Bülter, Duisburg (DE); Anja Hecker, Münster (DE)

(73) Assignee: Evonik Operations GmbH, Essen (DE)

( * ) Notice: Subject to any disclaimer, the term of this patent is extended or adjusted under 35 U.S.C. 154(b) by 4 days.

(21) Appl. No.: 16/063,256

(22) PCT Filed: Dec. 15, 2016

(86) PCT No.: PCT/EP2016/081202
§ 371 (c)(1),
(2) Date: Jun. 16, 2018

(87) PCT Pub. No.: WO2017/102952
PCT Pub. Date: Jun. 22, 2017

(65) Prior Publication Data
US 2018/0371504 A1    Dec. 27, 2018

(30) Foreign Application Priority Data
Dec. 17, 2015   (EP) ..................... 15200673

(51) Int. Cl.
| | |
|---|---|
| C12P 7/04 | (2006.01) |
| C12N 9/04 | (2006.01) |
| C12N 9/10 | (2006.01) |
| C12P 7/16 | (2006.01) |
| C12N 1/20 | (2006.01) |
| C12R 1/02 | (2006.01) |
| C12R 1/145 | (2006.01) |

(52) U.S. Cl.
CPC .............. *C12P 7/04* (2013.01); *C12N 1/205* (2021.05); *C12N 9/0006* (2013.01); *C12N 9/10* (2013.01); *C12P 7/16* (2013.01); *C12R 2001/02* (2021.05); *C12R 2001/145* (2021.05); *C12Y 101/01001* (2013.01); *C12Y 101/01157* (2013.01); *C12Y 101/01178* (2013.01); *C12Y 102/0101* (2013.01); *C12Y 105/05001* (2013.01); *C12Y 203/01009* (2013.01); *C12Y 207/02001* (2013.01); *Y02E 50/10* (2013.01)

(58) Field of Classification Search
CPC .... C12P 7/16; C12P 7/00; C12P 7/649; C12N 1/20; C12N 9/10; C12Y 101/01001; C12Y 203/01009; C12Y 101/01157; C12Y 102/0105
USPC .......... 435/252.3, 252.7, 160, 155, 189, 170
See application file for complete search history.

(56) References Cited

U.S. PATENT DOCUMENTS

| | | |
|---|---|---|
| 3,992,268 A | 11/1976 | Antos |
| 4,540,772 A | 9/1985 | Pipper et al. |
| 5,604,127 A | 2/1997 | Nisbet et al. |
| 5,723,603 A | 3/1998 | Gilbert et al. |
| 5,807,722 A | 9/1998 | Gaddy |
| 6,492,541 B2 | 12/2002 | Drauz et al. |
| 7,196,218 B2 | 3/2007 | Gaddy et al. |
| 7,241,908 B2 | 7/2007 | Haas et al. |
| 7,364,718 B2 | 4/2008 | Haas et al. |
| 7,368,600 B2 | 5/2008 | Hateley et al. |
| 8,241,881 B2 | 8/2012 | Bradin |
| 8,535,921 B2 | 9/2013 | Kohn et al. |
| 8,703,451 B2 | 4/2014 | Haas et al. |
| 8,809,576 B2 | 8/2014 | Schraven et al. |
| 8,835,691 B2 | 9/2014 | Klasovsky et al. |
| 8,999,684 B2 | 4/2015 | Poetter et al. |
| 9,012,227 B2 | 4/2015 | Karau et al. |
| 9,068,202 B2 | 6/2015 | Tran et al. |
| 9,102,958 B2 | 8/2015 | Botes et al. |
| 9,150,890 B2 | 10/2015 | Poetter et al. |
| 9,200,043 B2 | 12/2015 | Poetter et al. |
| 9,249,435 B2 | 2/2016 | Gielen et al. |
| 9,562,930 B2 | 2/2017 | Makuth et al. |
| 9,580,732 B2 | 2/2017 | Poetter et al. |
| 9,587,231 B2 | 3/2017 | Hom et al. |
| 9,677,045 B2 | 6/2017 | Pharkya et al. |
| 9,719,117 B2 | 8/2017 | Schaffer et al. |
| 9,765,366 B2 | 9/2017 | Schiemann et al. |

(Continued)

FOREIGN PATENT DOCUMENTS

| | | |
|---|---|---|
| CA | 2 900 293 | 8/2014 |
| EP | 2 292 783 | 3/2011 |

(Continued)

OTHER PUBLICATIONS

Devos et al., (Proteins: Structure, Function and Genetics, 2000, vol. 41: 98-107.*

(Continued)

*Primary Examiner* — Tekchand Saidha
*Assistant Examiner* — Mohammad Y Meah
(74) *Attorney, Agent, or Firm* — Law Office of: Michael A. Sanzo, LLC

(57) ABSTRACT

There is provided an acetogenic microbial cell which is capable of producing at least one higher alcohol from a carbon source, wherein the acetogenic microbial cell is genetically modified to comprise an increased expression relative to its wild type cell of at least one enzyme, $E_8$, a butyryl-CoA:acetate CoA transferase (cat3). There is also provided a method and use of the cell to produce higher alcohols.

16 Claims, 1 Drawing Sheet
Specification includes a Sequence Listing.

(56) References Cited

U.S. PATENT DOCUMENTS

| | | |
|---|---|---|
| 9,765,370 B2 | 9/2017 | Hennemann |
| 9,885,060 B2 | 2/2018 | Dennig et al. |
| 9,920,334 B2 | 3/2018 | Haas et al. |
| 10,053,713 B2 | 8/2018 | Pfeffer et al. |
| 10,329,590 B2 | 6/2019 | Haas |
| 2007/0092957 A1 | 4/2007 | Donaldson et al. |
| 2007/0275447 A1 | 11/2007 | Lewis et al. |
| 2008/0057554 A1 | 3/2008 | Huhnke et al. |
| 2010/0137641 A1 | 6/2010 | Iida et al. |
| 2010/0324257 A1 | 12/2010 | Karau et al. |
| 2011/0111475 A1 | 5/2011 | Kuhry et al. |
| 2011/0118433 A1 | 5/2011 | Poetter et al. |
| 2011/0171702 A1 | 7/2011 | Reinecke et al. |
| 2012/0034665 A1 | 2/2012 | Haas et al. |
| 2012/0045807 A1 | 2/2012 | Simpson et al. |
| 2013/0189750 A1 | 7/2013 | Jin et al. |
| 2013/0203953 A1 | 8/2013 | Pereira et al. |
| 2014/0011249 A1 | 1/2014 | Burgard et al. |
| 2014/0051136 A1 | 2/2014 | Liao et al. |
| 2014/0120587 A1 | 5/2014 | Haas et al. |
| 2014/0178948 A1 | 6/2014 | Schaffer et al. |
| 2014/0186905 A1 | 7/2014 | Schaffer et al. |
| 2014/0256904 A1 | 9/2014 | Schaffer et al. |
| 2014/0273123 A1 | 9/2014 | Tobey et al. |
| 2014/0308717 A1 | 10/2014 | Haas et al. |
| 2015/0010968 A1 | 1/2015 | Engel et al. |
| 2015/0044744 A1 | 2/2015 | Pfeffer et al. |
| 2015/0093798 A1 | 4/2015 | Jung et al. |
| 2015/0099282 A1 | 4/2015 | Haas et al. |
| 2015/0111253 A1 | 4/2015 | Schaffer et al. |
| 2015/0111254 A1 | 4/2015 | Hennemann et al. |
| 2015/0125912 A1 | 5/2015 | Haas et al. |
| 2015/0218600 A1 | 8/2015 | Haas et al. |
| 2015/0267231 A1 | 9/2015 | Haas et al. |
| 2015/0275245 A1 | 10/2015 | Haas et al. |
| 2015/0284747 A1 | 10/2015 | Schiemann et al. |
| 2015/0299741 A1 | 10/2015 | Engel et al. |
| 2015/0353963 A1 | 12/2015 | Haas et al. |
| 2016/0137969 A1 | 5/2016 | Haas et al. |
| 2016/0138058 A1 | 5/2016 | Wittmann et al. |
| 2016/0138061 A1 | 5/2016 | Haas et al. |
| 2016/0177259 A1 | 6/2016 | Haas et al. |
| 2016/0215302 A1 | 7/2016 | Haas et al. |
| 2016/0215304 A1 | 7/2016 | Haas et al. |
| 2016/0244790 A1 | 8/2016 | Haas et al. |
| 2016/0272950 A1 | 9/2016 | Corthals et al. |
| 2016/0326549 A1 | 11/2016 | Dennig et al. |
| 2016/0326555 A1 | 11/2016 | Engel et al. |
| 2017/0130248 A1 | 5/2017 | Reinecke |
| 2017/0145448 A1 | 5/2017 | Schaffer et al. |
| 2017/0183694 A1 | 6/2017 | Pharkya et al. |
| 2017/0204437 A1 | 7/2017 | Haas et al. |
| 2017/0260552 A1 | 9/2017 | Haas et al. |
| 2017/0260553 A1 | 9/2017 | Haas et al. |
| 2018/0127791 A1 | 5/2018 | Schaffer |
| 2018/0135085 A1 | 5/2018 | Haas |
| 2018/0142266 A1 | 5/2018 | Haas et al. |
| 2018/0155743 A1 | 6/2018 | Haas et al. |
| 2018/0208947 A1 | 7/2018 | Haas et al. |
| 2019/0127321 A1 | 5/2019 | Haas |
| 2019/0127769 A1 | 5/2019 | Haas |
| 2019/0169654 A1 | 6/2019 | Hecker |
| 2019/0264245 A1 | 8/2019 | Haas et al. |
| 2020/0231994 A1 | 7/2020 | Haas et al. |

FOREIGN PATENT DOCUMENTS

| | | |
|---|---|---|
| GB | 1009370 | 11/1965 |
| GB | 1113357 | 5/1968 |
| GB | 1563933 | 4/1980 |
| WO | WO 98/00558 | 1/1998 |
| WO | WO 00/14052 | 3/2000 |
| WO | WO 00/20566 | 4/2000 |
| WO | WO 00/68407 | 11/2000 |
| WO | WO 2007/136762 | 11/2007 |
| WO | WO 2008/119082 | 10/2008 |
| WO | WO 2008/148640 | 12/2008 |
| WO | WO 2009/078973 | 6/2009 |
| WO | WO 2009/100434 | 8/2009 |
| WO | WO 2010/115054 | 10/2010 |
| WO | WO 2010/118410 | 10/2010 |
| WO | WO 2012/091479 | 7/2012 |
| WO | WO 2012/099603 | 7/2012 |
| WO | WO 2012/177943 | 12/2012 |
| WO | WO 2014/140336 | 9/2014 |
| WO | WO 2015/110518 | 7/2015 |
| WO | WO 2015/172972 | 11/2015 |
| WO | WO 2015/173059 | 11/2015 |
| WO | WO 2016/008979 | 1/2016 |
| WO | WO 2016/131801 | 8/2016 |
| WO | WO 2016/184656 | 11/2016 |
| WO | WO 2016/184663 | 11/2016 |
| WO | WO 2017/001170 | 1/2017 |
| WO | WO 2017/202975 | 11/2017 |
| WO | WO 2018/018402 | 2/2018 |
| WO | WO 2018/019245 | 2/2018 |
| WO | WO 2018/019841 | 2/2018 |
| WO | WO 2018/019847 | 2/2018 |
| WO | WO 2018/019867 | 2/2018 |
| WO | WO 2018/115333 | 6/2018 |
| WO | WO 2018/115350 | 6/2018 |

OTHER PUBLICATIONS

Witkowski et al., (Biochemistry 38:11643-11650, 1999.*
Kisselev L., (Structure, 2002, vol. 10: 8-9.*
Whisstock et al., (Quarterly Reviews of Biophysics 2003, vol. 36 (3): 307-340.*
Bengelelsdrop et al. (FEBS letters 2012, 586, pp. 2191-2198).*
Peter Durre ( FEMS letters 2016, pp. 1-7.*
Wiechmann et al. Handbook of hydrocarbon, and lipid microbial 2017 p. 1-32.*
European Search Report and Opinion for EP 15 20 0673 (European counterpart of U.S. Appl. No. 16/063,256), completed Mar. 8, 2016.
International Search Report for PCT/EP2017/062642 (international counterpart of copending U.S. Appl. No. 16/304,660), filed May 24, 2017.
Written Opinion of the International Searching Authority for PCT/EP2017/062642 (international counterpart of copending U.S. Appl. No. 16/304,660), filed May 24, 2017.
International Preliminary Report on Patentability for PCT/EP2017/062642 (international counterpart of copending U.S. Appl. No. 16/304,660), filed May 24, 2017.
European Search Report and Opinion for EP 16 17 1624 (European counterpart of copending U.S. Appl. No. 16/304,660), filed May 27, 2016.
International Search Report for PCT/EP2017/068841 (international counterpart of copending U.S. Appl. No. 16/320,097), filed Jul. 26, 2017.
Written Opinion of the International Searching Authority for PCT/EP2017/068841 (international counterpart of copending U.S. Appl. No. 16/320,097), filed Jul. 26, 2017.
International Preliminary Report on Patentability for PCT/EP2017/068841 (international counterpart of copending U.S. Appl. No. 16/320,097), filed Jul. 26, 2017.
European Search Report and Opinion for EP 16 18 1431 (European counterpart of copending U.S. Appl. No. 16/320,097), filed Jul. 27, 2016.
Restriction Requirement for copending U.S. Appl. No. 15/326,546, dated Jul. 28, 2017.
Response to Restriction Requirement for copending U.S. Appl. No. 15/326,546, filed Sep. 26, 2017.
Office Action for copending U.S. Appl. No. 15/326,546, dated Mar. 14, 2018.
Response to Office Action for copending U.S. Appl. No. 15/326,546, filed Jul. 7, 2018.
Final Office Action for copending U.S. Appl. No. 15/326,546, dated Oct. 23, 2018.

(56) References Cited

OTHER PUBLICATIONS

Response to Final Office Action for copending U.S. Appl. No. 15/326,546, filed Jan. 22, 2019.
Advisory Action for copending U.S. Appl. No. 15/326,546, dated Feb. 5, 2019.
Amendment, Response and RCE for copending U.S. Appl. No. 15/326,546, filed Mar. 10, 2019.
Ato, et al., "Enrichment of amino acid-oxidizing acetate-reducing bacteria," *Journal of Bioscience and Bioengineering* 118(2): 160-165 (2014).
Born, et al., "Enzyme-Catalyzed Acylation of Homoserine: Mechanistic Characterization of the *Haemophilus influenzae met2*-Encoded Homoserine Transacetylase," *Biochemistry* 39(29):8556-8564 (Jul. 2000).
Drake and Küsel, "Acetogenic clostridia," In: Dürre, P. (ed.), Handbook on Clostridia, pp. 719-746; CRC Press, Boca Raton, Florida (2005).
Drake, et al., "Acetogenic Prokaryotes," *Prokaryotes* 2:354-420 Chapter 1.13 (2006).
Galaction, et al., "Direct Extraction of Propionic Acid from *Propionibacterium acidipropionici* Broths with Tri-n-octylamine," *Chem. Eng. Technol.* 35(9): 1657-1663 (2012).
Kandasamy, et al., "Engineering *Escherichia coli* with acrylate pathway genes for propionic acid synthesis and its impact on mixed-acid fermentation," *Appl. Microbiol. Biotechnol.* 971191-1200 (2013).
Keshav, et al., "Recovery of propionic acid from an aqueous stream by reactive extraction: effect of diluents," *Desalanation* 244 (1-3): 12-23 (2009).
Koch, "Growth Measurement" Methods for General and Molecular Biology; Chapter 11; Gerhardt (ed); pp. 248-277 (2004).
Müller, et al., "Molecular and Cellular Biology of Acetogenic Bacteria," From: Strict and Facultative Anaerobes: Medical and Environmental Aspects; Chapter 14; pp. 251-281 (2004).
Stowers, et al., "Development of an industrializable fermentation process for propionic acid production," *J. Ind. Microbiol. Biotechnol.* 41:837-852 (2014).
Tholozan, et al., "*Clostridium neopropionicum* sp. nov., a strict anaerobic bacterium fermenting ethanol to propionate through acrylate pathway," *Arch. Microbiol.* 157:249-257 (1992).
Willke, "Methionine production—a critical review," *Appl. Microbiol. Biotechnol.* 98(24):9893-9914 (Nov. 2014).
Zhang, et al., "$_D$-Lactic acid biosynthesis from biomass-derived sugars via *Lactobacillus delbrueckii* fermentation," *Bioprocess Biosyst Eng* 36:1897-1904 (2013).
U.S. Appl. No. 16/304,660, filed Nov. 26, 2018, Haas.
U.S. Appl. No. 16/320,097, filed Jan. 24, 2019, Haas.
International Search Report for PCT/EP2016/081202 (international counterpart of U.S. Appl. No. 16/063,256), filed Dec. 15, 2016.
Written Opinion of the International Searching Authority for PCT/EP2016/081202 (international counterpart of U.S. Appl. No. 16/063,256), filed Dec. 15, 2016.
International Preliminary Report on Patentability for PCT/EP2016/081202 (international counterpart of U.S. Appl. No. 16/063,256), filed Dec. 15, 2016.
International Search Report for PCT/EP2015/066174 (international counterpart of copending U.S. Appl. No. 15/326,546), filed Jul. 15, 2015.
Written Opinion of the International Searching Authority for PCT/EP2015/066174 (international counterpart of copending U.S. Appl. No. 15/326,546), filed Jul. 15, 2015.
International Preliminary Report on Patentability for PCT/EP2015/066174 (international counterpart of copending U.S. Appl. No. 15/326,546), filed Jul. 15, 2015.
European Search Report for EP 14 17 7492 (European counterpart of copending U.S. Appl. No. 15/326,546), filed Jul. 17, 2014.
European Search Opinion for EP 14 17 7492 (European counterpart of copending U.S. Appl. No. 15/326,546), filed Jul. 17, 2014.
International Search Report for PCT/EP2015/066275 (international counterpart of copending U.S. Appl. No. 15/326,552), filed Jul. 16, 2015.
Written Opinion of the International Searching Authority for PCT/EP2015/066275 (international counterpart of copending U.S. Appl. No. 15/326,552), filed Jul. 16, 2015.
International Preliminary Report on Patentability for PCT/EP2015/066275 (international counterpart of copending U.S. Appl. No. 15/326,552), filed Jul. 16, 2015.
European Search Report and Opinion for EP 14 17 7491 (European counterpart of copending U.S. Appl. No. 15/326,552), filed Jul. 17, 2015.
U.S. Appl. No. 15/309,951, filed Nov. 9, 2016, 2017-0260552 A1, Sep. 14, 2017, Haas.
U.S. Appl. No. 15/309,994, filed Nov. 9, 2016, 2017-0260553 A1, Sep. 14, 2017, Haas
U.S. Appl. No. 15/326,546, filed Jan. 16, 2017, 2017-0204437 A1, Jul. 20, 2017, Haas.
U.S. Appl. No. 15/326,552, filed Jan. 16, 2017, Haas.
Non Final Office Action for copending U.S. Appl. No. 15/326,546, dated Jun. 19, 2019.
Adrio, et al., "Recombinant organisms for production of industrial products," *Bioengineered Bugs* 1(2):116-131 (Mar./Apr. 2010).
Balabanova, et al., "Genetically modified proteins: functional improvement and chimeragenesis," *Bioengineered* 6(5):262-274 (Sep./Oct. 2015).
Tamano, "Enhancing microbial metabolite and enzyme production: current strategies and challenges," *Frontiers in Microbiology* 5(718): 1-6 (Dec. 2014).
U.S. Appl. No. 15/565,451, filed Oct. 10, 2017, US-2018/0127791 A1, May 10, 2018, Schaffer.
U.S. Appl. No. 15/574,334, filed Nov. 15, 2017, US-2018/0135085 A1, May 17, 2018, Haas.
U.S. Appl. No. 16/094,334, filed Oct. 17, 2018, US-2019/0127769 A1, May 17, 2019, Haas.
U.S. Appl. No. 16/095,517, filed Oct. 22, 2018, US-2019/0127321 A1, May 17, 2019, Haas.
U.S. Appl. No. 14/367,610, filed Dec. 14, 2012, US-2015/0275245 A1 Oct. 1, 2015, Haas.
U.S. Appl. No. 14/400,379, filed May 8, 2013, US-2015/0125912 A1, May 7, 2015, Haas.
U.S. Appl. No. 14/405,050, filed Jun. 14, 2013, US-2015/0267231 A1, Sep. 24, 2015, Haas.
U.S. Appl. No. 14/435,339, filed Nov. 6, 2013, US-2015/0299741 A1, Oct. 22, 2015, Engel.
U.S. Appl. No. 14/763,378, filed Jan. 10, 2014, US-2015/0353963 A1, Dec. 10, 2015, Haas.
U.S. Appl. No. 14/898,417, filed May 30, 2014, US-2016/0138058 A1, May 19, 2016, Wittmann.
U.S. Appl. No. 14/898,679, filed Jun. 17, 2014, US-2016/0137969 A1, May 19, 2016, Haas.
U.S. Appl. No. 14/969,891, filed Dec. 15, 2015, US-2016/0177259 A1, Jun. 23, 2016, Haas.
U.S. Appl. No. 15/009,425, filed Jan. 28, 2016, US-2016/0215302 A1, Jul. 28, 2016, Haas.
U.S. Appl. No. 15/359,932, filed Nov. 23, 2017, US-2017/0145448 A1, May 25, 2017, Schaffer.
U.S. Appl. No. 16/320,836, filed Jul. 25, 2017, US-2019/0169654 A1, Jun. 6, 2019 Hecker.
Restriction Requirement for copending U.S. Appl. No. 16/304,660, dated Jun. 8. 2020.
Response to Restriction Requirement for copending U.S. Appl. No. 16/304,660, filed Aug. 9, 2020.
Restriction Requirement for copending U.S. Appl. No. 16/320,097, dated Jul. 17, 2020.
Non Final Office Action for copending U.S. Appl. No. 16/304,660, dated Sep. 9, 2020.
Response to Restriction Requirement for copending U.S. Appl. No. 16/320,097, filed Sep. 17, 2020.
Non Final Office Action for copending U.S. Appl. No. 16/320,097, dated Oct. 13, 2020.

(56) References Cited

OTHER PUBLICATIONS

Kizer, et al., "Application of Functional Genomics to Pathway Optimization for Increases Isoprenoid Production," *Applied and Environmental Microbiology* 74(10):3229-3241 (May 2008).
Prather, et al., "De novo biosynthetic pathways: rational design of microbial chemical factories," *Current Opinion in Biotechnology* 19:468-474 (2008).
Non Final Office Action for copending U.S. Appl. No. 16/304,660, dated Feb. 4, 2021.
Amendment & Response to Non Final Office Action for copending U.S. Appl. No. 16/320,097, filed Feb. 16, 2021.
Abrini, et al., "*Clostridium autoethanogenum*, sp. nov., an anaerobic bacterium that produces ethanol from carbon monoxide," *Arch Microbiol* 161(4):345-351 (Apr. 1994).
Andreesen, et al., "Fermentation of Glucose, Fructose, and Xylose by *Clostridium thermoaceticum*: Effect of Metals on Growth Yield, Enzymes, and the Synthesis of Acetate from $CO_2$," *Journal of Bacteriology* 114(2):743-751 (May 1973).
Baba, et al., "Construction of *Escherichia coli* K-12 in-frame, single gene knockout mutants: the Keio collection," *Molecular Systems Biology* 21:1-11 (Feb. 2006).
Becker, et al., "A generic system for the *Escherichia coli* cell-surface display of lipolytic enzymes," *FEBS Letters* 575(5): 1177-1182 (Feb. 2005).
Bornstein, et al., "The energy metabolism of *Clostridium Kluyveri* and the synthesis of fatty acids," *J Biol Chem* 172(2):659-669 (Feb. 1948).
Byoung, et al., "*In situ* extractive fermentation for the production of hexanoic acid from galactitol by *Clostridium* sp. BS-1," *Enzyme and Microbial Technology* 53(3)143-151 (Aug. 2013).
Cotter, et al., "Ethanol and acetate production by *Clostridium Ijungadahlii* and *Clostridium autoethanogenum* using resting cells," *Bioprocess Biosyst Eng* 32(3):369-380 (Apr. 2009).
Dar, et al., "Competition and coexistence of sulfate-reducing bacteria, acetogens and methanogens in a lab-scale anaerobic bioreactor as affected by changing substrate to sulfate ratio," *Appl Microbiol Biotechnol* 78(6):1045-1055 (Feb. 2008).
De Lorenzo, et al., "Mini-Tn5 Transposon Derivatives for Insertion Mutagenesis, Promoter Probing, and Chromosomal Insertion of Cloned DNA in Gram-Negative Eubacteria," *Journal of Bacteriology* 172(11):6568-6572 (Nov. 1990).
Demler, et al., "Reaction Engineering Analysis of Hydrogenotrophic Production of Acetic Acid by *Acetobacterium woodii*," *Biotechnology and Bioengineering* 108(2):470-474 (Feb. 2011).
Ding, et al., "Caproate formation in mixed-culture fermentative hydrogen production," *Bioresource Technology* 101(24):9550-9559 (Dec. 2010).
Kaulmann, et al., "Substrate spectrum of ω-transaminase from *Chromobacteria violaceum* DSM30191 and its potential for biocatalysis," *Enzyme and Microbial Technology* 41(5):628-637 (Oct. 2007).
Kenealy, et al., "Studies on the substrate range of *Clostridium kluyveri*; the use of propanol and succinate," *Arch Microbiol* 141(3):187-194 (Apr. 1985).
Kieun, et al., "*In situ* Biphasic Extractive Fermentation for Hexanoic Acid Production from Sucrose by *Megasphaera elsdenii* NCIMB 702410," *Appl Biochem Biotechnol* 171(5):1094-1107 (Nov. 2013).
Kojima, et al., "Purification and Characterization of the Lipase from *Pseudomonas fluorescens* HU380," *Journal of Bioscience and Bioengineering* 96(3):219-226 (accepted May 2003).
Levy, et al., "Biorefining of biomass to liquid fuels and organic chemicals," *Enzyme and Microbial Technology* 3(3):207-215 (Jul. 1981).
Levy, et al., "Kolbe Electrolysis of Mixtures of Aliphatic Organic Acids," *Journal of the Electrochemical Society* 131(4):773-777 (Apr. 1984).
Mieke, et al., "Bioelectrochemical Production of Caproate and Caprylate from Acetate by Mixed Cultures," *ACS Sustainable Chem Eng* 1(5):513-518 (May 2013).
Li, a dissertation, "Production of Acetic Acid from Synthesis Gas with Mixed Acetogenic Microorganisms," Texas A & M University, Chemical Engineering (May 2002).
Morinaga, et al., "The production of acetic acid from carbon dioxide and hydrogen by an anaerobic bacterium," *Journal of Biotechnology* 14(2):187-194 (May 1990).
Overkamp, et al., "Cloning and characterization of eight cytochrome P450 cDNAs from chickpea (*Cicer arietnum* L.) cell suspension cultures," *Plant Science* 155(1):101-108 (Jun. 2000).
Panke, et al., "Engineering of a Stable Whole-Cell Biocatalyst Capable of (S)-Styrene Oxide Formation for Continuous Two-Liquid-Phase Applications," *Applied and Environmental Microbiology* 65(12):5619-5623 (Dec. 1999).
Riesenberg, et al., "High cell density fermentation of recombinant *Escherichia coli* expressing human interferon alpha 1," *Appl Microbiol Biotechnol* 34(1):77-82 (accepted Jun. 1990).
Sakai, et al., "Ethanol production from $H_2$ and $CO_2$ by a newly isolated thermophilic bacterium, *Moorella* sp. HUC22-1," *Biotechnology Letters* 26(20):1607-1612 (Oct. 2004).
Saxena, et al., "Effect of trace metals on ehtanol production from synthesis gas by the ethanologenic acetogen, *Clostridium ragsdalei*," *J Ind Microbiol Biotechnol* 38(4):513-521 (accepted Jul. 2010).
Scheps, et al., "Regioselective ω-hydroxylation of medium-chain n-alkanes and primary alcohols by CYP153 enzymes from *Mycobacterium marinum* and *Polaromonas* sp. strain JS666," *Organic & Biomolecular Chemistry* 9:6727-6733 (Oct. 2011).
Schmidt, et al., "Production of Acetic Acid from Hydrogen and Carbon Dioxide by *Clostridium* Species ATCC 29797," *Chem Eng Commun* 45(1-6):61-73 (May 1986).
Seedorf, et al., "The genome of *Clostridium Kluyveri*, a strict anaerobe with unique metabolic features," *Proc Natl Acad Sci USA* 105(6) :2128-2133 (Feb. 2008).
Seedorf, et al., "*Clostridium kluyveri* DSM 555 complete genome," retrieved from GenBank, database accession No. CP0000673, (Jan. 2014).
Sim, et al., "Optimization of acetic acid production from systhesis gas by chemolithotrophic bacterium—*Clostridium aceticum* using statistical approach," *Bioresource Technology* 99(8):2724-2735 (May 2008).
Smits, et al., "Functional Analysis of Alkane Hydroxylases from Gram-Negative and Gram-Positive Bacteria," *Journal of Bacteriology* 184(6):1773 3-1742 (Mar. 2002).
Stadtman, et al., "Fatty Acid Synthesis by Enzyme Preparations of *Clostridium kluyveri*," *J Biol Chem* 184(2)069-794 (Jun. 1950).
Stadtman, et al., "Tracer Experiments on the Mechanism of Synthesis of Valeric and Caproic Acids by *Clostridium kluyveri*," *J Biol Chem* 178(2):677-682 (Jun. 1948).
Steinbusch, et al., "Biological formation of caproate and caprylate from acetate: fuel and chemical production from low grade biomass," *Energy and Environmental Science* 4:216-224 (accepted Oct. 2010).
Van Beilen, et al., "Diversity of Alkane Hydroxylase Systems in the Environment," *Oil & Gas Science and Technology* 58(4):427-440 (2003).
Vaysse, et al., "Chain-length selectivity of various lipases during hydrolysis, esterification and alcoholysis in biphasic aqueous medium," *Enzyme and Microbial Technology* 31(5):648-655 (Oct. 2002).
Vega, et al., "Study of Gaseous Substrate Fermentations: Carbon Monoxide Conversion to Acette. 1. Batch Culture," *Biotechnology and Bioengineering* 34(6):774-784 (Sep. 1989).
Wadhawan, et al., "Biphasic sonselectrosynthesis. A review," *Pure Appl Chem* 73(12):1947-1955 (Apr. 2001).
Wood, et al., "Life with CO or $CO_2$ and $H_2$ as a source of carbon energy," *FASEB J* 5(2): 156-163 (Feb. 1991).
Wu, et al., "Microbial composition and characterization of prevalent methanogens and acetogens isolated from syntrophic methanogenic granules," *Appl Microbiol Biotechnol* 38(2):282-290 (Nov. 1992).
Younesi, et al., "Ethanol and acetate production from synthesis gas via fermentation processes using anaerobic bacterium, *Clostridium ijungadahlii*," *Biochemical Engineering Journal* 27(2):110-119 (Dec. 2005).

(56) References Cited

OTHER PUBLICATIONS

Zhang, et al., "Fatty acids production from hydrogen and carbon dioxide by mixed culture in the biofilm reactor," *Water Research* 47(16):6122-6129 (available online Jul. 2013).

Anderlund, et al., "Expression of the *Escherichia coli pntA* and *pntB* Genes, Encoding Nicotinamide Nucleotide Transhydrogenase, in *Saccharomyces cerevisiae* and Its Effect on Product Formation during Anaerobic Glucose Fermentation," *Appl. Environ. Microbiol.* 65(6):2333-2340 (Jun. 1999).

Devos, et al., "Practical Limits of Function Prediction," *Proteins; Structure, Function and Genetics* 41:98-107 (2000).

Fukaya, et al., "The *aarC* Gene Responsible for Acetic Acid Assimilation Confers Acetic Acid Resistance on *Acetobacter aceti*," *Journal of Fermentation and Bioengineering* 76(4):270-275 (Jan. 1993).

Hatefi, et al., "Dehydrogenase and transhydrogenase properties of the soluble NADH dehydrogenase of bovine heart mitochondria," *Proc. Natl. Acad. Sci. USA* 74(3):846-850 (Mar. 1977).

Kisselev, "Polypeptide Release Factors in Prokaryotes and Eukaryotes: Same Function, Different Structure," *Structure* 10:8-9 (Jan. 2002).

Mullins, et al., "A Specialized Citric Acid Cycle Requiring Succinyl-Coenzyme A (CoA):Acetate CoA-Transferase (AarC) Confers Acetic Acid Resistance on the Acidophile *Acetobacter aceti*," *Journal of Bacteriology* 190(14):4933-4940 (Jul. 2008).

Perez, et al., "Biocatalytic Reduction of Short-Chain Carboxylic Acids Into Their Corresponding Alcohols With Syngas Fermentation," *Biotechnology and Bioengineering* 110(4):1066-1077 (Apr. 2013).

Stadtman, et al., "Discussion," *Federation Proceedings* 12(3):692-693 (Sep. 1953).

Stadtman, "The Coenzyme A Transphorase System in *Clostridium kluyveri*," *J. Biol. Chem.* 203(71):501-512 (Jul. 1953).

Whisstock, et al., "Prediction of protein function from protein sequence and structure," *Quarterly Reviews of Biophysics* 36(3):307-340 (Aug. 2003).

Witkowski, et al., "Conversion of a β-Ketoacyl Synthase to a Malonyl Decarboxylase by Replacement of the Active-Site Cysteine with Glutamine," *Biochemisty* 38(36):11643-11650 (Sep. 1999).

Amendment & Response to Office Action for copending U.S. Appl. No. 16/304,660, filed May 13, 2021.

Final Office Action for copending U.S. Appl. No. 16/304,660, dated May 21, 2021.

Notice of Allowance for copending U.S. Appl. No. 16/320,097, dated May 13, 2021.

Supplemental Notice of Allowance for copending U.S. Appl. No. 16/320,097, dated May 26, 2021.

\* cited by examiner

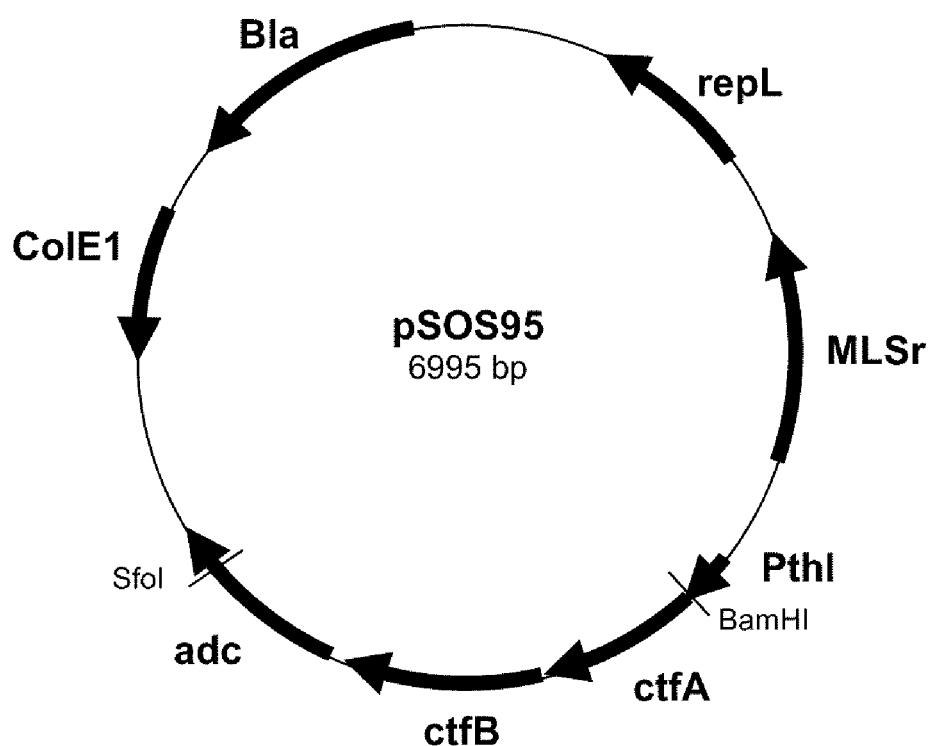

SEQUENCE LISTING

<160> NUMBER OF SEQ ID NOS: 60

<210> SEQ ID NO 1
<211> LENGTH: 437
<212> TYPE: PRT
<213> ORGANISM: Clostridium kluyveri

<400> SEQUENCE: 1

Met Val Phe Lys Asn Trp Gln Asp Leu Tyr Lys Ser Lys Ile Val Ser
1               5                   10                  15

Ala Asp Glu Ala Val Ser Lys Val Ser Cys Gly Asp Ser Ile Ile Leu
            20                  25                  30

Gly Asn Ala Cys Gly Ala Ser Leu Thr Leu Leu Asp Ala Leu Ala Ala
        35                  40                  45

Asn Lys Glu Lys Tyr Lys Ser Val Lys Ile His Asn Leu Ile Leu Asn
    50                  55                  60

Tyr Lys Asn Asp Ile Tyr Thr Asp Pro Glu Ser Glu Lys Tyr Ile His
65                  70                  75                  80

Gly Asn Thr Phe Phe Val Ser Gly Thr Lys Glu Ala Val Asn Cys
                85                  90                  95

Asn Arg Thr Asp Tyr Thr Pro Cys Phe Phe Tyr Glu Ile Pro Lys Leu
            100                 105                 110

Leu Lys Gln Lys Tyr Ile Asn Ala Asp Val Ala Phe Ile Gln Val Ser
            115                 120                 125

Lys Pro Asp Ser His Gly Tyr Cys Ser Phe Gly Val Ser Thr Asp Tyr
130                 135                 140

Ser Gln Ala Met Val Gln Ser Ala Lys Leu Ile Ile Ala Glu Val Asn
145                 150                 155                 160

Asp Gln Met Pro Arg Val Leu Gly Asp Asn Phe Ile His Ile Ser Asp
            165                 170                 175

Met Asp Tyr Ile Val Glu Ser Ser Arg Pro Ile Leu Glu Leu Thr Pro
            180                 185                 190

Pro Lys Ile Gly Glu Val Glu Lys Thr Ile Gly Lys Tyr Cys Ala Ser
            195                 200                 205

Leu Val Glu Asp Gly Ser Thr Leu Gln Leu Gly Ile Gly Ala Ile Pro
210                 215                 220

Asp Ala Val Leu Leu Phe Leu Lys Asp Lys Lys Asp Leu Gly Ile His
225                 230                 235                 240

Ser Glu Met Ile Ser Asp Gly Val Val Glu Leu Val Glu Ala Gly Val
            245                 250                 255

Ile Thr Asn Lys Lys Lys Ser Leu His Pro Gly Lys Ile Ile Ile Thr
            260                 265                 270

Phe Leu Met Gly Thr Lys Lys Leu Tyr Asp Phe Ile Asn Asp Asn Pro
            275                 280                 285

Met Val Glu Gly Tyr Pro Val Asp Tyr Val Asn Asp Pro Lys Val Ile
            290                 295                 300

Met Gln Asn Ser Lys Met Val Cys Ile Asn Ser Cys Val Glu Val Asp
305                 310                 315                 320

Phe Thr Gly Gln Val Cys Ala Glu Ser Val Gly Phe Lys Gln Ile Ser
            325                 330                 335

Gly Val Gly Gly Gln Val Asp Tyr Met Arg Gly Ala Ser Met Ala Asp
            340                 345                 350

Gly Gly Lys Ser Ile Leu Ala Ile Pro Ser Thr Ala Ala Gly Gly Lys
            355                 360                 365

```
Ile Ser Arg Ile Val Pro Ile Leu Thr Glu Gly Ala Gly Val Thr Thr
    370                 375                 380

Ser Arg Tyr Asp Val Gln Tyr Val Val Thr Glu Tyr Gly Ile Ala Leu
385                 390                 395                 400

Leu Lys Gly Lys Ser Ile Arg Glu Arg Ala Lys Glu Leu Ile Lys Ile
                405                 410                 415

Ala His Pro Lys Phe Arg Glu Glu Leu Thr Ala Gln Phe Glu Lys Arg
            420                 425                 430

Phe Ser Cys Lys Leu
            435

<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
                20                  25                  30

Ala Ile Lys Glu Ala Val Lys Lys Ala Gly Ile Lys Pro Glu Asp Val
            35                  40                  45

Asn Glu Val Ile Leu Gly Asn Val Leu Gln Ala Gly Leu Gly Gln Asn
        50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
290                 295                 300
```

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
            325                 330                 335

Val Asn Val Asn Gly Gly Ala Ile Ala Leu Gly His Pro Ile Gly Ala
        340                 345                 350

Ser Gly Ala Arg Ile Leu Val Thr Leu Val His Ala Met Gln Lys Arg
    355                 360                 365

Asp Ala Lys Lys Gly Leu Ala Thr Leu Cys Ile Gly Gly Gln Gly
370                 375                 380

Thr Ala Ile Leu Leu Glu Lys Cys
385                 390

<210> SEQ ID NO 3
<211> LENGTH: 282
<212> TYPE: PRT
<213> ORGANISM: Clostridium kluyveri

<400> SEQUENCE: 3

Met Ser Ile Lys Ser Val Ala Val Leu Gly Ser Gly Thr Met Ser Arg
1               5                   10                  15

Gly Ile Val Gln Ala Phe Ala Glu Ala Gly Ile Asp Val Ile Ile Arg
            20                  25                  30

Gly Arg Thr Glu Gly Ser Ile Gly Lys Gly Leu Ala Ala Val Lys Lys
        35                  40                  45

Ala Tyr Asp Lys Lys Val Ser Lys Gly Lys Ile Ser Gln Glu Asp Ala
    50                  55                  60

Asp Lys Ile Val Gly Arg Val Ser Thr Thr Thr Glu Leu Glu Lys Leu
65                  70                  75                  80

Ala Asp Cys Asp Leu Ile Ile Glu Ala Ser Glu Asp Met Asn Ile
                85                  90                  95

Lys Lys Asp Tyr Phe Gly Lys Leu Glu Glu Ile Cys Lys Pro Glu Thr
            100                 105                 110

Ile Phe Ala Thr Asn Thr Ser Ser Leu Ser Ile Thr Glu Val Ala Thr
        115                 120                 125

Ala Thr Lys Arg Pro Asp Lys Phe Ile Gly Met His Phe Phe Asn Pro
    130                 135                 140

Ala Asn Val Met Lys Leu Val Glu Ile Ile Arg Gly Met Asn Thr Ser
145                 150                 155                 160

Gln Glu Thr Phe Asp Ile Ile Lys Glu Ala Ser Ile Lys Ile Gly Lys
                165                 170                 175

Thr Pro Val Glu Val Ala Glu Ala Pro Gly Phe Val Val Asn Lys Ile
            180                 185                 190

Leu Val Pro Met Ile Asn Glu Ala Val Gly Ile Leu Ala Glu Gly Ile
        195                 200                 205

Ala Ser Ala Glu Asp Ile Asp Thr Ala Met Lys Leu Gly Ala Asn His
    210                 215                 220

Pro Met Gly Pro Leu Ala Leu Gly Asp Leu Ile Gly Leu Asp Val Val
225                 230                 235                 240

Leu Ala Val Met Asp Val Leu Tyr Ser Glu Thr Gly Asp Ser Lys Tyr
                245                 250                 255

Arg Ala His Thr Leu Leu Arg Lys Tyr Val Arg Ala Gly Trp Leu Gly
            260                 265                 270

Arg Lys Ser Gly Lys Gly Phe Phe Ala Tyr

<210> SEQ ID NO 4
<211> LENGTH: 258
<212> TYPE: PRT
<213> ORGANISM: Clostridium kluyveri

<400> SEQUENCE: 4

Met Glu Phe Lys Asn Ile Ile Leu Glu Lys Asp Gly Asn Val Ala Ser
1               5                   10                  15

Ile Thr Leu Asn Arg Pro Lys Ala Leu Asn Ala Leu Asn Ala Ala Thr
            20                  25                  30

Leu Lys Glu Ile Asp Ala Ala Ile Asn Asp Ile Ala Gly Asp Asp Asn
        35                  40                  45

Val Tyr Ala Val Ile Ile Thr Gly Ser Gly Lys Ala Phe Val Ala Gly
    50                  55                  60

Ala Asp Ile Ala Glu Met Lys Asp Leu Thr Ala Val Glu Gly Arg Lys
65                  70                  75                  80

Phe Ser Val Leu Gly Asn Lys Ile Phe Arg Lys Leu Glu Asn Leu Glu
                85                  90                  95

Lys Pro Val Ile Ala Ala Ile Asn Gly Phe Ala Leu Gly Gly Gly Cys
            100                 105                 110

Glu Leu Ser Leu Ser Cys Asp Ile Arg Ile Ala Ser Ser Lys Ala Lys
        115                 120                 125

Phe Gly Gln Pro Glu Val Gly Leu Gly Ile Thr Pro Gly Phe Gly Gly
    130                 135                 140

Thr Gln Arg Leu Ala Arg Ala Ile Gly Val Gly Met Ala Lys Glu Leu
145                 150                 155                 160

Ile Tyr Thr Gly Lys Val Ile Asn Ala Glu Glu Ala Leu Arg Ile Gly
                165                 170                 175

Leu Val Asn Lys Val Val Glu Pro Asp Lys Leu Leu Glu Glu Ala Lys
            180                 185                 190

Ala Leu Val Asp Ala Ile Ile Val Asn Ala Pro Ile Ala Val Arg Met
        195                 200                 205

Cys Lys Ala Ala Ile Asn Gln Gly Leu Gln Cys Asp Ile Asp Thr Gly
    210                 215                 220

Val Ala Tyr Glu Ala Glu Val Phe Gly Glu Cys Phe Ala Thr Glu Asp
225                 230                 235                 240

Arg Val Glu Gly Met Thr Ala Phe Val Glu Lys Arg Asp Lys Ala Phe
                245                 250                 255

Lys Asn

<210> SEQ ID NO 5
<211> LENGTH: 379
<212> TYPE: PRT
<213> ORGANISM: Clostridium kluyveri

<400> SEQUENCE: 5

Met Asp Phe Thr Leu Thr Asn Glu Gln Lys Phe Val Glu Gln Met Val
1               5                   10                  15

Ser Glu Phe Thr Glu Asn Glu Val Lys Pro Ile Ala Ala Glu Ile Asp
            20                  25                  30

Glu Thr Glu Arg Phe Pro Leu Glu Thr Val Glu Lys Phe Ala Lys Tyr
        35                  40                  45

Gly Met Met Gly Met Pro Phe Pro Val Glu Tyr Gly Gly Ser Gly Thr
    50                  55                  60

Asp Tyr Leu Ser Tyr Ile Ile Ala Val Glu Gly Leu Ala Lys Ser Cys
65                  70                  75                  80

Thr Ser Ser Ser Thr Ile Leu Ser Ala His Thr Ser Leu Cys Ala Ala
            85                  90                  95

Pro Ile Tyr Asp Trp Gly Thr Glu Glu Gln Lys Gln Lys Tyr Leu Val
            100                 105                 110

Pro Leu Ala Lys Gly Glu Lys Leu Gly Ala Phe Gly Leu Thr Glu Pro
            115                 120                 125

Asn Ala Gly Thr Asp Ala Ala Gly Gln Gln Thr Thr Ala Val Leu Glu
130                 135                 140

Gly Asp His Tyr Val Leu Asn Gly Gln Lys Ile Phe Ile Thr Asn Gly
145                 150                 155                 160

Ala Tyr Ala Asp Thr Phe Val Ile Phe Ala Met Thr Asp Arg Ser Lys
                165                 170                 175

Gly Thr Arg Gly Ile Thr Ala Phe Ile Val Glu Lys Asp Phe Pro Gly
                180                 185                 190

Phe Ser Ile Gly Lys Ser Glu Asp Lys Leu Gly Ile Arg Ala Ser Ser
            195                 200                 205

Thr Thr Glu Leu Ile Phe Glu Asn Cys Ile Val Pro Lys Glu Asn Met
210                 215                 220

Leu Gly Lys Glu Gly Lys Gly Phe Thr Val Ala Met His Thr Leu Asp
225                 230                 235                 240

Gly Gly Arg Ile Gly Ile Ala Ala Gln Ala Leu Gly Leu Ala Glu Gly
                245                 250                 255

Ala Leu Ala Glu Ala Leu Asn Tyr Met Lys Glu Arg Lys Gln Phe Gly
            260                 265                 270

Lys Ala Leu Tyr Lys Phe Gln Gly Leu Ala Trp Met Val Ala Glu Leu
            275                 280                 285

Asp Thr Lys Ile Glu Ala Val Lys Gln Leu Val Tyr Lys Ala Ala Val
290                 295                 300

Asn Lys Gln Met Gly Leu Pro Tyr Ser Val Glu Ala Ala Arg Ala Lys
305                 310                 315                 320

Leu Ala Ala Ala Thr Val Ala Met Glu Thr Thr Thr Lys Val Val Gln
                325                 330                 335

Ile Phe Gly Gly Tyr Gly Phe Thr Lys Asp Tyr Pro Val Glu Arg Met
            340                 345                 350

Met Arg Asp Ala Lys Ile Thr Glu Ile Tyr Glu Gly Thr Ser Gln Val
            355                 360                 365

Gln Lys Met Val Ile Ser Ala Asn Leu Phe Lys
            370                 375

<210> SEQ ID NO 6
<211> LENGTH: 379
<212> TYPE: PRT
<213> ORGANISM: Clostridium acetobutylicum

<400> SEQUENCE: 6

Met Asp Phe Asn Leu Thr Arg Glu Gln Glu Leu Val Arg Gln Met Val
1               5                   10                  15

Arg Glu Phe Ala Glu Asn Glu Val Lys Pro Ile Ala Ala Glu Ile Asp
            20                  25                  30

Glu Thr Glu Arg Phe Pro Met Glu Asn Val Lys Lys Met Gly Gln Tyr
        35                  40                  45

Gly Met Met Gly Ile Pro Phe Ser Lys Glu Tyr Gly Gly Ala Gly Gly

Asp Val Leu Ser Tyr Ile Ile Ala Val Glu Glu Leu Ser Lys Val Cys
65                  70                  75                  80

Gly Thr Thr Gly Val Ile Leu Ser Ala His Thr Ser Leu Cys Ala Ser
                85                  90                  95

Leu Ile Asn Glu His Gly Thr Glu Glu Gln Lys Gln Lys Tyr Leu Val
            100                 105                 110

Pro Leu Ala Lys Gly Glu Lys Ile Gly Ala Tyr Gly Leu Thr Glu Pro
        115                 120                 125

Asn Ala Gly Thr Asp Ser Gly Ala Gln Gln Thr Val Ala Val Leu Glu
    130                 135                 140

Gly Asp His Tyr Val Ile Asn Gly Ser Lys Ile Phe Ile Thr Asn Gly
145                 150                 155                 160

Gly Val Ala Asp Thr Phe Val Ile Phe Ala Met Thr Asp Arg Thr Lys
                165                 170                 175

Gly Thr Lys Gly Ile Ser Ala Phe Ile Ile Glu Lys Gly Phe Lys Gly
            180                 185                 190

Phe Ser Ile Gly Lys Val Glu Gln Lys Leu Gly Ile Arg Ala Ser Ser
        195                 200                 205

Thr Thr Glu Leu Val Phe Glu Asp Met Ile Val Pro Val Glu Asn Met
    210                 215                 220

Ile Gly Lys Glu Gly Lys Gly Phe Pro Ile Ala Met Lys Thr Leu Asp
225                 230                 235                 240

Gly Gly Arg Ile Gly Ile Ala Ala Gln Ala Leu Gly Ile Ala Glu Gly
                245                 250                 255

Ala Phe Asn Glu Ala Arg Ala Tyr Met Lys Glu Arg Lys Gln Phe Gly
            260                 265                 270

Arg Ser Leu Asp Lys Phe Gln Gly Leu Ala Trp Met Met Ala Asp Met
        275                 280                 285

Asp Val Ala Ile Glu Ser Ala Arg Tyr Leu Val Tyr Lys Ala Ala Tyr
    290                 295                 300

Leu Lys Gln Ala Gly Leu Pro Tyr Thr Val Asp Ala Ala Arg Ala Lys
305                 310                 315                 320

Leu His Ala Ala Asn Val Ala Met Asp Val Thr Thr Lys Ala Val Gln
                325                 330                 335

Leu Phe Gly Gly Tyr Gly Tyr Thr Lys Asp Tyr Pro Val Glu Arg Met
            340                 345                 350

Met Arg Asp Ala Lys Ile Thr Glu Ile Tyr Glu Gly Thr Ser Glu Val
        355                 360                 365

Gln Lys Leu Val Ile Ser Gly Lys Ile Phe Arg
    370                 375

<210> SEQ ID NO 7
<211> LENGTH: 562
<212> TYPE: PRT
<213> ORGANISM: Clostridium kluyveri

<400> SEQUENCE: 7

Met Asn Phe Glu Leu Thr Lys Glu Gln Gln Met Ile Arg Asp Asn Val
1               5                   10                  15

Arg Lys Phe Ala Glu Ala Lys Ile Glu Pro Ile Ala Phe Gln Leu Asp
                20                  25                  30

Glu Lys Asn Ile Phe Pro Glu Glu Ile Val Asn Glu Met Gly Asp Leu
            35                  40                  45

```
Ser Ile Met Gly Leu Pro Tyr Pro Lys Glu Tyr Gly Gly Ala Gly Lys
    50                  55                  60

Asp Val Leu Ser Tyr Ala Ile Ala Val Glu Glu Leu Ser Arg Val Asp
65                  70                  75                  80

Ala Gly Val Gly Val Ile Leu Ser Ala His Thr Ser Leu Gly Thr Trp
                85                  90                  95

Pro Ile Met Glu Phe Gly Thr Lys Glu Gln Lys Glu Lys Tyr Leu Val
                100                 105                 110

Pro Leu Ala Ser Gly Lys Lys Ile Ala Ala Phe Gly Leu Thr Glu Pro
            115                 120                 125

Asn Ala Gly Ser Asp Ala Gly Lys Thr Glu Thr Thr Ala Val Leu Glu
130                 135                 140

Gly Asp His Tyr Val Ile Asn Gly Ser Lys Val Phe Ile Thr Asn Ala
145                 150                 155                 160

Asp Tyr Ala Asp Thr Tyr Val Ile Phe Ala Val Thr Thr Pro Gly Leu
                165                 170                 175

Gly Thr Lys Gly Ile Ser Ala Phe Ile Ile Glu Lys Gly Met Asp Gly
            180                 185                 190

Phe Thr Phe Gly Thr His Tyr Asn Lys Met Gly Ile Arg Ser Ser Ala
        195                 200                 205

Thr Ala Glu Leu Leu Phe Lys Asn Leu Lys Val Pro Lys Tyr Asn Leu
210                 215                 220

Leu Gly Lys Glu Asn Glu Gly Phe Lys Ile Ala Met Gln Thr Leu Glu
225                 230                 235                 240

Gly Gly Arg Ile Gly Ile Ala Ala Gln Ala Leu Gly Ile Ala Gln Gly
                245                 250                 255

Ala Tyr Glu Lys Ala Leu Ser Tyr Ser Lys Glu Arg Val Gln Phe Gly
            260                 265                 270

Lys Pro Ile Ser Arg Gln Gln Ser Ile Ala Phe Lys Leu Ala Asp Met
        275                 280                 285

Ala Thr Lys Ile Arg Ala Ala Arg Phe Met Val Tyr Ser Ala Ala Val
    290                 295                 300

Leu Lys Gln Glu His Lys Asn Tyr Gly Met Glu Ser Ala Met Ala Lys
305                 310                 315                 320

Leu Tyr Ala Ser Asp Ile Cys Leu Glu Val Val Asn Asp Ala Val Gln
                325                 330                 335

Ile Tyr Gly Gly Ser Gly Phe Ile Lys Gly Phe Pro Val Glu Arg Met
            340                 345                 350

Tyr Arg Asp Ala Lys Ile Cys Thr Ile Tyr Glu Gly Thr Asn Glu Ile
        355                 360                 365

Gln Arg Leu Ile Ile Ser Asn Asp Ile Leu Gly Lys Pro Lys Lys Glu
    370                 375                 380

Pro Ile Glu Glu Asn Lys Glu Asn Lys Val Asn Lys Ala Lys Pro Ile
385                 390                 395                 400

Thr Gly Asn Arg Arg Val Ile Ile Lys Glu Gly Ser Pro Lys Glu
                405                 410                 415

Lys Val Asp Ala Phe Leu Asn Tyr Ile Lys Ser Glu Asn Ile Asp Ile
                420                 425                 430

Asn Lys Ser Glu Ala Ser Lys Gly Ser Ile Ala Asp Ala Asp Lys Val
            435                 440                 445

Cys Ser Ile Gly Leu Gly Leu Lys Asp Lys Lys Asp Leu Pro Leu Ile
450                 455                 460

Gln Ser Leu Ala Asp Thr Val Gly Ala Glu Leu Gly Cys Ser Arg Pro
```

```
              465                 470                 475                 480
Val Ala Glu Glu Arg Glu Trp Leu Pro Leu Asp Arg Tyr Val Gly Ile
                    485                 490                 495

Ser Gly Gln Lys Phe Gly Gly Thr Phe Tyr Leu Ala Ile Gly Ile Ser
                500                 505                 510

Gly Gln Val Gln His Leu Lys Gly Ile Glu Asn Ala Gly Ile Ile Thr
                515                 520                 525

Ala Ile Asn Ile Asp Glu Asp Ala Pro Ile Phe Lys Ser Ser Asp Tyr
            530                 535                 540

Gly Ile Val Gly Asp Leu Tyr Glu Ile Val Pro Leu Leu Ile Glu Ala
545                 550                 555                 560

Leu Lys

<210> SEQ ID NO 8
<211> LENGTH: 259
<212> TYPE: PRT
<213> ORGANISM: Clostridium kluyveri

<400> SEQUENCE: 8

Met Lys Ile Val Val Cys Leu Lys Gln Val Pro Asp Thr Thr Glu Val
1               5                   10                  15

Lys Ile Asp Pro Lys Thr Gly Thr Leu Ile Arg Glu Gly Val Pro Ser
            20                  25                  30

Ile Ile Asn Pro Asp Asp Lys Asn Ala Leu Glu Glu Ser Ile Ala Leu
        35                  40                  45

Lys Glu Lys Val Gly Gly Thr Val Thr Val Val Ser Met Gly Pro Pro
    50                  55                  60

Gln Ala Val Asp Ala Leu Arg Glu Ala Leu Ala Met Gly Ala Asp Glu
65                  70                  75                  80

Ala Ile Leu Val Ser Asp Arg Ala Phe Ala Gly Ala Asp Thr Gln Ala
                85                  90                  95

Thr Ser Tyr Ala Leu Ala Gly Ala Leu Lys Asn Leu Glu Tyr Asp Leu
            100                 105                 110

Ile Phe Ala Gly Arg Gln Ala Ile Asp Gly Asp Thr Ala Gln Val Gly
        115                 120                 125

Pro Gln Ile Ala Glu Lys Leu Gly Ile Pro Gln Ile Thr Tyr Val Glu
    130                 135                 140

Lys Val Asp Val Asp Gly Asp Thr Leu Thr Val Gln Arg Ala Trp Glu
145                 150                 155                 160

Asp Gly Tyr Glu Val Ala Lys Ile Lys Thr Pro Cys Met Leu Thr Ala
                165                 170                 175

Ile Lys Glu Leu Asn Gln Pro Arg Tyr Met Asn Met Lys Asn Ile Phe
            180                 185                 190

Glu Val Phe Lys Lys Glu Val Lys Ile Trp Ser Ala Asp Asp Leu Asp
        195                 200                 205

Val Asp Lys Asn Lys Leu Gly Leu Asn Gly Ser Cys Thr Lys Val Lys
    210                 215                 220

Arg Ser His Thr Lys Glu Ala Lys Gly Ala Gly Glu Ile Val Asn Lys
225                 230                 235                 240

Pro Ile Lys Glu Ala Val Ala Tyr Ser Ile Ser Lys Leu Arg Glu Lys
                245                 250                 255

His Val Ile

<210> SEQ ID NO 9
```

<211> LENGTH: 334
<212> TYPE: PRT
<213> ORGANISM: Clostridium kluyveri

<400> SEQUENCE: 9

Met Asn Leu Ala Glu Tyr Lys Gly Val Trp Val Phe Ala Glu Gln Arg
1               5                   10                  15

Asp Gly Glu Leu Gln Lys Val Ala Leu Gln Leu Val Gly Lys Gly Arg
            20                  25                  30

Glu Leu Ala Asp Thr Leu Gly Val Glu Leu Thr Ala Val Leu Leu Gly
        35                  40                  45

Ser Glu Val Asp Leu Ala Lys Glu Leu Val Ala Tyr Gly Ala Asp
    50                  55                  60

Asn Val Leu Tyr Ala Asp Ser Pro Leu Leu Lys His Tyr Thr Thr Asp
65                  70                  75                  80

Gly Tyr Thr Lys Val Ile Asp Glu Leu Ile Lys Glu Arg Lys Pro Glu
                85                  90                  95

Ile Leu Leu Ile Gly Ala Thr Phe Ile Gly Arg Asp Leu Gly Pro Arg
            100                 105                 110

Val Ala Gly Arg Val Phe Thr Gly Leu Thr Ala Asp Cys Thr Gly Leu
        115                 120                 125

Asp Ile Asp Glu Ala Thr Lys Asn Leu Met Met Thr Arg Pro Ala Phe
130                 135                 140

Gly Gly Asn Leu Met Ala Thr Ile Ala Cys Glu Lys Thr Arg Pro Gln
145                 150                 155                 160

Met Ser Thr Val Arg Pro Gly Val Phe Asn Ala Leu Pro Arg Asp Ala
                165                 170                 175

Ser Arg Thr Gly Lys Ile Glu Lys Ile Ala Ala Asn Val Ala Lys Asp
            180                 185                 190

Asp Ile Arg Ile Glu Val Leu Glu Val Val Lys Ser Ala Gly Asp Thr
        195                 200                 205

Ile Asp Ile Ser Glu Ala Asp Val Ile Val Ser Gly Gly Arg Gly Leu
210                 215                 220

Gly Gly Pro Asp Gly Phe Lys Val Leu Lys Glu Leu Ala Asp Leu Leu
225                 230                 235                 240

Gly Gly Thr Ile Gly Gly Ser Arg Ala Thr Ile Asp Ala Gly Trp Ile
                245                 250                 255

Asp Lys Ser Tyr Gln Val Gly Gln Thr Gly Lys Thr Val Arg Pro Gly
            260                 265                 270

Leu Tyr Ile Ala Cys Gly Ile Ser Gly Gln Ile Gln His Leu Ala Gly
        275                 280                 285

Met Gln Asp Ser Gly Phe Ile Val Ala Ile Asn Lys Asp Glu Asn Ala
290                 295                 300

Pro Met Met Gln Val Ala Asp Leu Ala Ile Val Gly Asp Leu Tyr Lys
305                 310                 315                 320

Val Val Pro Glu Phe Val Glu Gln Val Lys Ala Leu Asn Leu
                325                 330

<210> SEQ ID NO 10
<211> LENGTH: 336
<212> TYPE: PRT
<213> ORGANISM: Clostridium acetobutylicum

<400> SEQUENCE: 10

Met Asn Lys Ala Asp Tyr Lys Gly Val Trp Val Phe Ala Glu Gln Arg
1               5                   10                  15

```
Asp Gly Glu Leu Gln Lys Val Ser Leu Glu Leu Leu Gly Lys Gly Lys
            20                  25                  30

Glu Met Ala Glu Lys Leu Gly Val Glu Leu Thr Ala Val Leu Leu Gly
        35                  40                  45

His Asn Thr Glu Lys Met Ser Lys Asp Leu Leu Ser His Gly Ala Asp
    50                  55                  60

Lys Val Leu Ala Ala Asp Asn Glu Leu Leu Ala His Phe Ser Thr Asp
65                  70                  75                  80

Gly Tyr Ala Lys Val Ile Cys Asp Leu Val Asn Glu Arg Lys Pro Glu
                85                  90                  95

Ile Leu Phe Ile Gly Ala Thr Phe Ile Gly Arg Asp Leu Gly Pro Arg
            100                 105                 110

Ile Ala Ala Arg Leu Ser Thr Gly Leu Thr Ala Asp Cys Thr Ser Leu
        115                 120                 125

Asp Ile Asp Val Glu Asn Arg Asp Leu Leu Ala Thr Arg Pro Ala Phe
130                 135                 140

Gly Gly Asn Leu Ile Ala Thr Ile Val Cys Ser Asp His Arg Pro Gln
145                 150                 155                 160

Met Ala Thr Val Arg Pro Gly Val Phe Glu Lys Leu Pro Val Asn Asp
                165                 170                 175

Ala Asn Val Ser Asp Asp Lys Ile Glu Lys Val Ala Ile Lys Leu Thr
            180                 185                 190

Ala Ser Asp Ile Arg Thr Lys Val Ser Lys Val Val Lys Leu Ala Lys
        195                 200                 205

Asp Ile Ala Asp Ile Gly Glu Ala Lys Val Leu Val Ala Gly Gly Arg
210                 215                 220

Gly Val Gly Ser Lys Glu Asn Phe Glu Lys Leu Glu Glu Leu Ala Ser
225                 230                 235                 240

Leu Leu Gly Gly Thr Ile Ala Ala Ser Arg Ala Ala Ile Glu Lys Glu
                245                 250                 255

Trp Val Asp Lys Asp Leu Gln Val Gly Gln Thr Gly Lys Thr Val Arg
            260                 265                 270

Pro Thr Leu Tyr Ile Ala Cys Gly Ile Ser Gly Ala Ile Gln His Leu
        275                 280                 285

Ala Gly Met Gln Asp Ser Asp Tyr Ile Ile Ala Ile Asn Lys Asp Val
290                 295                 300

Glu Ala Pro Ile Met Lys Val Ala Asp Leu Ala Ile Val Gly Asp Val
305                 310                 315                 320

Asn Lys Val Val Pro Glu Leu Ile Ala Gln Val Lys Ala Ala Asn Asn
                325                 330                 335

<210> SEQ ID NO 11
<211> LENGTH: 259
<212> TYPE: PRT
<213> ORGANISM: Clostridium acetobutylicum

<400> SEQUENCE: 11

Met Asn Ile Val Val Cys Leu Lys Gln Val Pro Asp Thr Ala Glu Val
1               5                   10                  15

Arg Ile Asp Pro Val Lys Gly Thr Leu Ile Arg Glu Gly Val Pro Ser
            20                  25                  30

Ile Ile Asn Pro Asp Asp Lys Asn Ala Leu Glu Glu Ala Leu Val Leu
        35                  40                  45

Lys Asp Asn Tyr Gly Ala His Val Thr Val Ile Ser Met Gly Pro Pro
```

-continued

```
                50                  55                  60
Gln Ala Lys Asn Ala Leu Val Glu Ala Leu Ala Met Gly Ala Asp Glu
 65                  70                  75                  80

Ala Val Leu Leu Thr Asp Arg Ala Phe Gly Gly Ala Asp Thr Leu Ala
                 85                  90                  95

Thr Ser His Thr Ile Ala Ala Gly Ile Lys Lys Leu Lys Tyr Asp Ile
                100                 105                 110

Val Phe Ala Gly Arg Gln Ala Ile Asp Gly Asp Thr Ala Gln Val Gly
            115                 120                 125

Pro Glu Ile Ala Glu His Leu Gly Ile Pro Gln Val Thr Tyr Val Glu
        130                 135                 140

Lys Val Glu Val Asp Gly Asp Thr Leu Lys Ile Arg Lys Ala Trp Glu
145                 150                 155                 160

Asp Gly Tyr Glu Val Val Glu Val Lys Thr Pro Val Leu Leu Thr Ala
                165                 170                 175

Ile Lys Glu Leu Asn Val Pro Arg Tyr Met Ser Val Glu Lys Ile Phe
                180                 185                 190

Gly Ala Phe Asp Lys Glu Val Lys Met Trp Thr Ala Asp Asp Ile Asp
            195                 200                 205

Val Asp Lys Ala Asn Leu Gly Leu Lys Gly Ser Pro Thr Lys Val Lys
210                 215                 220

Lys Ser Ser Thr Lys Glu Val Lys Gly Gln Gly Glu Val Ile Asp Lys
225                 230                 235                 240

Pro Val Lys Glu Ala Ala Ala Tyr Val Val Ser Lys Leu Lys Glu Glu
                245                 250                 255

His Tyr Ile

<210> SEQ ID NO 12
<211> LENGTH: 262
<212> TYPE: PRT
<213> ORGANISM: Clostridium kluyveri

<400> SEQUENCE: 12

Met Phe Asn Leu Pro Glu Glu Val Thr Tyr Thr Ile Asn Leu Lys Asn
 1               5                  10                  15

Leu Ile Lys Asp Ile Lys Pro Glu Ile Phe Leu Ile Gly Ala Thr Thr
                20                  25                  30

Leu Gly Arg Ser Leu Ala Pro Arg Leu Ala Ala Ser Leu Asn Thr Gly
             35                  40                  45

Leu Thr Ala Asp Cys Thr Gly Leu Glu Ile Asp Glu Asp Arg Lys Leu
 50                  55                  60

Val Gln Ile Arg Pro Ala Phe Ser Glu Asn Ile Leu Ala His Ile Lys
 65                  70                  75                  80

Thr Tyr Thr Tyr Pro Gln Met Ala Thr Val Arg Tyr Lys Glu Phe Asp
                85                  90                  95

Glu Gly Thr Arg Asp Ala Lys Arg Gln Gly Asp Ile Leu Lys Val Glu
            100                 105                 110

Ala Leu Arg Leu Glu Asn Glu Leu Val Lys Val Ile Thr Gln Leu Arg
        115                 120                 125

Ser Gln Glu Ile Asn Ile Ser Asp Ala Asn Val Val Ala Ala Gly
    130                 135                 140

Lys Gly Leu Lys Lys Ala Glu Asp Met Ala Met Leu Lys Glu Leu Ala
145                 150                 155                 160

Asp Leu Leu Gly Gly Val Val Gly Ala Ser Arg Glu Ile Val Glu Glu
```

```
                165                 170                 175
Gly Phe Ile Ser Lys Asp Phe Gln Val Gly Tyr Ser Gly Asn Arg Val
            180                 185                 190

Lys Pro Lys Leu Tyr Ile Ala Cys Gly Ile Ser Gly Ala Pro Gln His
        195                 200                 205

Leu Ala Gly Met Lys Glu Ser Gly Phe Ile Val Ala Ile Asn Thr Asp
    210                 215                 220

Pro Ser Ala Pro Ile Phe Asn Ile Ala Asp Tyr Gly Ile Val Asp Asp
225                 230                 235                 240

Met Tyr Lys Val Ile Pro Asp Leu Ile Thr Lys Ile Lys Glu Ser Ser
                245                 250                 255

Leu Glu Thr Ile Asn Cys
            260

<210> SEQ ID NO 13
<211> LENGTH: 297
<212> TYPE: PRT
<213> ORGANISM: Clostridium kluyveri

<400> SEQUENCE: 13

Met Gly Gly Thr Ala Ala Asp Ile Ser Pro Gln Arg Asn Arg Ser Val
1               5                   10                  15

Phe Leu Phe Ala Ile Cys Leu Arg Glu Arg Lys Glu Ala Leu Met Asp
            20                  25                  30

Ile Ile Val Leu Val Lys Gln Val Pro Asp Met Glu Lys Val Lys Phe
        35                  40                  45

Asp Arg Glu Lys Gly Val Val Asp Arg Thr Ser Ala Ser Ala Glu Ile
    50                  55                  60

Asn Pro Phe Asp Leu Asn Ala Leu Glu Thr Ala Val Gln Ile Ala Glu
65                  70                  75                  80

Asn Ile Asp Ala Arg Val Thr Ala Val Ser Met Gly Pro Pro Asn Thr
                85                  90                  95

Glu Ser Ala Leu Lys Glu Cys Ile Ala Arg Gly Ala His Glu Gly Val
            100                 105                 110

Leu Val Ser Asp Arg Lys Phe Gly Gly Ser Asp Thr Lys Ala Thr Ser
        115                 120                 125

Lys Ile Leu Ala Ser Ala Ile Lys Lys Leu Gly Ala Tyr Asp Leu Val
    130                 135                 140

Ile Ala Gly Glu Lys Thr Val Asp Gly Asp Thr Gly Gln Val Gly Pro
145                 150                 155                 160

Glu Val Ala Glu Phe Leu Asn Ile Pro His Ala Ser Tyr Val Ser Lys
                165                 170                 175

Ile Thr Glu Met Asn Lys Asp Ser Met Glu Val His Ser Glu Ile Trp
            180                 185                 190

Glu Gly Thr Tyr Leu Lys Ser Ile Lys Phe Pro Cys Leu Ile Thr Val
        195                 200                 205

Thr Lys Asp Ile Asn His Pro Arg Leu Pro Ser Phe Lys Asn Lys Met
    210                 215                 220

Lys Ala Arg Lys Ala Glu Ile Lys Ile Leu Lys Leu Glu Asp Leu Glu
225                 230                 235                 240

Glu Phe Leu Asn Glu Asp Asn Val Gly Phe Lys Gly Ser Pro Thr Lys
                245                 250                 255

Val Lys Lys Ile Glu Ile Pro Gln Ile Glu Lys Arg Gln Gly Lys Ile
            260                 265                 270
```

```
Tyr Arg Glu Ser Asp Thr Val Glu Ala Glu Asn Glu Leu Ile Asn Ile
            275                 280                 285

Phe Lys Lys Ile Lys Val Leu Glu Val
        290                 295
```

<210> SEQ ID NO 14
<211> LENGTH: 539
<212> TYPE: PRT
<213> ORGANISM: Euglena gracilis

<400> SEQUENCE: 14

```
Met Ser Cys Pro Ala Ser Pro Ser Ala Ala Val Val Ser Ala Gly Ala
1               5                   10                  15

Leu Cys Leu Cys Val Ala Thr Val Leu Leu Ala Thr Gly Ser Asn Pro
            20                  25                  30

Thr Ala Leu Ser Thr Ala Ser Thr Arg Ser Pro Thr Ser Leu Val Arg
        35                  40                  45

Gly Val Asp Arg Gly Leu Met Arg Pro Thr Thr Ala Ala Ala Leu Thr
    50                  55                  60

Thr Met Arg Glu Val Pro Gln Met Ala Glu Gly Phe Ser Gly Glu Ala
65                  70                  75                  80

Thr Ser Ala Trp Ala Ala Gly Pro Gln Trp Ala Ala Pro Leu Val
                85                  90                  95

Ala Ala Ala Ser Ser Ala Leu Ala Leu Trp Trp Trp Ala Arg Arg
                100                 105                 110

Ser Val Arg Arg Pro Leu Ala Ala Leu Ala Glu Leu Pro Thr Ala Val
            115                 120                 125

Thr His Leu Ala Pro Pro Met Ala Met Phe Thr Thr Thr Ala Lys Val
    130                 135                 140

Ile Gln Pro Lys Ile Arg Gly Phe Ile Cys Thr Thr Thr His Pro Ile
145                 150                 155                 160

Gly Cys Glu Lys Arg Val Gln Glu Glu Ile Ala Tyr Ala Arg Ala His
                165                 170                 175

Pro Pro Thr Ser Pro Gly Pro Lys Arg Val Leu Val Ile Gly Cys Ser
            180                 185                 190

Thr Gly Tyr Gly Leu Ser Thr Arg Ile Thr Ala Ala Phe Gly Tyr Gln
        195                 200                 205

Ala Ala Thr Leu Gly Val Phe Leu Ala Gly Pro Pro Thr Lys Gly Arg
    210                 215                 220

Pro Ala Ala Ala Gly Trp Tyr Asn Thr Val Ala Phe Glu Lys Ala Ala
225                 230                 235                 240

Leu Glu Ala Gly Leu Tyr Ala Arg Ser Leu Asn Gly Asp Ala Phe Asp
                245                 250                 255

Ser Thr Thr Lys Ala Arg Thr Val Glu Ala Ile Lys Arg Asp Leu Gly
            260                 265                 270

Thr Val Asp Leu Val Val Tyr Ser Ile Ala Ala Pro Lys Arg Thr Asp
        275                 280                 285

Pro Ala Thr Gly Val Leu His Lys Ala Cys Leu Lys Pro Ile Gly Ala
    290                 295                 300

Thr Tyr Thr Asn Arg Thr Val Asn Thr Asp Lys Ala Glu Val Thr Asp
305                 310                 315                 320

Val Ser Ile Glu Pro Ala Ser Pro Glu Glu Ile Ala Asp Thr Val Lys
                325                 330                 335

Val Met Gly Gly Glu Asp Trp Glu Leu Trp Ile Gln Ala Leu Ser Glu
            340                 345                 350
```

```
Ala Gly Val Leu Ala Glu Gly Ala Lys Thr Val Ala Tyr Ser Tyr Ile
            355                 360                 365

Gly Pro Glu Met Thr Trp Pro Val Tyr Trp Ser Gly Thr Ile Gly Glu
    370                 375                 380

Ala Lys Lys Asp Val Glu Lys Ala Ala Lys Arg Ile Thr Gln Gln Tyr
385                 390                 395                 400

Gly Cys Pro Ala Tyr Pro Val Val Ala Lys Ala Leu Val Thr Gln Ala
                405                 410                 415

Ser Ser Ala Ile Pro Val Val Pro Leu Tyr Ile Cys Leu Leu Tyr Arg
            420                 425                 430

Val Met Lys Glu Lys Gly Thr His Glu Gly Cys Ile Glu Gln Met Val
            435                 440                 445

Arg Leu Leu Thr Thr Lys Leu Tyr Pro Glu Asn Gly Ala Pro Ile Val
            450                 455                 460

Asp Glu Ala Gly Arg Val Arg Val Asp Asp Trp Glu Met Ala Glu Asp
465                 470                 475                 480

Val Gln Gln Ala Val Lys Asp Leu Trp Ser Gln Val Ser Thr Ala Asn
                485                 490                 495

Leu Lys Asp Ile Ser Asp Phe Ala Gly Tyr Gln Thr Glu Phe Leu Arg
            500                 505                 510

Leu Phe Gly Phe Gly Ile Asp Gly Val Asp Tyr Asp Gln Pro Val Asp
            515                 520                 525

Val Glu Ala Asp Leu Pro Ser Ala Ala Gln Gln
            530                 535

<210> SEQ ID NO 15
<211> LENGTH: 397
<212> TYPE: PRT
<213> ORGANISM: Treponema denticola

<400> SEQUENCE: 15

Met Ile Val Lys Pro Met Val Arg Asn Asn Ile Cys Leu Asn Ala His
1               5                   10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
    50                  55                  60

Thr Ala Ala Phe Gly Tyr Gly Ala Ala Thr Ile Gly Val Ser Phe Glu
65                  70                  75                  80

Lys Ala Gly Ser Glu Thr Lys Tyr Gly Thr Pro Gly Trp Tyr Asn Asn
                85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
    130                 135                 140

Ala Ser Pro Val Arg Thr Asp Pro Asp Thr Gly Ile Met His Lys Ser
145                 150                 155                 160

Val Leu Lys Pro Phe Gly Lys Thr Phe Thr Gly Lys Thr Val Asp Pro
                165                 170                 175

Phe Thr Gly Glu Leu Lys Glu Ile Ser Ala Glu Pro Ala Asn Asp Glu
```

```
            180                 185                 190
Glu Ala Ala Thr Val Lys Val Met Gly Gly Glu Asp Trp Glu Arg
        195                 200                 205

Trp Ile Lys Gln Leu Ser Lys Glu Gly Leu Leu Glu Glu Gly Cys Ile
        210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
                245                 250                 255

His Arg Leu Asn Lys Glu Asn Pro Ser Ile Arg Ala Phe Val Ser Val
            260                 265                 270

Asn Lys Gly Leu Val Thr Arg Ala Ser Ala Val Ile Pro Val Ile Pro
        275                 280                 285

Leu Tyr Leu Ala Ser Leu Phe Lys Val Met Lys Glu Lys Gly Asn His
    290                 295                 300

Glu Gly Cys Ile Glu Gln Ile Thr Arg Leu Tyr Ala Glu Arg Leu Tyr
305                 310                 315                 320

Arg Lys Asp Gly Thr Ile Pro Val Asp Glu Glu Asn Arg Ile Arg Ile
                325                 330                 335

Asp Asp Trp Glu Leu Glu Asp Val Gln Lys Ala Val Ser Ala Leu
            340                 345                 350

Met Glu Lys Val Thr Gly Glu Asn Ala Glu Ser Leu Thr Asp Leu Ala
        355                 360                 365

Gly Tyr Arg His Asp Phe Leu Ala Ser Asn Gly Phe Asp Val Glu Gly
    370                 375                 380

Ile Asn Tyr Glu Ala Glu Val Glu Arg Phe Asp Arg Ile
385                 390                 395

<210> SEQ ID NO 16
<211> LENGTH: 344
<212> TYPE: PRT
<213> ORGANISM: Caenorhabditis elegans

<400> SEQUENCE: 16

Met Leu Lys Val Leu Ser Leu Arg Ser Ala Leu Gln Arg Ala Ala Ser
1               5                   10                  15

Thr Arg Gln Leu Val Tyr Glu Gly Tyr Arg Asn Pro Pro Glu Ala Ile
            20                  25                  30

Gln Leu Lys Thr Val Thr Ile Ala Asp Lys Pro Ser Ala Asp Gln Val
        35                  40                  45

Leu Val Gln Trp Ile Ala Ala Pro Ile Asn Pro Ala Asp Leu Asn Gln
    50                  55                  60

Ile Gln Gly Val Tyr Pro Val Lys Pro Ala Leu Pro Ala Val Gly Gly
65                  70                  75                  80

Asn Glu Gly Phe Gly Lys Val Ile Ser Val Gly Ser Asn Val Ser Ser
                85                  90                  95

Ile Lys Val Gly Asp His Val Ile Pro Asp Arg Ser Gly Leu Gly Thr
            100                 105                 110

Trp Arg Glu Leu Gly Leu His Gln Glu Asn Asp Leu Phe Pro Ile Asp
        115                 120                 125

Asn Thr Leu Ser Met Glu Tyr Ala Ala Thr Phe Gln Val Asn Pro Pro
    130                 135                 140

Thr Ala Tyr Arg Met Leu Lys Asp Phe Ile Asp Leu Lys Lys Gly Asp
145                 150                 155                 160
```

```
Thr Val Ala Gln Asn Gly Ala Asn Ser Ala Val Gly Lys His Val Ile
                165                 170                 175

Gln Ile Cys Arg Ile Leu Gly Ile Lys Thr Val Asn Val Val Arg Ser
            180                 185                 190

Arg Asp Asn Leu Glu Glu Leu Val Lys Glu Leu Lys Asp Leu Gly Ala
        195                 200                 205

Asp Glu Val Ile Thr Gln Glu Glu Leu Tyr Ser Arg Lys Lys Lys Phe
    210                 215                 220

Pro Gly Val Lys Leu Ala Leu Asn Cys Val Gly Gly Arg Ser Ser Leu
225                 230                 235                 240

Phe Leu Ala Ser Leu Leu Asp His Gly Gly Cys Met Val Thr Tyr Gly
                245                 250                 255

Gly Met Ser Lys Gln Pro Val Asp Cys Pro Thr Gly Pro Leu Ile Phe
            260                 265                 270

Lys Asp Ile Ser Leu Arg Gly Phe Trp Met Ser Arg Trp Tyr Asp Ile
        275                 280                 285

Gln Lys Ser Pro Glu Lys Arg His Glu Met Tyr Gln Glu Leu Ala Gly
    290                 295                 300

Trp Met Lys Ser Gly Glu Ile Lys Lys Gln Glu Ile Val Lys Asn Arg
305                 310                 315                 320

Leu Glu Asp His Ala Lys Ala Leu Asp Thr Ala Leu Ser Lys Phe Asp
                325                 330                 335

Lys Lys Gln Phe Phe Val Leu Glu
            340

<210> SEQ ID NO 17
<211> LENGTH: 447
<212> TYPE: PRT
<213> ORGANISM: Streptomyces collinus

<400> SEQUENCE: 17

Val Thr Val Lys Asp Ile Leu Asp Ala Ile Gln Ser Lys Asp Ala Thr
1               5                   10                  15

Ser Ala Asp Phe Ala Ala Leu Gln Leu Pro Glu Ser Tyr Arg Ala Ile
            20                  25                  30

Thr Val His Lys Asp Glu Thr Glu Met Phe Ala Gly Leu Glu Thr Arg
        35                  40                  45

Asp Lys Asp Pro Arg Lys Ser Ile His Leu Asp Glu Val Pro Val Pro
    50                  55                  60

Glu Leu Gly Pro Gly Glu Ala Leu Val Ala Val Met Ala Ser Ser Val
65                  70                  75                  80

Asn Tyr Asn Ser Val Trp Thr Ser Ile Phe Glu Pro Val Ser Thr Phe
                85                  90                  95

Ala Phe Leu Glu Arg Tyr Gly Lys Leu Ser Pro Leu Thr Lys Arg His
            100                 105                 110

Asp Leu Pro Tyr His Ile Ile Gly Ser Asp Leu Ala Gly Val Val Leu
        115                 120                 125

Arg Thr Gly Pro Gly Val Asn Ala Trp Gln Pro Gly Asp Glu Val Val
    130                 135                 140

Ala His Cys Leu Ser Val Glu Leu Glu Ser Pro Asp Gly His Asp Asp
145                 150                 155                 160

Thr Met Leu Asp Pro Glu Gln Arg Ile Trp Gly Phe Glu Thr Asn Phe
                165                 170                 175

Gly Gly Leu Ala Glu Ile Ala Leu Val Lys Thr Asn Gln Leu Met Pro
            180                 185                 190
```

Lys Pro Lys His Leu Thr Trp Glu Glu Ala Ala Ala Pro Gly Leu Val
            195                 200                 205

Asn Ser Thr Ala Tyr Arg Gln Leu Val Ser Arg Asn Gly Ala Ala Met
        210                 215                 220

Lys Gln Gly Asp Asn Val Leu Ile Trp Gly Ala Ser Gly Gly Leu Gly
225                 230                 235                 240

Ser Tyr Ala Thr Gln Phe Ala Leu Ala Gly Gly Ala Asn Pro Ile Cys
                245                 250                 255

Val Val Ser Ser Pro Gln Lys Ala Glu Ile Cys Arg Ser Met Gly Ala
            260                 265                 270

Glu Ala Ile Ile Asp Arg Asn Ala Glu Gly Tyr Lys Phe Trp Lys Asp
        275                 280                 285

Glu His Thr Gln Asp Pro Lys Glu Trp Lys Arg Phe Gly Lys Arg Ile
    290                 295                 300

Arg Glu Leu Thr Gly Gly Glu Asp Ile Asp Ile Val Phe Glu His Pro
305                 310                 315                 320

Gly Arg Glu Thr Phe Gly Ala Ser Val Tyr Val Thr Arg Lys Gly Gly
                325                 330                 335

Thr Ile Thr Thr Cys Ala Ser Thr Ser Gly Tyr Met His Glu Tyr Asp
            340                 345                 350

Asn Arg Tyr Leu Trp Met Ser Leu Lys Arg Ile Ile Gly Ser His Phe
        355                 360                 365

Ala Asn Tyr Arg Glu Ala Tyr Glu Ala Asn Arg Leu Ile Ala Lys Gly
    370                 375                 380

Lys Ile His Pro Thr Leu Ser Lys Thr Tyr Ser Leu Glu Glu Thr Gly
385                 390                 395                 400

Gln Ala Ala Tyr Asp Val His Arg Asn Leu His Gln Gly Lys Val Gly
                405                 410                 415

Val Leu Cys Leu Ala Pro Glu Glu Gly Leu Gly Val Arg Asp Ala Glu
            420                 425                 430

Met Arg Ala Gln His Ile Asp Ala Ile Asn Arg Phe Arg Asn Val
        435                 440                 445

<210> SEQ ID NO 18
<211> LENGTH: 245
<212> TYPE: PRT
<213> ORGANISM: Clostridium acetobutylicum

<400> SEQUENCE: 18

Met Asp Thr Trp Ala Val Ile Asn Asn Met Asp Thr Asn Glu Lys Leu
1               5                   10                  15

Ile Ala Ala His Pro Asp Met Ala Pro Lys Phe Ser Ile Leu Asp Pro
            20                  25                  30

Thr Tyr Thr Tyr Thr Val Pro Thr Asn Gln Thr Ala Ala Gly Thr Ala
        35                  40                  45

Asp Ile Met Ser His Ile Phe Glu Val Tyr Phe Ser Asn Thr Lys Thr
    50                  55                  60

Ala Tyr Leu Gln Asp Arg Met Ala Glu Ala Leu Leu Arg Thr Cys Ile
65                  70                  75                  80

Lys Tyr Gly Gly Ile Ala Leu Glu Lys Pro Asp Asp Tyr Glu Ala Arg
                85                  90                  95

Ala Asn Leu Met Trp Ala Ser Ser Leu Ala Ile Asn Gly Leu Leu Thr
            100                 105                 110

Tyr Gly Lys Asp Thr Asn Trp Ser Val His Leu Met Glu His Glu Leu

```
                115              120                125
    Ser Ala Tyr Tyr Asp Ile Thr His Gly Val Gly Leu Ala Ile Leu Thr
    130                 135                 140
    Pro Asn Trp Met Glu Tyr Ile Leu Asn Asn Asp Thr Val Tyr Lys Phe
145                 150                 155                 160
    Val Glu Tyr Gly Val Asn Val Trp Gly Ile Asp Lys Glu Lys Asn His
                    165                 170                 175
    Tyr Asp Ile Ala His Gln Ala Ile Gln Lys Thr Arg Asp Tyr Phe Val
                180                 185                 190
    Asn Val Leu Gly Leu Pro Ser Arg Leu Arg Asp Val Gly Ile Glu Glu
                195                 200                 205
    Glu Lys Leu Asp Ile Met Ala Lys Glu Ser Val Lys Leu Thr Gly Gly
            210                 215                 220
    Thr Ile Gly Asn Leu Arg Pro Val Asn Ala Ser Glu Val Leu Gln Ile
    225                 230                 235                 240
    Phe Lys Lys Ser Val
                    245

<210> SEQ ID NO 19
<211> LENGTH: 387
<212> TYPE: PRT
<213> ORGANISM: Escherichia coli

<400> SEQUENCE: 19

Met Asn Asn Phe Asn Leu His Thr Pro Thr Arg Ile Leu Phe Gly Lys
    1               5                   10                  15
    Gly Ala Ile Ala Gly Leu Arg Glu Gln Ile Pro His Asp Ala Arg Val
                    20                  25                  30
    Leu Ile Thr Tyr Gly Gly Gly Ser Val Lys Lys Thr Gly Val Leu Asp
                35                  40                  45
    Gln Val Leu Asp Ala Leu Lys Gly Met Asp Val Leu Glu Phe Gly Gly
        50                  55                  60
    Ile Glu Pro Asn Pro Ala Tyr Glu Thr Leu Met Asn Ala Val Lys Leu
    65                  70                  75                  80
    Val Arg Glu Gln Lys Val Thr Phe Leu Leu Ala Val Gly Gly Gly Ser
                    85                  90                  95
    Val Leu Asp Gly Thr Lys Phe Ile Ala Ala Ala Ala Asn Tyr Pro Glu
                100                 105                 110
    Asn Ile Asp Pro Trp His Ile Leu Gln Thr Gly Gly Lys Glu Ile Lys
                115                 120                 125
    Ser Ala Ile Pro Met Gly Cys Val Leu Thr Leu Pro Ala Thr Gly Ser
    130                 135                 140
    Glu Ser Asn Ala Gly Ala Val Ile Ser Arg Lys Thr Thr Gly Asp Lys
145                 150                 155                 160
    Gln Ala Phe His Ser Ala His Val Gln Pro Val Phe Ala Val Leu Asp
                    165                 170                 175
    Pro Val Tyr Thr Tyr Thr Leu Pro Pro Arg Gln Val Ala Asn Gly Val
                180                 185                 190
    Val Asp Ala Phe Val His Thr Val Glu Gln Tyr Val Thr Lys Pro Val
                195                 200                 205
    Asp Ala Lys Ile Gln Asp Arg Phe Ala Glu Gly Ile Leu Leu Thr Leu
            210                 215                 220
    Ile Glu Asp Gly Pro Lys Ala Leu Lys Glu Pro Glu Asn Tyr Asp Val
    225                 230                 235                 240
```

```
Arg Ala Asn Val Met Trp Ala Ala Thr Gln Ala Leu Asn Gly Leu Ile
            245                 250                 255
Gly Ala Gly Val Pro Gln Asp Trp Ala Thr His Met Leu Gly His Glu
        260                 265                 270
Leu Thr Ala Met His Gly Leu Asp His Ala Gln Thr Leu Ala Ile Val
    275                 280                 285
Leu Pro Ala Leu Trp Asn Glu Lys Arg Asp Thr Lys Arg Ala Lys Leu
290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
        355                 360                 365
Gly Glu Asn His Asp Ile Thr Leu Asp Val Ser Arg Arg Ile Tyr Glu
    370                 375                 380
Ala Ala Arg
385

<210> SEQ ID NO 20
<211> LENGTH: 7546
<212> TYPE: DNA
<213> ORGANISM: Artificial Sequence
<220> FEATURE:
<223> OTHER INFORMATION: pATh-LEM-14

<400> SEQUENCE: 20 tcgactttt  aacaaaatat  attgataaaa  ataataatag  tgggtataat  taagttgtta      60
gagaaaacgt  ataaattagg  gataaactat  ggaacttatg  aaatagattg  aaatggttta    120
tctgttaccc  cgtaggatcc  aggaggttag  ttagaatgaa  agaagttgta  atagctagtg    180
cagtaagaac  agcgattgga  tcttatggaa  agtctcttaa  ggatgtacca  gcagtagatt    240
taggagctac  agctataaag  gaagcagtta  aaaaagcagg  aataaaacca  gaggatgtta    300
atgaagtcat  tttaggaaat  gttcttcaag  caggtttagg  acagaatcca  gcaagacagg    360
catctttttaa agcaggatta ccagttgaaa ttccagctat gactattaat aaggtttgtg    420
gttcaggact tagaacagtt agcttagcag cacaaattat aaaagcagga gatgctgacg    480
taataatagc aggtggtatg gaaaatatgt ctagagctcc ttacttagcg aataacgcta    540
gatggggata tagaatggga aacgctaaat ttgttgatga aatgatcact gacggattgt    600
gggatgcatt taatgattac cacatgggaa taacagcaga aaacatagct gagagatgga    660
acatttcaag agaagaacaa gatgagtttg ctcttgcatc acaaaaaaaa gctgaagaag    720
ctataaaatc aggtcaattt aaagatgaaa tagttcctgt agtaattaaa ggcagaaagg    780
gagaaactgt agttgataca gatgagcacc ctagatttgg atcaactata gaaggacttg    840
caaaattaaa acctgccttc aaaaagatg gaacagttac agctggtaat gcatcaggat    900
taatgactg tgcagcagta cttgtaatca tgagtgcaga aaaagctaaa gagcttggag    960
taaaaccact tgctaagata gtttcttatg gttcagcagg agttgaccca gcaataatgg   1020
gatatggacc tttctatgca acaaaagcag ctattgaaaa agcaggttgg acagttgatg   1080
aattagattt aatagaatca aatgaagctt ttgcagctca aagtttagca gtagcaaaag   1140
atttaaaatt tgatatgaat aaagtaaatg taaatggagg agctattgcc cttggtcatc   1200
```

```
caattggagc atcaggtgca agaatactcg ttactcttgt acacgcaatg caaaaaagag   1260
atgcaaaaaa aggcttagca actttatgta taggtggcgg acaaggaaca gcaatattgc   1320
tagaaaagtg ctagggccgg ccaaagtatt gttaaaaagg gaggtctgtt taatgagtat   1380
taaaagtgta gcggttttag gtagtggaac tatgtctcgt ggaattgtgc aggcttttgc   1440
agaagcaggt atagatgtaa ttatccgtgg aagaactgaa ggtagtattg gaaaaggtct   1500
agcagcagta aagaaagctt atgataaaaa agtatcaaag gggaaaattt cccaggaaga   1560
tgctgataaa atagttggaa gagtaagtac aacaactgaa cttgaaaaat tggctgattg   1620
tgatcttata atagaagcag catcagagga tatgaatata aagaaagact attttggaaa   1680
attagaagaa atatgcaagc ctgaaacaat ttttgctact aatacttctt cattatctat   1740
aactgaagta gcaacagcta caaagagacc agataaattc ataggaatgc atttctttaa   1800
tccagcaaat gttatgaaat tagttgaaat cataagaggt atgaatactt cacaagaaac   1860
ttttgatatt ataaaagaag cttccattaa aataggaaaa actcctgtag aagttgcaga   1920
agctccagga tttgttgtaa acaagatatt agtaccaatg atcaatgaag cagtaggaat   1980
tttggcagaa ggaatagctt cagcagaaga tatcgataca gctatgaaat taggcgctaa   2040
tcacccaatg ggtcctttag cattaggaga tcttattgga cttgatgtag ttcttgcagt   2100
tatggatgta ctttatagtg aaactggaga ttcaaaatat agagctcata cattacttag   2160
aaaatatgta agagcaggat ggcttggaag aaaatcagga aaaggattct tcgcttatta   2220
attaattaag tttacaagaa tggcgcttta ggaggattag tcatggaatt taaaaatatc   2280
attcttgaaa aggatggaaa tgtggcttca ataacgttga atagacctaa ggcattaaat   2340
gcattaaatg cagcaacttt aaaagagata gatgccgcaa taaacgacat tgctgaagat   2400
gataacgtat atgctgtgat aattactggg tcaggtaaag cttttgtagc aggagcagat   2460
atagctgaga tgaaagatct tactgcagtt gagggaagaa agttttcagt tcttggcaat   2520 aaaatatttta gaaaattaga aaatttagaa aaaccagtta tagcagctat aaatggattt   2580
gcactgggtg gtggctgtga attgtcattg tcttgcgata taagaatagc ttcatcaaag   2640
gctaagtttg gtcaaccaga ggttggtctt ggaattactc cagggtttgg aggtactcaa   2700
agacttgcaa gagcaatagg cgttggtatg ctaaggaac ttatatatac cggaaaagta   2760
attaatgctg aagaggcatt aagaataggt ttggtaaata agtagttga gccagataaa   2820 ttattggaag aagctaaagc tttagtagat gctattattg ttaatgcacc tatagctgtt   2880
agaatgtgta aggctgctat aaatcaagga cttcagtgtg atatagatac aggtgtagct   2940
tatgaagcag aagtatttgg ggaatgtttt gctacagaag atagagtaga aggaatgaca   3000
gcatttgtag aaaaaagaga caaggctttt aaaaataagt aaaccggtga ggtaagttta   3060
tatggatttt acattaacaa acgagcaaaa atttgtagaa caaatggtaa gtgaatttac   3120
tgaaaatgaa gttaaaccta tagctgctga aatagatgaa acagaaaggt ttcctcttga   3180
gacagtagaa aaatttgcta atacggaat gatgggtatg cctttccag ttgaatacgg   3240 cggctcaggt acagattatt tatcctatat aatagcagta gaaggacttg caaagagttg   3300
tacttcatca tcaactatat tgtcagcaca tacttcactt tgtgcagcac ctattttatga   3360 ttggggtaca gaagaacaga acaaaaata cttagttcct cttgcaaagg gagaaaaact   3420
tggagcattt ggtttaactg aacctaatgc aggtactgat gctgctggac agcagacaac   3480
agctgtttta gaaggggatc attatgtatt aaatggacaa aaaatatttta ttacaaatgg   3540
```

```
tgcatatgca gatactttg  taatatttgc aatgacagac agaagcaagg gtacaagagg   3600
aataacagca tttatagttg aaaaagattt ccctggtttc tccataggaa aatctgaaga   3660
taagttggga attagagctt cctcaactac agaacttata tttgagaatt gcatagttcc   3720
aaaagaaaat atgttaggaa aagaaggaaa aggatttact gtagcaatgc atactcttga   3780
tggaggaaga attggtatag cagcacaagc gttaggttta gcagaaggcg cattagctga   3840
agcacttaat tatatgaaag aaagaaaaca atttggaaaa gctctttaca aattccaggg   3900
attagcatgg atggttgcag aattagatac taaaatagaa gctgttaaac aacttgttta   3960
taaagcagca gtaaataaac aaatgggtct tccatattca gtggaagctg caagagctaa   4020
attagctgcg gctactgtag ctatggaaac aactactaaa gttgttcaaa tctttggtgg   4080
atatggattc actaaggatt atccagtaga aagaatgatg agagatgcta agataactga   4140
aatatatgaa ggaacttcac aagtacaaaa gatggttatt tcagcaaatt tatttaaata   4200
aatttaaatt ttaaggggcg cctaccccgt aggatccagg aggttagtta aatgaaaat    4260 agtagtttgc ttaaagcaag taccagatac aactgaagtt aaaatagatc caaaacagg    4320 aacattaata agagaaggcg ttccatcaat aataaaccca gatgataaaa atgcacttga   4380
agaatcaatt gctttaaaag aaaaagtagg gggtacagtt acagtagtaa gcatgggcc    4440 tccacaggca gtggatgcac ttagagaagc tctagctatg ggagctgatg aagcaatatt   4500
agtttcagac agagcttttg caggagcaga tactcaagct acttcctatg cattagcagg   4560
agcacttaaa aatttagaat atgatttaat atttgcagga agacaagcta tagatggaga   4620
tactgcacag gttggacctc aaatagcaga aaaattagga atacctcaga taacatatgt   4680
agaaaaagtt gatgtagatg gagatacttt aacagttcaa agagcttggg aagatggata   4740
tgaagtagca aaaattaaaa ctccatgcat gttaactgct ataaaagagt taaatcaacc   4800
aagatatatg aacatgaaga acatatttga agttttcaag aaagaagtta aatatggag    4860 tgctgacgac ttagatgtag ataaaaataa acttggtctt aatggttcct gcacaaaagt   4920
taagagatca catacaaaag aagcaaaagg agcaggagaa atcgttaata aaccaataaa   4980
agaagcagta gcatattcaa tttcaaaatt aagagaaaaa catgtcattt aatatatagg   5040
aggggtttag aatgaactta gcagaataca aaggcgtatg ggtatttgct gaacaaaggg   5100
atggagaact acaaaaagta gcacttcaat tagttggaaa aggaagagaa ttggcagaca   5160
ctttaggagt agaattaact gctgtattac ttggtagtga agtagatgat ttggcaaaag   5220
aattagttgc atatggagca gacaatgttt tatacgcaga tagtcctctt ttaaaacatt   5280
atactacaga tggatacact aaagtaatag atgaacttat aaaagaaaga aaaccagaaa   5340
tattacttat aggagctaca tttatcggaa gagacttagg accaagagtt gcaggtagag   5400 ttttttacagg tcttacagca gactgtacag gacttgatat agatgaggca acaaaaaatt   5460
tgatgatgac aagacctgca tttggtggaa acttaatggc aactatagct tgcgaaaaaa   5520
caagacctca aatgtcaaca gtaagaccag agttttttaa tgcgcttcca agagatgctt   5580
caagaactgg aaaaatagaa aaaatagctg caaatgttgc aaaagatgac atcagaattg   5640
aagtgcttga agtagttaaa tctgctggcg atacaataga tatttcagaa gcagatgtaa   5700
ttgtatcagg tggaagagga cttggtggtc cagatggatt caagttctt  aaagaattag   5760 cagatttatt aggtggaact ataggtggat cccgtgcaac tatagatgct ggctggatag   5820
ataagagcta tcaggttgga caaactggta aaacagtaag accaggtctt tatattgcat   5880
gcggaatatc aggtcaaata caacatttag ctggtatgca ggatagtgga tttatcgtag   5940
```

```
ctatcaataa agatgaaaac gctccaatga tgcaagtagc ggatcttgca attgtaggag      6000
atttatataa ggttgttcca gaatttgtag aacaagttaa agctttaaat ctttaaggta      6060
ccccgtagga tccaggaggt tagttagaat ggttttttaaa aattggcagg atctttataa     6120
aagtaaaatt gttagtgcag acgaagctgt atctaaagta agctgtggag atagcataat      6180
tttaggcaat gcttgtggag catctcttac acttttagat gccttggctg caaataagga      6240
aaagtataag agtgtaaaga tacacaatct tatacttaat tataaaaatg atatatatac      6300
tgatccggaa tcagaaaagt atattcatgg aaatactttc tttgtaagtg gaggtacaaa      6360
ggaagcagtt aattgtaata gaacagatta tactccatgc tttttttatg aaataccaaa      6420
attattaaaa caaaagtata taaatgcaga tgtagctttt attcaagtaa gtaagcctga      6480
tagccatgga tactgtagct ttggagtatc aaccgattat tcacaggcaa tggtacagtc      6540
tgcaaagctt ataattgcag aagtaaacga tcagatgcca agagttttag gagacaattt      6600
tatacacatt tctgatatgg attacatagt agaaagttca cgtccaattc tagaattgac      6660
tcctcctaaa ataggagaag tagagaagac aataggaaaa tactgtgcat ctcttgtaga      6720
agatggttct acacttcagc ttggaatagg agctattcca gatgcagtac ttttattctt      6780
gaaggataaa aaggatttgg gtatacattc agaaatgata tccgatggtg ttgttgaatt      6840
agttgaagca ggggtaatta caaataagaa aaagtcccct catccaggaa aaataattat      6900
tacattctta atgggaacta gaaaattata tgatttcata aatgataatc ctatggtaga      6960
aggataccct gtagattatg taaatgatcc taaggttatt atgcaaaatt ctaagatggt      7020
atgtataaac tcctgtgtag aagtggattt cacaggacaa gtgtgtgctg aaagtgtagg      7080
atttaaacaa ataagcggtg taggtggaca agttgattac atgagaggag ctagcatggc      7140
tgatggagga aaatcaattc ttgctatacc atctactgca gctggcggca aaatttcaag      7200
aatagttcct attttaactg aaggagcggg ggttactact tcaagatatg atgttcaata      7260
tgttgttaca gaatatggta ttgcacttct caagggcaaa tccataagag aaagagctaa      7320
ggagcttata aaaattgcac atcctaaatt tagggaagaa ttaacagctc aatttgaaaa      7380
aagattcagt tgtaagcttt aaacttaatg atttgccagt aaaagagatt gtttctagct      7440
ctcacattct tgcagatata atattgccta gagctgaagt tatatatgat tatcttaagt      7500
aataaaaata agagttacct taaatggtaa ctcttatttt tttaat                    7546
```

<210> SEQ ID NO 21
<211> LENGTH: 4832
<212> TYPE: DNA
<213> ORGANISM: Artificial Sequence
<220> FEATURE:
<223> OTHER INFORMATION: pATh-LEM-23

<400> SEQUENCE: 21

```
ggcatttgtc aactatagat ggtgaacctc tttgcacgaa gttaccactc ataactgcta        60
ttacagcatc acattttgta gcagaacgag cactttcaat atgatattta tgtccattgt       120
gaaagggatt atattcaact attattccag ttacgttcat agaaattttc ctttctaaaa       180
tattttattc catgtcaaga actctgttta tttcattaaa gaactataag tacaaagtat       240
agggcatttg aaaaaatagg ctagtatatt gattgattat ttattttaaa atgcctaagt       300
gaaatatata catattataa caataaaata agtattagtg taggattttt aaatagagta       360 tctatttca gattaaattt ttgcttattt gatttacatt atataatatt gagtaaagta        420
```

```
ttgactagca aaattttttg atactttaat ttgtgaaatt tcttatcaaa agttatattt    480
ttgaatgatt tttattgaaa aatacaacta aaaaggatta tagtataagt gtgtgtaatt    540
ttgtgttaaa tttaaaggat ccaggaggtt agttagaatg gaatttaaaa atatcattct    600
tgaaaaggat ggaaatgtgg cttcaataac gttgaataga cctaaggcat taaatgcatt    660
aaatgcagca actttaaaag agatagatgc cgcaataaac gacattgctg aagatgataa    720
cgtatatgct gtgataatta ctgggtcagg taaagctttt gtagcaggag cagatatagc    780
tgagatgaaa gatcttactg cagttgaggg aagaaagttt tcagttcttg gcaataaaat    840
atttagaaaa ttagaaaatt tagaaaaacc agttatagca gctataaatg gatttgcact    900
gggtggtggc tgtgaattgt cattgtcttg cgatataaga atagcttcat caaaggctaa    960
gtttggtcaa ccagaggttg gtcttggaat tactccaggg tttggaggta ctcaaagact   1020
tgcaagagca ataggcgttg gtatggctaa ggaacttata tataccggaa aagtaattaa   1080
tgctgaagag gcattaagaa taggtttggt aaataaagta gttgagccag ataaattatt   1140
ggaagaagct aaagctttag tagatgctat tattgttaat gcacctatag ctgttagaat   1200
gtgtaaggct gctataaatc aaggacttca gtgtgatata gatacaggtg tagcttatga   1260
agcagaagta tttggggaat gttttgctac agaaagataga gtagaaggaa tgacagcatt   1320
tgtagaaaaa agagacaagg cttttaaaaa taagtaaggc cggccaaagt attgttaaaa   1380
agggaggtct gtttaatgag tattaaaagt gtagcggttt taggtagtgg aactatgtct   1440
cgtggaattg tgcaggcttt tgcagaagca ggtatagatg taattatccg tggaagaact   1500
gaaggtagta ttggaaaagg tctagcagca gtaaagaaag cttatgataa aaaagtatca   1560
aaggggaaaa tttcccagga agatgctgat aaaatagttg gaagagtaag tacaacaact   1620
gaacttgaaa aattggctga ttgtgatctt ataatagaag cagcatcaga ggatatgaat   1680
ataaagaaag actattttgg aaaattagaa gaaatatgca agcctgaaac aattttttgct  1740 actaatactt cttcattatc tataactgaa gtagcaacag ctacaaagag accagataaa   1800
ttcataggaa tgcatttctt taatccagca aatgttatga aattagttga aatcataaga   1860
ggtatgaata cttcacaaga aacttttgat attataaaag aagcttccat taaaatagga   1920
aaaactcctg tagaagttgc agaagctcca ggatttgttg taaacaagat attagtacca   1980
atgatcaatg aagcagtagg aattttggca gaaggaatag cttcagcaga agatatcgat   2040
acagctatga aattaggcgc taatcaccca atgggtcctt tagcattagg agatcttatt   2100
ggacttgatg tagttcttgc agttatggat gtactttata gtgaaactgg agattcaaaa   2160
tatagagctc atacattact tagaaaatat gtaagagcag gatggcttgg aagaaaatca   2220
ggaaaaggat tcttcgctta ttaattaatt aagtttacaa gaatggcgct ttaggaggat   2280
tagtcatgaa agaagttgta atagctagtg cagtaagaac agcgattgga tcttatggaa   2340
agtctcttaa ggatgtacca gcagtagatt taggagctac agctataaag gaagcagtta   2400
aaaaagcagg aataaaacca gaggatgtta atgaagtcat tttaggaaat gttcttcaag   2460
caggtttagg acagaatcca gcaagacagg catcttttaa agcaggatta ccagttgaaa   2520
ttccagctat gactattaat aaggtttgtg gttcaggact tagaacagtt agcttagcag   2580
cacaaattat aaaagcagga gatgctgacg taataatagc aggtggtatg gaaaatatgt   2640
ctagagctcc ttacttagcg aataacgcta gatgggggata tagaatggga aacgctaaat   2700
ttgttgatga aatgatcact gacgattgt gggatgcatt taatgattac cacatgggaa    2760
taacagcaga aaacatagct gagagatgga acatttcaag agaagaacaa gatgagtttg   2820
```

```
ctcttgcatc acaaaaaaaa gctgaagaag ctataaaatc aggtcaattt aaagatgaaa    2880
tagttcctgt agtaattaaa ggcagaaagg gagaaactgt agttgataca gatgagcacc    2940
ctagatttgg atcaactata gaaggacttg caaaattaaa acctgccttc aaaaaagatg    3000
gaacagttac agctggtaat gcatcaggat taaatgactg tgcagcagta cttgtaatca    3060
tgagtgcaga aaaagctaaa gagcttggag taaaaccact tgctaagata gtttcttatg    3120
gttcagcagg agttgaccca gcaataatgg gatatgacc tttctatgca acaaaagcag     3180
ctattgaaaa agcaggttgg acagttgatg aattagattt aatagaatca aatgaagctt    3240
ttgcagctca aagtttagca gtagcaaaag atttaaaatt tgatatgaat aaagtaaatg    3300
taaatggagg agctattgcc cttggtcatc caattggagc atcaggtgca agaatactcg    3360
ttactcttgt acacgcaatg caaaaaagag atgcaaaaaa aggcttagca actttatgta    3420
taggtggcgg acaaggaaca gcaatattgc tagaaaagtg ctaggaggta agtttatggc    3480
gcctaccccg taggatccag gaggttagtt agaatggttt ttaaaaattg gcaggatctt    3540
tataaaagta aaattgttag tgcagacgaa gctgtatcta aagtaagctg tggagatagc    3600
ataattttag gcaatgcttg tggagcatct cttacacttt tagatgcctt ggctgcaaat    3660
aaggaaaagt ataagagtgt aaagatacac aatcttatac ttaattataa aaatgatata    3720
tatactgatc cggaatcaga aaagtatatt catggaaata cttctcttgt aagtggaggt    3780
acaaaggaag cagttaattg taatagaaca gattatactc catgcttttt ttatgaaata    3840
ccaaaattat aaaacaaaa gtatataaat gcagatgtag cttttattca agtaagtaag     3900
cctgatagcc atggatactg tagctttgga gtatcaaccg attattcaca ggcaatggta    3960
cagtctgcaa agcttataat tgcagaagta aacgatcaga tgccaagagt tttaggagac    4020
aattttatac acatttctga tatggattac atagtagaaa gttcacgtcc aattctagaa    4080
ttgactcctc ctaaaatagg agaagtagag aagacaatag gaaaatactg tgcatctctt    4140
gtagaagatg gttctacact tcagcttgga ataggagcta ttccagatgc agtacttttta    4200 ttcttgaagg ataaaaagga tttgggtata cattcagaaa tgatatccga tggtgttgtt    4260
gaattagttg aagcagggt aattacaaat aagaaaaagt cccttcatcc aggaaaaata    4320
attattacat tcttaatggg aactaagaaa ttatatgatt tcataaatga taatcctatg    4380
gtagaaggat accctgtaga ttatgtaaat gatcctaagg ttattatgca aaattctaag    4440
atggtatgta taaactcctg tgtagaagtg gatttcacag gacaagtgtg tgctgaaagt    4500 gtaggatta aacaaataag cggtgtaggt ggacaagttg attacatgag aggagctagc    4560
atggctgatg gaggaaaatc aattcttgct ataccatcta ctgcagctgg cggcaaaatt    4620
tcaagaatag ttcctatttt aactgaagga gcgggggtta ctacttcaag atatgatgtt    4680
caatatgttg ttacagaata tggtattgca cttctcaagg gcaaatccat aagagaaaga    4740
gctaaggagc ttataaaaat tgcacatcct aaatttaggg aagaattaac agctcaattt    4800
gaaaaaagat tcagttgtaa gctttaagcg at                                  4832
```

<210> SEQ ID NO 22
<211> LENGTH: 4255
<212> TYPE: DNA
<213> ORGANISM: Artificial Sequence
<220> FEATURE:
<223> OTHER INFORMATION: pATH-LEM-24

<400> SEQUENCE: 22

```
atggaattta aaaatatcat tcttgaaaag gatggaaatg tggcttcaat aacgttgaat    60
agacctaagg cattaaatgc attaaatgca gcaactttaa aagagataga tgccgcaata   120
aacgacattg ctgaagatga taacgtatat gctgtgataa ttactgggtc aggtaaagct   180
tttgtagcag gagcagatat agctgagatg aaagatctta ctgcagttga gggaagaaag   240
ttttcagttc ttggcaataa aatatttaga aaattagaaa atttagaaaa accagttata   300
gcagctataa atggatttgc actgggtggt ggctgtgaat tgtcattgtc ttgcgatata   360
agaatagctt catcaaaggc taagtttggt caaccagagg ttggtcttgg aattactcca   420
gggtttggag gtactcaaag acttgcaaga gcaataggcg ttggtatggc taaggaactt   480
atatataccg gaaaagtaat taatgctgaa gaggcattaa gaataggttt ggtaaataaa   540
gtagttgagc cagataaatt attggaagaa gctaaagctt tagtagatgc tattattgtt   600
aatgcaccta tagctgttag aatgtgtaag gctgctataa atcaaggact tcagtgtgat   660
atagatacag gtgtagctta tgaagcagaa gtatttgggg aatgttttgc tacagaagat   720
agagtagaag gaatgacagc atttgtagaa aaaagagaca aggcttttaa aaataagtaa   780
ggccggccaa agtattgtta aaagggagg tctgtttaat gagtattaaa agtgtagcgg   840
ttttaggtag tggaactatg tctcgtggaa ttgtgcaggc ttttgcagaa gcaggtatag   900
atgtaattat ccgtggaaga actgaaggta gtattggaaa aggtctagca gcagtaaaga   960
aagcttatga taaaaagta tcaaggggaa aaatttccca ggaagatgct gataaaatg   1020 ttggaagagt aagtacaaca actgaacttg aaaaattggc tgattgtgat cttataatag  1080
aagcagcatc agaggatatg aatataaaga aagactattt tggaaaatta gaagaaatat  1140
gcaagcctga acaattttt gctactaata cttcttcatt atctataact gaagtagcaa   1200
cagctacaaa gagaccagat aaattcatag gaatgcattt cttaatcca gcaaatgtta   1260 tgaaattagt tgaaatcata agaggtatga atacttcaca gaaacttttt gatattataa  1320
aagaagcttc cattaaaata ggaaaaaactc ctgtagaagt tgcagaagct ccaggatttg  1380
ttgtaaacaa gatattagta ccaatgatca atgaagcagt aggaattttg gcagaaggaa  1440
tagcttcagc agaagatatc gatacagcta tgaaattagg cgctaatcac ccaatgggtc  1500
ctttagcatt aggagatctt attggacttg atgtagttct tgcagttatg gatgtacttt  1560
atagtgaaac tggagattca aaatatagag ctcatacatt acttagaaaa tatgtaagag  1620
caggatggct tggaagaaaa tcaggaaaag gattcttcgc ttattaatta ttaagttta   1680 caagaatggc gctttaggag gattagtcat gaaagaagtt gtaatagcta gtgcagtaag  1740
aacagcgatt ggatcttatg gaaagtctct taaggatgta ccagcagtag atttaggagc  1800
tacagctata aaggaagcag ttaaaaaagc aggaataaaa ccagaggatg ttaatgaagt  1860 catttttagga aatgttcttc aagcaggttt aggacagaat ccagcaagac aggcatcttt  1920
taaagcagga ttaccagttg aaattccagc tatgactatt aataaggttt gtggttcagg  1980
acttagaaca gttagcttag cagcacaaat tataaaagca ggagatgctg acgtaataat  2040
agcaggtggt atggaaaata tgtctagagc tccttactta gcgaataacg ctagatgggg  2100
atatagaatg ggaaacgcta aatttgttga tgaaatgatc actgacggat gtgggatgc   2160 atttaatgat taccacatgg gaataacagc agaaaacata gctgagagat ggaacatttc  2220
aagagaagaa caagatgagt ttgctcttgc atcacaaaaa aaagctgaag aagctataaa  2280
atcaggtcaa tttaaagatg aaatagttcc tgtagtaatt aaaggcagaa agggagaaac  2340
tgtagttgat acagatgagc accctagatt tggatcaact atagaaggac ttgcaaaatt  2400
```

```
aaaacctgcc ttcaaaaaag atggaacagt tacagctggt aatgcatcag gattaaatga    2460
ctgtgcagca gtacttgtaa tcatgagtgc agaaaaagct aaagagcttg gagtaaaacc    2520
acttgctaag atagtttctt atggttcagc aggagttgac ccagcaataa tgggatatgg    2580
acctttctat gcaacaaaag cagctattga aaaagcaggt tggacagttg atgaattaga    2640
tttaatagaa tcaaatgaag cttttgcagc tcaaagttta gcagtagcaa aagatttaaa    2700
atttgatatg aataaagtaa atgtaaatgg aggagctatt gcccttggtc atccaattgg    2760
agcatcaggt gcaagaatac tcgttactct tgtacacgca atgcaaaaaa gagatgcaaa    2820
aaaaggctta gcaactttat gtataggtgg cggacaagga acagcaatat tgctagaaaa    2880
gtgctaggag gtaagtttat ggcgcctacc ccgtaggatc caggaggtta gttagaatgg    2940 ttttttaaaaa ttggcaggat ctttataaaa gtaaaattgt tagtgcagac gaagctgtat    3000
ctaaagtaag ctgtggagat agcataattt taggcaatgc ttgtggagca tctcttacac    3060
ttttagatgc cttggctgca aataaggaaa agtataagag tgtaaagata cacaatctta    3120
tacttaatta taaaaatgat atatatactg atccggaatc agaaaagtat attcatggaa    3180
atactttctt tgtaagtgga ggtacaaagg aagcagttaa ttgtaataga acagattata    3240
ctccatgctt tttttatgaa ataccaaaat tattaaaaca aaagtatata aatgcagatg    3300
tagcttttat tcaagtaagt aagcctgata gccatggata ctgtagcttt ggagtatcaa    3360
ccgattattc acaggcaatg gtacagtctg caaagcttat aattgcagaa gtaaacgatc    3420
agatgccaag agttttagga gacaattta tacacatttc tgatatggat tacatagtag    3480
aaagttcacg tccaattcta gaattgactc ctcctaaaat aggagaagta gagaagacaa    3540
taggaaaata ctgtgcatct cttgtagaag atggttctac acttcagctt ggaataggag    3600
ctattccaga tgcagtactt ttattcttga aggataaaaa ggatttgggt atacattcag    3660
aaatgatatc cgatggtgtt gttgaattag ttgaagcagg ggtaattaca aataagaaaa    3720
agtcccttca tccaggaaaa ataattatta cattcttaat gggaactaag aaattatatg    3780
atttcataaa tgataatcct atggtagaag ataccctgt agattatgta aatgatccta    3840
aggttattat gcaaaattct aagatggtat gtataaactc ctgtgtagaa gtggatttca    3900
caggacaagt gtgtgctgaa agtgtaggat ttaaacaaat aagcggtgta ggtggacaag    3960
ttgattacat gagaggagct agcatggctg atggaggaaa atcaattctt gctataccat    4020
ctactgcagc tggcggcaaa atttcaagaa tagttcctat tttaactgaa ggagcggggg    4080
ttactacttc aagatatgat gttcaatatg ttgttacaga atatggtatt gcacttctca    4140
agggcaaatc cataagagaa agagctaagg agcttataaa aattgcacat cctaaattta    4200
gggaagaatt aacagctcaa tttgaaaaaa gattcagttg taagctttaa gcgat         4255
```

<210> SEQ ID NO 23
<211> LENGTH: 4255
<212> TYPE: DNA
<213> ORGANISM: Artificial Sequence
<220> FEATURE:
<223> OTHER INFORMATION: pATh-LEM-25

<400> SEQUENCE: 23

```
atggaattta aaaatatcat tcttgaaaag gatggaaatg tggcttcaat aacgttgaat       60
agacctaagg cattaaatgc attaaatgca gcaactttaa aagagataga tgccgcaata      120
aacgacattg ctgaagatga taacgtatat gctgtgataa ttactgggtc aggtaaagct      180
```

```
tttgtagcag gagcagatat agctgagatg aaagatctta ctgcagttga gggaagaaag      240
ttttcagttc ttggcaataa aatatttaga aaattagaaa atttagaaaa accagttata      300
gcagctataa atggatttgc actgggtggt ggctgtgaat tgtcattgtc ttgcgatata      360
agaatagctt catcaaaggc taagtttggt caaccagagg ttggtcttgg aattactcca      420
gggtttggag gtactcaaag acttgcaaga gcaataggcg ttggtatggc taaggaactt      480
atatataccg gaaaagtaat taatgctgaa gaggcattaa gaataggttt ggtaaataaa      540
gtagttgagc cagataaatt attggaagaa gctaaagctt tagtagatgc tattattgtt      600
aatgcaccta tagctgttag aatgtgtaag gctgctataa atcaaggact tcagtgtgat      660
atagatacag gtgtagctta tgaagcagaa gtatttgggg aatgttttgc tacagaagat      720
agagtagaag gaatgacagc atttgtgaaa aaaagagaca aggcttttaa aaataagtaa      780
ggccggccaa agtattgtta aaagggagg tctgtttaat gagtattaaa agtgtagcgg      840
ttttaggtag tggaactatg tctcgtggaa ttgtgcaggc ttttgcagaa gcaggtatag      900
atgtaattat ccgtggaaga actgaaggta gtattggaaa aggtctagca gcagtaaaga      960
aagcttatga taaaaaagta tcaaagggga aaatttccca ggaagatgct gataaaatag     1020
ttggaagagt aagtacaaca actgaacttg aaaaattggc tgattgtgat cttataatag     1080
aagcagcatc agaggatatg aatataaaga aagactattt tggaaaatta gaagaaatat     1140
gcaagcctga aacaattttt gctactaata cttcttcatt atctataact gaagtagcaa     1200
cagctacaaa gagaccagat aaattcatag gaatgcattt ctttaatcca gcaaatgtta     1260
tgaaattagt tgaaatcata agaggtatga atacttcaca agaaactttt gatattataa     1320
aagaagcttc cattaaaata ggaaaaactc ctgtagaagt tgcagaagct ccaggatttg     1380
ttgtaaacaa gatattagta ccaatgatca atgaagcagt aggaattttg gcagaaggaa     1440
tagcttcagc agaagatatc gatacagcta tgaaattagg cgctaatcac ccaatgggtc     1500
ctttagcatt aggagatctt attggacttg atgtagttct tgcagttatg gatgtacttt     1560
atagtgaaac tggagattca aaatatagag ctcatacatt acttagaaaa tatgtaagag     1620
caggatggct tggaagaaaa tcaggaaaag gattcttcgc ttattaatta attaagttta     1680
caagaatggc gctttaggag gattagtcat gaaagaagtt gtaatagcta gtgcagtaag     1740
aacagcgatt ggatccttatg gaaagtctct taaggatgta ccagcagtag atttaggagc     1800
tacagctata aaggaagcag ttaaaaaagc aggaataaaa ccagaggatg ttaatgaagt     1860
cattttagga aatgttcttc aagcaggttt aggacagaat ccagcaagac aggcatcttt     1920
taaagcagga ttaccagttg aaattccagc tatgactatt aataaggttt gtggttcagg     1980
acttagaaca gttagcttag cagcacaaat tataaaagca ggagatgctg acgtaataat     2040
agcaggtggt atggaaaata tgtctagagc tccttactta gcgaataacg ctagatgggg     2100
atatagaatg ggaaacgcta aatttgttga tgaaatgatc actgacggat tgtgggatgc     2160
atttaatgat taccacatgg gaataacagc agaaaacata gctgagagat ggaacatttc     2220
aagagaagaa caagatgagt ttgctcttgc atcacaaaaa aaagctgaag aagctataaa     2280
atcaggtcaa tttaaagatg aaatagttcc tgtagtaatt aaaggcagaa agggagaaac     2340
tgtagttgat acagatgagc accctagatt tggatcaact atagaaggac ttgcaaaatt     2400
aaaacctgcc ttcaaaaaag atggaacagt tacagctggt aatgcatcag gattaaatga     2460
ctgtgcagca gtacttgtaa tcatgagtgc agaaaaagct aaagagcttg gagtaaaacc     2520
acttgctaag atagtttctt atggttcagc aggagttgac ccagcaataa tgggatatgg     2580
```

```
accttttctat gcaacaaaag cagctattga aaaagcaggt tggacagttg atgaattaga    2640
tttaatagaa tcaaatgaag cttttgcagc tcaaagttta gcagtagcaa aagatttaaa    2700
atttgatatg aataaagtaa atgtaaatgg aggagctatt gcccttggtt atccaattgg    2760
agcatcaggt gcaagaatac tcgttactct tgtacacgca atgcaaaaaa gagatgcaaa    2820
aaaaggctta gcaactttat gtataggtgg cggacaagga acagcaatat tgctagaaaa    2880
gtgctaggag gtaagtttat ggcgcctacc ccgtaggatc caggaggtta gttagaatgg    2940 ttttttaaaaa ttggcaggat ctttataaaa gtaaaattgt tagtgcagac gaagctgtat    3000
ctaaagtaag ctgtggagat agcataattt taggcaatgc ttgtggagca tctcttacac    3060
ttttagatgc cttggctgca aataaggaaa agtataagag tgtaaagata cacaatctta    3120
tacttaatta taaaaatgat atatatactg atccggaatc agaaaagtat attcatggaa    3180
atactttctt tgtaagtgga ggtacaaagg aagcagttaa ttgtaataga acagattata    3240
ctccatgctt tttttatgaa ataccaaaat tattaaaaca aaagtatata aatgcagatg    3300
tagcttttat tcaagtaagt aagcctgata gccatggata ctgtagcttt ggagtatcaa    3360
ccgattattc acaggcaatg gtacagtctg caaagcttat aattgcagaa gtaaacgatc    3420
agatgccaag agttttagga gacaatttta tacacatttc tgatatggat tacatagtag    3480
aaagttcacg tccaattcta gaattgactc ctcctaaaat aggagaagta gagaagacaa    3540
taggaaaata ctgtgcatct cttgtagaag atggttctac acttcagctt ggaataggag    3600
ctattccaga tgcagtactt ttattcttga aggataaaaa ggatttgggt atacattcag    3660
aaatgatatc cgatggtgtt gttgaattag ttgaagcagg ggtaattaca aataagaaaa    3720
agtcccttca tccaggaaaa ataattatta cattcttaat gggaactaag aaattatatg    3780
atttcataaa tgataatcct atggtagaag ataccctgt agattatgta aatgatccta    3840
aggttattat gcaaaattct aagatggtat gtataaactc ctgtgtagaa gtggatttca    3900
caggacaagt gtgtgctgaa agtgtaggat ttaaacaaat aagcggtgta ggtggacaag    3960
ttgattacat gagaggagct agcatggctg atggaggaaa atcaattctt gctataccat    4020
ctactgcagc tggcggcaaa atttcaagaa tagttcctat tttaactgaa ggagcggggg    4080
ttactacttc aagatatgat gttcaatatg ttgttacaga atatggtatt gcacttctca    4140
agggcaaatc cataagagaa agagctaagg agcttataaa aattgcacat cctaaattta    4200
gggaagaatt aacagctcaa tttgaaaaaa gattcagttg taagctttaa gcgat        4255
```

<210> SEQ ID NO 24
<211> LENGTH: 4255
<212> TYPE: DNA
<213> ORGANISM: Artificial Sequence
<220> FEATURE:
<223> OTHER INFORMATION: pATh-LEM-26

<400> SEQUENCE: 24

```
atggaattta aaaatatcat tcttgaaaag gatggaaatg tggcttcaat aacgttgaat    60
agacctaagg cattaaatgc attaaatgca gcaactttaa aagagataga tgccgcaata    120
aacgacattg ctgaagatga taacgtatat gctgtgaata ttactgggtc aggtaaagct    180
tttgtagcag gagcagatat agctgagatg aaagatctta ctgcagttga gggaagaaag    240
ttttcagttc ttggcaataa aatatttaga aaattagaaa atttagaaaa accagttata    300
gcagctataa atggatttgc actgggtggt ggctgtgaat tgtcattgtc ttgcgatata    360
```

```
agaatagctt catcaaaggc taagtttggt caaccagagg ttggtcttgg aattactcca      420
gggtttggag gtactcaaag acttgcaaga gcaataggcg ttggtatggc taaggaactt      480
atatataccg gaaaagtaat taatgctgaa gaggcattaa gaataggttt ggtaaataaa      540
gtagttgagc cagataaatt attggaagaa gctaaagctt tagtagatgc tattattgtt      600
aatgcaccta tagctgttag aatgtgtaag gctgctataa atcaaggact tcagtgtgat      660
atagatacag gtgtagctta tgaagcagaa gtatttgggg aatgttttgc tacagaagat      720
agagtagaag gaatgacagc atttgtagaa aaaagagaca aggcttttaa aaataagtaa      780
ggccggccaa agtattgtta aaagggagg tctgtttaat gagtattaaa agtgtagcgg       840
ttttaggtag tggaactatg tctcgtggaa ttgtgcaggc ttttgcagaa gcaggtatag      900
atgtaattat ccgtggaaga actgaaggta gtattggaaa aggtctagca gcagtaaaga      960
aagcttatga taaaaaagta tcaaagggga aaatttccca ggaagatgct gataaaatag     1020
ttggaagagt aagtacaaca actgaacttg aaaaattggc tgattgtgat cttataatag     1080
aagcagcatc agaggatatg aatataaaga aagactattt tggaaaatta gaagaaatat     1140
gcaagcctga aacaattttt gctactaata cttcttcatt atctataact gaagtagcaa     1200
cagctacaaa gagaccagat aaattcatag gaatgcattt ctttaatcca gcaaatgtta     1260
tgaaattagt tgaaatcata gaggtatga atacttcaca agaaacttttt gatattataa     1320 aagaagcttc cattaaaata ggaaaaactc ctgtagaagt tgcagaagct ccaggatttg     1380
ttgtaaacaa gatattagta ccaatgatca atgaagcagt aggaattttg gcagaaggaa     1440
tagcttcagc agaagatatc gatacagcta tgaaattagg cgctaatcac ccaatgggtc     1500
ctttagcatt aggagatctt attggacttg atgtagttct tgcagttatg gatgtacttt     1560
atagtgaaac tggagattca aaatatagag ctcatacatt acttagaaaa tatgtaagag     1620
caggatggct tggaagaaaa tcaggaaaag gattcttcgc ttattaatta attaagttta     1680
caagaatggc gctttaggag gattagtcat gaaagaagtt gtaatagcta gtgcagtaag     1740
aacagcgatt ggatcttatg gaaagtctct taaggatgta ccagcagtag atttaggagc     1800
tacagctata aaggaagcag ttaaaaaagc aggaataaaa ccagaggatg ttaatgaagt     1860
cattttagga aatgttcttc aagcaggttt aggacagaat ccagcaagac aggcatcttt     1920
taaagcagga ttaccagttg aaattccagc tatgactatt aataaggttt gtggttcagg     1980
acttagaaca gttagcttag cagcacaaat tataaaagca ggagatgctg acgtaataat     2040
agcaggtggt atgaaaaata tgtctagagc tccttactta gcgaataacg ctagatgggg     2100
atatagaatg ggaaacgcta aatttgttga tgaaatgatc actgacggat gtgtgggatgc    2160 atttaatgat taccacatgg gaataacagc agaaaacata gctgagagat ggaacatttc     2220
aagagaagaa caagatgagt ttgctcttgc atcacaaaaa aaagctgaag aagctataaa     2280
atcaggtcaa tttaaagatg aaatagttcc tgtagtaatt aaaggcagaa agggagaaac     2340
tgtagttgat acagatgagc accctagatt tggatcaact atagaaggac ttgcaaaatt     2400
aaaacctgcc ttcaaaaaag atggaacagt tacagctggt aatgcatcag gattaaatga     2460
ctgtgcagca gtacttgtaa tcatgagtgc agaaaaagct aaagagcttg gagtaaaacc     2520
acttgctaag atagtttctt atggttcagc aggagttgac ccagcaataa tgggatatgg     2580 accttttctat gcaacaaaag cagctattga aaaagcaggt tggacagttg atgaattaga     2640
tttaatagaa tcaaatgaag cttttgcagc tcaaagttta gcagtagcaa aagatttaaa     2700
atttgatatg aataaagtaa atgtaaatgg aggagctatt gcccttggtt atccaattgg     2760
```

```
agcatcaggt gcaagaatac tcgttactct tgtacacgca atgcaaaaaa gagatgcaaa   2820
aaaaggctta gcaactttat gtataggtgg cggacaagga acagcaatat tgctagaaaa   2880
gtgctaggag gtaagtttat ggcgcctacc ccgtaggatc caggaggtta gttagaatgg   2940 ttttaaaaa ttggcaggat ctttataaaa gtaaaattgt tagtgcagac gaagctgtat   3000
ctaaagtaag ctgtggagat agcataattt taggcaatgc ttgtggagca tctcttacac   3060
ttttagatgc cttggctgca aataaggaaa agtataagag tgtaaagata cacaatctta   3120
tacttaatta taaaaatgat atatatactg atccggaatc agaaaagtat attcatggaa   3180
atactttctt tgtaagtgga ggtacaaagg aagcagttaa ttgtaataga acagattata   3240
ctccatgctt tttttatgaa ataccaaaat tattaaaaca aaagtatata aatgcagatg   3300
tagcttttat tcaagtaagt aagcctgata gccatggata ctgtagcttt ggagtatcaa   3360
ccgattattc acaggcaatg gtacagtctg caaagcttat aattgcagaa gtaaacgatc   3420
agatgccaag agttttagga gacaatttta tacacatttc tgatatggat tacatagtag   3480
aaagttcacg tccaattcta gaattgactc ctcctaaaat aggagaagta gagaagacaa   3540
taggaaaata ctgtgcatct cttgtagaag atggttctac acttcagctt ggaataggag   3600
ctattccaga tgcagtactt ttattcttga aggataaaaa ggatttgggt atacattcag   3660
aaatgatatc cgatggtgtt gttgaattag ttgaagcagg ggtaattaca aataagaaaa   3720
agtcccttca tccaggaaaa ataattatta cattcttaat gggaactaag aaattatatg   3780
atttcataaa tgataatcct atggtagaag ataccctgt agattatgta aatgatccta   3840
aggttattat gcaaaattct aagatggtat gtataaactc ctgtgtagaa gtggatttca   3900
caggacaagt gtgtgctgaa agtgtaggat ttaaacaaat aagcggtgta ggtgacaag   3960 ttgattacat gagaggagct agcatggctg atggaggaaa atcaattctt gctataccat   4020
ctactgcagc tggcggcaaa atttcaagaa tagttcctat tttaactgaa ggagcggggg   4080
ttactacttc aagatatgat gttcaatatg ttgttacaga atatggtatt gcacttctca   4140
agggcaaatc cataagagaa agagctaagg agcttataaa aattgcacat cctaaattta   4200
gggaagaatt aacagctcaa tttgaaaaaa gattcagttg taagctttaa gcgat        4255
```

<210> SEQ ID NO 25
<211> LENGTH: 568
<212> TYPE: DNA
<213> ORGANISM: Artificial Sequence
<220> FEATURE:
<223> OTHER INFORMATION: pta promotor fragment

<400> SEQUENCE: 25

```
cctgcaggca tttgtcaact atagatggtg aacctctttg cacgaagtta ccactcataa    60
ctgctattac agcatcacat tttgtagcag aacgagcact ttcaatatga tatttatgtc   120
cattgtgaaa gggattatat tcaactatta ttccagttac gttcatagaa attttccttt   180
ctaaaatatt ttattccatg tcaagaactc tgtttatttc attaaagaac tataagtaca   240
aagtataggg catttgaaaa ataggctag tatattgatt gattatttat tttaaaatgc   300
ctaagtgaaa tatatacata ttataacaat aaaataagta ttagtgtagg attttttaaat  360 agagtatcta ttttcagatt aaattttttgc ttatttgatt tacattatat aatattgagt   420
aaagtattga ctagcaaaat ttttgatac tttaatttgt gaaatttctt atcaaaagtt   480
atatttttga atgattttta ttgaaaaata caactaaaaa ggattatagt ataagtgtgt   540
```

-continued gtaattttgt gttaaattta aaggatcc 568

<210> SEQ ID NO 26
<211> LENGTH: 1314
<212> TYPE: DNA
<213> ORGANISM: Clostridium kluyveri

<400> SEQUENCE: 26
atggttttta aaaattggca ggatctttat aaaagtaaaa ttgttagtgc agacgaagct 60
gtatctaaag taagctgtgg agatagcata attttaggca atgcttgtgg agcatctctt 120
acacttttag atgccttggc tgcaaataag gaaaagtata agagtgtaaa gatacacaat 180
cttatactta attataaaaa tgatatatat actgatccgg aatcagaaaa gtatattcat 240
ggaaatactt tctttgtaag tggaggtaca aaggaagcag ttaattgtaa tagaacagat 300
tatactccat gcttttttta tgaaatacca aaattattaa aacaaaagta tataaatgca 360
gatgtagctt ttattcaagt aagtaagcct gatagccatg gatactgtag ctttggagta 420
tcaaccgatt attcacaggc aatggtacag tctgcaaagc ttataattgc agaagtaaac 480
gatcagatgc caagagtttt aggagacaat tttatacaca tttctgatat ggattacata 540
gtagaaagtt cacgtccaat tctagaattg actcctccta aaataggaga agtagagaag 600
acaataggaa aatactgtgc atctcttgta gaagatggtt ctacacttca gcttggaata 660
ggagctattc cagatgcagt acttttattc ttgaaggata aaaaggattt gggtatacat 720
tcagaaatga tatccgatgg tgttgttgaa ttagttgaag caggggtaat tacaaataag 780
aaaaagtccc ttcatccagg aaaaataatt attacattct taatgggaac taagaaatta 840
tatgatttca taaatgataa tcctatggta gaaggatacc ctgtagatta tgtaaatgat 900
cctaaggtta ttatgcaaaa ttctaagatg gtatgtataa actcctgtgt agaagtggat 960
ttcacaggac aagtgtgtgc tgaaagtgta ggatttaaac aaataagcgg tgtaggtgga 1020
caagttgatt acatgagagg agctagcatg gctgatggag gaaaatcaat tcttgctata 1080
ccatctactg cagctggcgg caaaatttca agaatagttc ctattttaac tgaaggagcg 1140
ggggttacta cttcaagata tgatgttcaa tatgttgtta cagaatatgg tattgcactt 1200
ctcaagggca aatccataag agaaagagct aaggagctta taaaaattgc acatcctaaa 1260
tttagggaag aattaacagc tcaatttgaa aaaagattca gttgtaagct ttaa 1314

<210> SEQ ID NO 27
<211> LENGTH: 433
<212> TYPE: PRT
<213> ORGANISM: C. carboxidivorans

<400> SEQUENCE: 27

Met Asp Trp Lys Lys Leu Tyr Lys Ser Lys Leu Val Ser Ala Lys Glu
1 5 10 15

Ala Val Ser Asn Ile Lys Ser Asn Ser Arg Val Val Val Ser Ile Ala
20 25 30

Val Ala Glu Pro Thr Glu Leu Ile Asp Ala Leu Val Ala Asn Lys Glu
35 40 45

Asn Tyr Glu Asn Val Glu Val Val His Met Val Asp Met Gly Lys Ser
50 55 60

Glu Tyr Ala Gln Glu Gly Met Glu Lys Tyr Phe Lys Tyr Asn Ser Ile
65 70 75 80

Phe Val Gly Ala Ser Thr Lys Asp Ala Val Asn Ser Gly Arg Ser Asp
85 90 95

Phe Thr Pro Cys Cys Phe Tyr Glu Leu Pro Arg Leu Phe Glu Gly
            100                 105                 110

Tyr Leu Pro Val Asp Val Val Leu Ile Gln Val Ser Lys Pro Asp Lys
        115                 120                 125

His Gly Tyr Cys Ser Phe Gly Val Ser Asn Asp Tyr Thr Lys Pro Ala
    130                 135                 140

Ala Asp Cys Ala Lys Met Val Ile Ala Glu Val Asn Glu Asn Met Pro
145                 150                 155                 160

Arg Val Leu Gly Asp Ser Phe Ile His Ile Ser Asp Ile Asp Tyr Ile
                165                 170                 175

Val Glu Thr Ser His Pro Ile Met Glu Leu Lys Gln Pro Lys Ile Gly
            180                 185                 190

Lys Ile Glu Glu Ala Ile Gly Glu Tyr Cys Ala Ser Leu Ile Glu Asp
        195                 200                 205

Gly Ser Thr Leu Gln Leu Gly Ile Gly Ala Ile Pro Asp Ala Val Leu
    210                 215                 220

Leu Phe Leu Lys Asp Lys Lys Asp Leu Gly Ile His Ser Glu Met Ile
225                 230                 235                 240

Ser Asp Gly Val Val Asp Leu Val Glu Ser Gly Val Ile Asn Asn Lys
                245                 250                 255

Glu Lys Thr Leu Asn Pro Gly Lys Ile Val Val Thr Phe Phe Met Gly
            260                 265                 270

Thr Lys Lys Leu Tyr Asp Phe Ile Asp Asp Asn Pro Met Val Glu Ser
        275                 280                 285

Tyr Pro Val Ser Tyr Val Asn Asp Pro Thr Val Ile Met Lys Asn Ser
    290                 295                 300

Lys Met Ile Ser Ile Asn Ser Cys Val Glu Val Asp Leu Met Gly Gln
305                 310                 315                 320

Val Cys Ser Glu Ser Ile Gly Met Asn Gln Ile Ser Gly Ile Gly Gly
                325                 330                 335

Gln Val Asp Phe Ile Arg Gly Ala Asn Met Cys Lys Asp Gly Lys Ala
            340                 345                 350

Ile Ile Ala Ile Pro Ser Thr Ala Ala Lys Gly Lys Val Ser Arg Ile
        355                 360                 365

Val Pro Leu Ile Glu Lys Gly Thr Pro Ile Thr Thr Ser Arg Thr Asp
    370                 375                 380

Val Asp Tyr Ile Ile Thr Glu Tyr Gly Ile Ala Arg Leu Lys Ser Lys
385                 390                 395                 400

Ser Leu Lys Glu Arg Ala Arg Ala Leu Ile Asn Ile Ala His Pro Asp
                405                 410                 415

Phe Arg Ala Trp Leu Ile Asp Glu Tyr Glu Lys Arg Phe Lys Thr Lys
            420                 425                 430

Phe

<210> SEQ ID NO 28
<211> LENGTH: 1179
<212> TYPE: DNA
<213> ORGANISM: Clostridium acetobutylicum

<400> SEQUENCE: 28
atgaaagaag ttgtaatagc tagtgcagta agaacagcga ttggatctta tggaaagtct        60
cttaaggatg taccagcagt agatttagga gctacagcta taaggaagc agttaaaaaa       120 gcaggaataa aaccagagga tgttaatgaa gtcattttag gaaatgttct tcaagcaggt       180

```
ttaggacaga atccagcaag acaggcatct tttaaagcag gattaccagt tgaaattcca      240
gctatgacta ttaataaggt ttgtggttca ggacttagaa cagttagctt agcagcacaa      300
attataaaag caggagatgc tgacgtaata atagcaggtg gtatggaaaa tatgtctaga      360
gctccttact tagcgaataa cgctagatgg ggatatagaa tgggaaacgc taaatttgtt      420
gatgaaatga tcactgacgg attgtgggat gcatttaatg attaccacat gggaataaca      480
gcagaaaaca tagctgagag atggaacatt tcaagagaag aacaagatga gtttgctctt      540
gcatcacaaa aaaagctga agaagctata aaatcaggtc aatttaaaga tgaaatagtt      600
cctgtagtaa ttaaaggcag aaagggagaa actgtagttg atacagatga gcaccctaga      660
tttggatcaa ctatagaagg acttgcaaaa ttaaaacctg ccttcaaaaa agatggaaca      720
gttacagctg gtaatgcatc aggattaaat gactgtgcag cagtacttgt aatcatgagt      780
gcagaaaaag ctaaagagct tggagtaaaa ccacttgcta agatagtttc ttatggttca      840
gcaggagttg acccagcaat aatgggatat ggaccttct atgcaacaaa agcagctatt      900
gaaaaagcag gttggacagt tgatgaatta gatttaatag aatcaaatga agcttttgca      960
gctcaaagtt tagcagtagc aaaagattta aaatttgata tgaataaagt aaatgtaaat     1020
ggaggagcta ttgcccttgg tcatccaatt ggagcatcag gtgcaagaat actcgttact     1080
cttgtacacg caatgcaaaa aagagatgca aaaaaaggct tagcaacttt atgtataggt     1140
ggcggacaag gaacagcaat attgctagaa aagtgctag                            1179
```

<210> SEQ ID NO 29
<211> LENGTH: 849
<212> TYPE: DNA
<213> ORGANISM: Clostridium kluyveri

<400> SEQUENCE: 29

```
atgagtatta aaagtgtagc ggttttaggt agtggaacta tgtctcgtgg aattgtgcag       60
gcttttgcag aagcaggtat agatgtaatt atccgtggaa gaactgaagg tagtattgga      120
aaaggtctag cagcagtaaa gaaagcttat gataaaaaag tatcaaaggg gaaaatttcc      180
caggaagatg ctgataaaat agttggaaga gtaagtacaa caactgaact tgaaaaattg      240
gctgattgtg atcttataat agaagcagca tcagaggata tgaatataaa gaaagactat      300
tttgaaaaat tagaagaaat atgcaagcct gaaacaattt ttgctactaa tacttcttca      360
ttatctataa ctgaagtagc aacagctaca aagagaccag ataaattcat aggaatgcat      420
ttctttaatc cagcaaatgt tatgaaatta gttgaaatca taagaggtat gaatacttca      480
caagaaactt ttgatattat aaaagaagct tccattaaaa taggaaaaac tcctgtagaa      540
gttgcagaag ctccaggatt tgttgtaaac aagatattag taccaatgat caatgaagca      600
gtaggaattt tggcagaagg aatagcttca gcagaagata tcgatacagc tatgaaatta      660
ggcgctaatc acccaatggg tcctttagca ttaggagatc ttattggact tgatgtagtt      720
cttgcagtta tggatgtact ttatagtgaa actggagatt caaaatatag agctcataca      780
ttacttagaa aatatgtaag agcaggatgg cttggaagaa aatcaggaaa aggattcttc      840
gcttattaa                                                             849
```

<210> SEQ ID NO 30
<211> LENGTH: 780
<212> TYPE: DNA
<213> ORGANISM: Clostridium kluyveri

<400> SEQUENCE: 30

```
atggaattta aaatatcat tcttgaaaag gatggaaatg tggcttcaat aacgttgaat      60
agacctaagg cattaaatgc attaaatgca gcaactttaa aagagataga tgccgcaata     120
aacgacattg ctgaagatga taacgtatat gctgtgataa ttactgggtc aggtaaagct    180
tttgtagcag gagcagatat agctgagatg aaagatctta ctgcagttga gggaagaaag    240
ttttcagttc ttggcaataa aatatttaga aaattagaaa attagaaaaa accagttata    300
gcagctataa atggatttgc actgggtggt ggctgtgaat tgtcattgtc ttgcgatata    360
agaatagctt catcaaaggc taagtttggt caaccagagg ttggtcttgg aattactcca    420
gggtttggag gtactcaaag acttgcaaga gcaataggcg ttggtatggc taaggaactt    480
atatataccg gaaaagtaat taatgctgaa gaggcattaa gaataggttt ggtaaataaa    540
gtagttgagc cagataaatt attggaagaa gctaaagctt tagtagatgc tattattgtt    600
aatgcaccta tagctgttag aatgtgtaag gctgctataa atcaaggact tcagtgtgat    660
atagatacag gtgtagctta tgaagcagaa gtatttgggg aatgttttgc tacagaagat    720
agagtagaag gaatgacagc atttgtagaa aaaagagaca aggctttttaa aaataagtaa    780
```

<210> SEQ ID NO 31
<211> LENGTH: 1140
<212> TYPE: DNA
<213> ORGANISM: Clostridium kluyveri

<400> SEQUENCE: 31

```
atggatttta cattaacaaa cgagcaaaaa tttgtagaac aaatggtaag tgaatttact     60
gaaaatgaag ttaaacctat agctgctgaa atagatgaaa cagaaaggtt tcctcttgag   120
acagtagaaa aatttgctaa atacggaatg atgggtatgc cttttccagt tgaatacggc    180
ggctcaggta cagattattt atcctatata atagcagtag aaggacttgc aaagagttgt   240
acttcatcat caactatatt gtcagcacat acttcacttt gtgcagcacc tatttatgat    300
tggggtacag aagaacagaa acaaaaatac ttagttcctc ttgcaaaggg agaaaaactt    360
ggagcatttg gttaactga acctaatgca ggtactgatg ctgctggaca gcagacaaca    420
gctgttttag aaggggatca ttatgtatta aatggacaaa aatatttat tacaaatggt    480
gcatatgcag atacttttgt aatatttgca atgacagaca gaagcaaggg tacaagagga    540
ataacagcat ttatagttga aaaagatttc cctggtttct ccataggaaa atctgaagat    600
aagttgggaa ttagagcttc ctcaactaca gaacttatat ttgagaattg catagttcca    660
aaagaaaata tgttaggaaa agaaggaaaa ggatttactg tagcaatgca tactcttgat    720
ggaggaagaa ttggtatagc agcacaagcg ttaggtttag cagaaggcgc attagctgaa    780
gcacttaatt atatgaaaga aagaaaacaa tttggaaaag ctctttacaa attccaggga    840
ttagcatgga tggttgcaga attagatact aaaatagaag ctgttaaaca acttgtttat    900
aaagcagcag taaataaaca aatgggtctt ccatattcag tggaagctgc aagagctaaa    960
ttagctgcgg ctactgtagc tatggaaaca actactaaag ttgttcaaat ctttggtgga   1020
tatggattca ctaaggatta tccagtagaa agaatgatga gagatgctaa gataactgaa   1080
atatatgaag gaacttcaca agtacaaaag atggttattt cagcaaattt atttaaataa   1140
```

<210> SEQ ID NO 32
<211> LENGTH: 780
<212> TYPE: DNA
<213> ORGANISM: Clostridium kluyveri

<400> SEQUENCE: 32

```
atgaaaatag tagtttgctt aaagcaagta ccagatacaa ctgaagttaa aatagatcca      60
aaaacaggaa cattaataag agaaggcgtt ccatcaataa taaacccaga tgataaaaat     120
gcacttgaag aatcaattgc tttaaaagaa aaagtagggg gtacagttac agtagtaagc     180
atggggcctc cacaggcagt ggatgcactt agagaagctc tagctatggg agctgatgaa     240
gcaatattag tttcagacag agcttttgca ggagcagata ctcaagctac ttcctatgca     300
ttagcaggag cacttaaaaa tttagaatat gatttaatat ttgcaggaag acaagctata     360
gatggagata ctgcacaggt tggacctcaa atagcagaaa aattaggaat acctcagata     420
acatatgtag aaaaagttga tgtagatgga gatactttaa cagttcaaag agcttgggaa     480
gatggatatg aagtagcaaa aattaaaact ccatgcatgt taactgctat aaaagagtta     540
aatcaaccaa gatatatgaa catgaagaac atatttgaag ttttcaagaa agaagttaaa     600
atatggagtg ctgacgactt agatgtagat aaaaataaac ttggtcttaa tggttcctgc     660
acaaaagtta agagatcaca tacaaaagaa gcaaaggag  caggagaaat cgttaataaa     720
ccaataaaag aagcagtagc atattcaatt tcaaaattaa gagaaaaaca tgtcatttaa     780
```

<210> SEQ ID NO 33
<211> LENGTH: 1005
<212> TYPE: DNA
<213> ORGANISM: Clostridium kluyveri

<400> SEQUENCE: 33

```
atgaacttag cagaatacaa aggcgtatgg gtatttgctg aacaagggga tggagaacta      60
caaaaagtag cacttcaatt agttggaaaa ggaagagaat ggcagacac tttaggagta     120
gaattaactg ctgtattact tggtagtgaa gtagatgatt tggcaaaaga attagttgca     180
tatggagcag acaatgtttt atacgcagat agtcctcttt taaaacatta tactacagat     240
ggatacacta agtaataga tgaacttata aaagaaagaa accagaaat attacttata     300
ggagctacat ttatcggaag agacttagga ccaagagttg caggtagagt ttttacaggt     360
cttacagcag actgtacagg acttgatata gatgaggcaa caaaaaattt gatgatgaca     420
agacctgcat ttggtggaaa cttaatggca actatagctt gcgaaaaaac aagacctcaa     480
atgtcaacag taagaccagg agttttttat gcgcttccaa gagatgcttc aagaactgga     540
aaaatagaaa aatagctgc aaatgttgca aaagatgaca tcagaattga agtgcttgaa     600
gtagttaaat ctgctggcga tacaatagat atttcagaag cagatgtaat tgtatcaggt     660
ggaagaggac ttggtggtcc agatggattc aaagttctta agaattagc agatttatta     720
ggtgaaacta taggtggatc ccgtgcaact atagatgctg gctggataga taagagctat     780
caggttggac aaactggtaa aacagtaaga ccaggtcttt atattgcatg cggaatatca     840
ggtcaaatac aacatttagc tggtatgcag gatagtggat ttatcgtagc tatcaataaa     900
gatgaaaacg ctccaatgat gcaagtagcg gatcttgcaa ttgtaggaga tttatataag     960
gttgttccag aatttgtaga acaagttaaa gctttaaatc tttaa                   1005
```

<210> SEQ ID NO 34
<211> LENGTH: 1140
<212> TYPE: DNA
<213> ORGANISM: Clostridium acetobutylicum

<400> SEQUENCE: 34

```
atggatttta atttaacaag agaacaagaa ttagtaagac agatggttag agaatttgct      60
gaaaatgaag ttaaacctat agcagcagaa attgatgaaa cagaaagatt tccaatggaa     120
aatgtaaaga aaatgggtca gtatggtatg atgggaattc cattttcaaa agagtatggt     180
ggcgcaggtg gagatgtatt atcttatata atcgccgttg aggaattatc aaaggtttgc     240
ggtactacag gagttattct ttcagcacat acatcacttt gtgcttcatt aataaatgaa     300
catggtacag aagaacaaaa acaaaaatat ttagtacctt tagctaaagg tgaaaaaata     360
ggtgcttatg gattgactga gccaaatgca ggaacagatt ctggagcaca acaaacagta     420
gctgtacttg aaggagatca ttatgtaatt aatggttcaa aatattcat aactaatgga      480
ggagttgcag atacttttgt tatatttgca atgactgaca gaactaaagg aacaaaaggt     540
atatcagcat ttataataga aaaaggcttc aaaggtttct ctattggtaa agttgaacaa     600
aagcttggaa taagagcttc atcaacaact gaacttgtat ttgaagatat gatagtacca     660
gtagaaaaca tgattggtaa agaaggaaaa ggcttcccta tagcaatgaa aactcttgat     720
ggaggaagaa ttggtatagc agctcaagct ttaggtatag ctgaaggtgc tttcaacgaa     780
gcaagagctt acatgaagga gagaaaacaa tttggaagaa gccttgacaa attccaaggt     840
cttgcatgga tgatggcaga tatggatgta gctatagaat cagctagata tttagtatat     900
aaagcagcat atcttaaaca agcaggactt ccatacacag ttgatgctgc aagagctaag     960
cttcatgctg caaatgtagc aatggatgta acaactaagg cagtacaatt atttggtgga    1020
tacggatata caaaagatta tccagttgaa agaatgatga gagatgctaa gataactgaa    1080
atatatgaag gaacttcaga agttcagaaa ttagttattt caggaaaaat ttttagataa    1140
```

<210> SEQ ID NO 35
<211> LENGTH: 1011
<212> TYPE: DNA
<213> ORGANISM: Clostridium acetobutylicum

<400> SEQUENCE: 35

```
atgaataaag cagattacaa gggcgtatgg gtgtttgctg aacaaagaga cggagaatta      60
caaaaggtat cattggaatt attaggtaaa ggtaaggaaa tggctgagaa attaggcgtt     120
gaattaacag ctgttttact tggacataat actgaaaaaa tgtcaaagga tttattatct     180
catggagcag ataaggtttt agcagcagat aatgaacttt tagcacattt ttcaacagat     240
ggatatgcta aagttatatg tgatttagtt aatgaaagaa agccagaaat attattcata     300
ggagctactt tcataggaag agatttagga ccaagaatag cagcaagact ttctactggt     360
ttaactgctg attgtacatc acttgacata gatgtagaaa atagagattt attggctaca     420
agaccagcgt ttggtggaaa tttgatagct acaatagttt gttcagacca cagaccacaa     480
atggctacag taagacctgg tgtgtttgaa aaattacctg ttaatgatgc aaatgtttct     540
gatgataaaa tagaaaaagt tgcaattaaa ttaacagcat cagacataag aacaaaagtt     600
tcaaaagttg ttaagcttgc taaagatatt gcagatatcg gagaagctaa ggtattagtt     660
gctggtggta gaggagttgg aagcaaagaa aactttgaaa aacttgaaga gttagcaagt     720
ttacttggtg gaacaatagc cgcttcaaga gcagcaatag aaaaagaatg ggttgataag     780
gaccttcaag taggtcaaac tggtaaaact gtaagaccaa ctctttatat tgcatgtggt     840
atatcaggag ctatccagca tttagcaggt atgcaagatt cagattacat aattgctata     900
aataaagatg tagaagcccc aataatgaag gtagcagatt tggctatagt tggtgatgta     960
aataaagttg taccagaatt aatagctcaa gttaaagctg ctaataatta a            1011
```

<210> SEQ ID NO 36
<211> LENGTH: 780
<212> TYPE: DNA
<213> ORGANISM: Clostridium acetobutylicum

<400> SEQUENCE: 36

```
atgaatatag ttgtttgttt aaaacaagtt ccagatacag cggaagttag aatagatcca      60
gttaagggaa cacttataag agaaggagtt ccatcaataa taaatccaga tgataaaaac     120
gcacttgagg aagctttagt attaaaagat aattatggtg cacatgtaac agttataagt     180
atgggacctc cacaagctaa aaatgcttta gtagaagctt tggctatggg tgctgatgaa     240
gctgtacttt taacagatag agcatttgga ggagcagata cacttgcgac ttcacataca     300
attgcagcag gaattaagaa gctaaaatat gatatagttt ttgctggaag gcaggctata     360
gatggagata cagctcaggt tggaccagaa atagctgagc atcttggaat acctcaagta     420
acttatgttg agaaagttga agttgatgga gatactttaa agattagaaa agcttgggaa     480
gatggatatg aagttgttga agttaagaca ccagttcttt taacagcaat taagaattta     540
aatgttccaa gatatatgag tgtagaaaaa atattcggag catttgataa agaagtaaaa     600
atgtggactg ccgatgatat agatgtagat aaggctaatt taggtcttaa aggttcacca     660
actaaagtta agaagtcatc aactaaagaa gttaaaggac aggagaagt tattgataag     720
cctgttaagg aagcagctgc atatgttgtc tcaaaattaa aagaagaaca ctatatttaa     780
```

<210> SEQ ID NO 37
<211> LENGTH: 1689
<212> TYPE: DNA
<213> ORGANISM: Clostridium kluyveri

<400> SEQUENCE: 37

```
atgaactttg aactcaccaa agaacaacaa atgattagag ataatgttcg aaagtttgca      60
gaagcaaaaa tcgagcctat tgcatttcaa ctagatgaga aaatatatt tcctgaagaa     120
atagttaatg atgggggga tctatctatt atgggtcttc catacccaaa agaatatggt     180
ggagcgggaa aagatgtatt gagctatgct attgcggtag aagaactatc aagggtagat     240
gcaggtgtgg tgttatatt atctgcacac acatctcttg gaacttggcc tattatggag     300
tttgggacaa agaacaaaa agaaaaatat ctagttccac tggcctcggg caagaaaatt     360
gctgcttttg gtcttacaga acctaatgct ggaagtgatg ccggcaagac agaaactaca     420
gcggtttag aaggcgatca ttatgtcata aatggttcta aggtatttat aacaaatgcg     480
gattatgcag atacttatgt aatatttgcg gttacaactc aggtttgggaa accaaggga     540
ataagtgcct ttattattga agggtatgg atggatttta cttttggtac tcattataat     600
aaaatgggta tacgttcttc cgctacagca gagctttat ttaaaaattt gaaggtacca     660
aaatataatc ttttgggaaa agaaaatgag ggctttaaaa ttgccatgca gaccctagaa     720
ggtgggcgca taggtattgc ggcacaggca cttggaattg cccagggtgc atatgagaaa     780
gcactaagct actccaagga aagagttcag tttggaaaac tatttcaag acaacaatcc     840
atagcattta aacttgcgga tatggctact aaaattcggg cggctagatt tatggtatat     900
agtgcagctg tattaaagca ggaacataaa aattatgaa tggaatccgc tatggcgaaa     960
ttgtatgctt ctgatatttg ccttgaagtt gttaatgatg cagtgcaaat atatgggggc    1020
tcaggattta ttaaaggatt tcctgtagag cgtatgtacc gtgatgctaa gatctgtaca    1080
```

| | |
|---|---|
| atatatgaag gaactaatga gattcaaaga cttattatct ccaatgatat tttaggtaaa | 1140 |
| cctaaaaaag aacctattga ggaaaataaa gaaaataaag ttaataaagc aaaacctata | 1200 |
| acgggaaacc gtaggagggt cattataaaa gaaggctctc caaagaaaaa ggtggatgca | 1260 |
| ttttttaaatt atattaaaag tgaaaatata gatattaata aaagtgaagc ttctaaagga | 1320 |
| agtatagcag acgcagataa agtatgcagt ataggactgg gattaaagga taaaaaagac | 1380 |
| ttgcctttaa tacaatcact agcggataca gttggtgctg aacttggctg ttccagacct | 1440 |
| gtggctgaag aaagggaatg gctgccactt gatcgttatg taggcatatc gggtcagaaa | 1500 |
| ttcggtggaa cattttatct tgccattggt atatcaggac aagttcaaca tttaaaggga | 1560 |
| attgaaaatg ctggaattat aactgctata aacatagatg aggatgctcc tatatttaag | 1620 |
| agttcagatt atggtattgt aggagatcta tatgaaattg tgccgctgct tattgaggct | 1680 |
| ttaaaatag | 1689 |

<210> SEQ ID NO 38
<211> LENGTH: 789
<212> TYPE: DNA
<213> ORGANISM: Clostridium kluyveri

<400> SEQUENCE: 38

| | |
|---|---|
| atgtttaatc taccagaaga agtaacctat acaattaacc tgaagaattt aattaaagat | 60 |
| atcaaacctg aaattttttt gattggtgcc actaccctgg aagatcatt ggcacctagg | 120 |
| ctggcagcgt ccttaaatac gggacttaca gcagattgta caggtcttga atcgatgaa | 180 |
| gatagaaaat tggttcagat aagaccggct tttagcgaaa atatactggc tcatataaaa | 240 |
| acatacacat atccccagat ggctacagtg agatataaag aatttgacga gggcacaaga | 300 |
| gatgctaaaa ggcagggaga tattttaaag gtagaggctt taagactcga aaatgaactg | 360 |
| gtaaaagtga taacacaact tagatcccag gaaattaata tatctgatgc aaatgtagta | 420 |
| gtggcagcgg gtaaaggatt gaaaaaggca aagatatgg ctatgttaaa ggagttagcg | 480 |
| gatttgctgg gaggtgtagt tggagccagc agggaaatag ttgaagaagg gtttatatcc | 540 |
| aaggactttc aagtaggata cagcggcaac agggtaaaac ctaaattata tatagcttgt | 600 |
| ggaatttcag gagcaccgca gcaccttgca ggaatgaaag aatcgggggtt tattgttgca | 660 |
| atcaatacag atccttcagc tcctatattt aatatagcag actacggaat agttgatgat | 720 |
| atgtataagg taatacctga tttgataact aagataaaag aaagcagttt agaaactata | 780 |
| aattgttaa | 789 |

<210> SEQ ID NO 39
<211> LENGTH: 894
<212> TYPE: DNA
<213> ORGANISM: Clostridium kluyveri

<400> SEQUENCE: 39

| | |
|---|---|
| atgggtggta ccgcggcaga catttcgccc cagcgaaata ggtctgtctt tttatttgcc | 60 |
| atttgtttga gagaaaggaa agaagcttta atggatatta gtttttagt taaacaagtt | 120 |
| ccggatatgg aaaagtaaa atttgacaga gaaaagggag tagtagatag aacatctgcc | 180 |
| agtgcagaaa tcaatccttt tgatttaaat gcactggaaa cagcagttca atagctgaa | 240 |
| aatatcgatg ccagagttac tgctgtaagt atggggcctc caaatacaga aagtgcgtta | 300 |
| aaagaatgta ttgcaggggg tgctcatgaa ggagtgcttg taagtgatag aaaatttgga | 360 |
| ggttcagata caaaggcgac ttctaaaata cttgccagtg ccattaaaaa gttgggagcc | 420 |

| | |
|---|---|
| tatgatctgg taatcgctgg agaaaagact gtagatggag atacaggaca ggttggtccc | 480 |
| gaagttgcag aattttaaa tatacctcat gcaagttatg taagtaaaat tacagaaatg | 540 |
| aataaggaca gcatggaggt acattctgaa atctgggaag aacttattt aaaaagtata | 600 |
| aaatttccat gtcttattac agttacaaag gatatcaatc atccaagatt gccttctttt | 660 |
| aaaaataaga tgaaagccag aaaagcagag attaagatat taaagcttga ggatttagaa | 720 |
| gaattttga atgaggataa tgttggcttt aagggttcac ctacaaaagt aaagaaaata | 780 |
| gaaattcccc aaatagaaaa aagacaggga aaaatttata gggagtcaga tactgttgag | 840 |
| gcagagaatg aattaattaa tatatttaaa aagattaagg ttttggaggt gtag | 894 |

<210> SEQ ID NO 40
<211> LENGTH: 2524
<212> TYPE: DNA
<213> ORGANISM: Artificial Sequence
<220> FEATURE:
<223> OTHER INFORMATION: codon optimized trans-2-enoyl-CoA reductase (TER_Eg(coC1))

<400> SEQUENCE: 40

| | |
|---|---|
| gcaggtggta tggaaaatat gtctagagct ccttacttag cgaataacgc tagatgggga | 60 |
| tatagaatgg gaaacgctaa atttgttgat gaaatgatca ctgacggatt gtgggatgca | 120 |
| tttaatgatt accacatggg aataacagca gaaaacatag ctgagagatg aacatttca | 180 |
| agagaagaac aagatgagtt tgctcttgca tcacaaaaaa aagctgaaga agctataaaa | 240 |
| tcaggtcaat ttaaagatga aatagttcct gtagtaatta aaggcagaaa gggagaaact | 300 |
| gtagttgata cagatgagca ccctagattt ggatcaacta tagaaggact tgcaaaatta | 360 |
| aaacctgcct tcaaaaaga tggaacagtt acagctggta atgcatcagg attaaatgac | 420 |
| tgtgcagcag tacttgtaat catgagtgca gaaaagcta agagcttgg agtaaaacca | 480 |
| cttgctaaga tagttctta tggttcagca ggagttgacc cagcaataat gggatatgga | 540 |
| cctttctatg caacaaagc agctattgaa aaagcaggtt ggacagttga tgaattagat | 600 |
| ttaatagaat caaatgaagc ttttgcagct caaagtttag cagtagcaaa agattaaaa | 660 |
| tttgatatga ataaagtaaa tgtaaatgga ggagctattg cccttggtta tccaattgga | 720 |
| gcatcaggtg caagaatact cgttactctt gtacacgcaa tgcaaaaag agatgcaaaa | 780 |
| aaaggcttag caactttatg tataggtggc ggacaaggaa cagcaatatt gctagaaaag | 840 |
| tgctaggagg taagtttatg gcgcctaccc cgtaggatcc aggaggttag ttagaatgtc | 900 |
| gtgcccgcc tcgccgtctg ctgccgtggt gtctgccggc gccctctgcc tgtgcgtggc | 960 |
| aacggtattg ttggcgactg gatccaaccc caccgccctg tccactgctt ccactcgttc | 1020 |
| tccgacctca ctggtccgtg gggtggacag gggcttgatg aggccaacca ctgcagcggc | 1080 |
| tctgacgaca atgagagagg tgccccagat ggctgaggga ttttcaggcg aagccacgtc | 1140 |
| tgcatgggcc gccgcgggc cgcagtgggc ggcgccgctc gtggccgcgg cctcctccgc | 1200 |
| actggcgctg tggtggtggg ccgccaggcg tagcgtgagg aggccgctgg cagcgctggc | 1260 |
| ggagctgccc accgcggtca cccacctggc cccccgatg gcgatgttca ccaccacagc | 1320 |
| gaaggtcatc cagcccaaga ttcgtggctt catctgcacg accacccacc cgatcggctg | 1380 |
| tgagaagagg gtccaggagg agatcgcgta cgcccgtgcc cacccgccca ccagccctgg | 1440 |
| cccgaagagg gtgctggtca tcggctgcag taccggctac gggctctcca cccgtatcac | 1500 |
| cgctgccttc ggctaccagg ccgccacgct gggcgtgttc ctggcgggcc cccgacgaa | 1560 |

```
gggccgtccc gccgcggcgg gctggtacaa caccgtggcg ttcgagaagg ccgccctgga    1620
ggccgggctg tacgccagga gccttaatgg cgacgccttc gactccacaa cgaaggcgag    1680
gacggtcgag gcgatcaaga gggacctcgg cacggtggac ctcgtggtgt acagcatcgc    1740
cgccccgaag aggacggacc ctgccaccgg cgtcctccac aaggcctgcc tgaagcccat    1800
cggcgccacg tacaccaacc gtactgtgaa caccgacaag gcggaggtga ccgacgtcag    1860
cattgagccg gcctcccccg aagagatcgc ggacacggtg aaggtgatgg gcggggagga    1920
ctgggagctc tggatccagg cgctgtcgga ggccggcgtg ctggcggagg gggccaagac    1980
ggtggcgtac tcctacatcg ccccgagat gacgtggcct gtctactggt ccggcaccat    2040
cggggaggcc aagaaggacg tggagaaggc tgccaagcgt atcacgcagc agtacggctg    2100
cccggcgtac ccggtggtgg ccaaggcctt ggtcacccag gccagctccg ccatcccggt    2160
ggtgccgctc tacatctgcc tgctgtaccg tgttatgaag gagaagggca cccacgaggg    2220
ctgcatcgag cagatggtga ggctgctcac cacgaagctg taccccgaga cggggcccc    2280 catcgtcgat gaggccggac gtgtgagggt ggatgactgg gagatggcgg aggatgtgca    2340
gcaggctgtt aaggacctct ggagccaggt gagcactgcc aacctcaagg acatctccga    2400
cttcgctggg tatcaaactg agttcctgag gctgttcggg ttcggcattg acggcgtgga    2460
ctacgaccag cccgtggacg tggaggcgga cctccccagt gctgcccagc agtaggcggc    2520
cgct                                                                2524
```

<210> SEQ ID NO 41
<211> LENGTH: 1238
<212> TYPE: DNA
<213> ORGANISM: Artificial Sequence
<220> FEATURE:
<223> OTHER INFORMATION: codon optimized trans-2-enoyl-CoA reductase
      from Treponema denticola (TER_Td(coCl))

<400> SEQUENCE: 41

```
ggcgcctacc ccgtaggatc caggaggtta gttagaatga tagtaaaacc aatggtaaga      60
aataatatat gtcttaatgc tcatcctcag ggttgtaaga aggcgtaga ggatcaaata     120 gagtatacta agaaaagaat tacagctgag gttaaagctg gagcaaaagc tcctaaaaac    180
gtattagtac ttgatgttc aaatggatat ggtcttgcat ctagaataac agcagcattt    240
ggatatggag cagccacaat tggtgtttca tttgaaaagg ctggatcaga aacaaagtat    300
ggaactcctg gttggtacaa taatcttgca ttcgatgaag ctgctaagag agagggactt    360
tatagtgtta ctatagacgg tgatgcgttt tctgacgaga ttaaagctca ggtaatagaa    420
gaagccaaga aaagggtat aaagtttgat ctaatagttt attctttagc atctcctgtt    480
aggacagacc cagatacagg aattatgcat aaaagtgtac tgaaaccttt tggaaaaaca    540
tttaccggca aaactgttga tccatttact ggggaattga agaaataag tgctgaacca    600 gcaaatgatg aagaagcggc agcaactgtt aaagtaatgg gtgagagga ttgggaacgt    660 tggataaagc aactatcaaa agaaggatta ttagaggaag gctgcataac attagcttac    720
agctacatag gaccagaggc tacgcaagct ctttatagaa aggtacaat tggaaaggca    780 aaggaacatt tagaagcaac cgcacataga ctcaataaag aaaaccttc cattagagca    840 tttgttagtg tcaataaagg tttagtaact agagctagcg ctgttatccc agtgattcct    900
ttgtatcttg cttcattatt caaagttatg aagagaaag gtaatcacga agggtgcata    960
gaacaaatta ctagattata tgcggaaaga ttgtatagaa aagatggaac aattcctgtt    1020
```

| | | |
|---|---|---|
| gatgaagaaa atagaataag aatagatgat tgggaattag aagaagatgt gcaaaaagct | 1080 | |
| gtaagtgcat taatggaaaa agtgacaggt gagaatgcag agtctttaac tgatctagcc | 1140 | |
| ggatataggc atgattttct tgcaagtaat ggatttgatg ttgaaggcat aaactatgaa | 1200 | |
| gcagaagtag aaagatttga taggatttaa gcggccgc | 1238 | |

<210> SEQ ID NO 42
<211> LENGTH: 1938
<212> TYPE: DNA
<213> ORGANISM: Artificial Sequence
<220> FEATURE:
<223> OTHER INFORMATION: codon optimized trans-2-enoyl-CoA reductase from Caenorhabditis elegans (TER_Ce(coC1))

<400> SEQUENCE: 42

| | | |
|---|---|---|
| gcaggtggta tggaaaatat gtctagagct ccttacttag cgaataacgc tagatgggga | 60 | |
| tatagaatgg gaaacgctaa atttgttgat gaaatgatca ctgacggatt gtgggatgca | 120 | |
| tttaatgatt accacatggg aataacagca gaaaacatag ctgagagatg gaacatttca | 180 | |
| agagaagaac aagatgagtt tgctcttgca tcacaaaaaa aagctgaaga agctataaaa | 240 | |
| tcaggtcaat ttaaagatga aatagttcct gtagtaatta aaggcagaaa gggagaaact | 300 | |
| gtagttgata cagatgagca ccctagattt ggatcaacta tagaaggact tgcaaaatta | 360 | |
| aaacctgcct tcaaaaaaga tggaacagtt acagctggta atgcatcagg attaaatgac | 420 | |
| tgtgcagcag tacttgtaat catgagtgca gaaaaagcta aagagcttgg agtaaaacca | 480 | |
| cttgctaaga tagtttctta tggttcagca ggagttgacc cagcaataat gggatatgga | 540 | |
| cctttctatg caacaaaagc agctattgaa aaagcaggtt ggacagttga tgaattagat | 600 | |
| ttaatagaat caaatgaagc ttttgcagct caaagtttag cagtagcaaa agatttaaaa | 660 | |
| tttgatatga ataaagtaaa tgtaaatgga ggagctattg cccttggtta tccaattgga | 720 | |
| gcatcaggtg caagaatact cgttactctt gtacacgcaa tgcaaaaaag agatgcaaaa | 780 | |
| aaaggcttag caactttatg tataggtggc ggacaaggaa cagcaatatt gctagaaaag | 840 | |
| tgctaggagg taagttatg gcgcctaccc gtaggatcc aggaggttag ttagaatgtt | 900 | |
| aaaagttctc agtctacgat ctgcgctcca gagagctgcc tcgacaagac aactagtcta | 960 | |
| tgaaggatat agaaaccctc ccgaggcaat acaattgaaa actgtcacaa ttgcggacaa | 1020 | |
| gccgtctgcg gatcaggtcc tggttcaatg gatagcagct ccaatcaacc cggcagactt | 1080 | |
| gaatcagatt caaggtgtgt accctgtgaa gccagcttta ccggcggttg gtggaaatga | 1140 | |
| aggatttggg aaagtgatta gtgttggatc caatgtgagc tcgattaaag ttggagacca | 1200 | |
| tgtaattccc gacagatctg gcctaggaac atggagagag ctcgggctcc accaggaaaa | 1260 | |
| tgatcttttt ccgattgata atactctttc catggagtat gctgcaacat tccaggtgaa | 1320 | |
| tcctcccaca gcttatcgta tgcttaaaga ctttatcgac ctgaaaaaag agacacagt | 1380 | |
| ggctcaaaac ggagccaatt cggctgtcgg gaagcacgtt attcaaattt gcaggatcct | 1440 | |
| tggcatcaaa actgtgaatg ttgtgagaag tcgtgataat ctggaagaat ggtgaaaga | 1500 | |
| gctgaaagat ttgggcgccg acgaagttat cacacaggaa gagttgtata gtcgaaagaa | 1560 | |
| gaaattccca ggagtcaagt tagcattaaa ctgcgttgga ggcagaagct ccctgttttt | 1620 | |
| ggcgagtctc ctggaccacg gaggatgtat ggtgacctac ggtggaatga gcaagcagcc | 1680 | |
| tgtcgattgt ccaaccgggc cactgatctt caaggatatc tcgcttcgtg gattctggat | 1740 | |
| gtcaagatgg tacgatattc agaaatcccc ggaaaagagg catgagatgt accaggagct | 1800 | |

```
tgccggttgg atgaagagtg gagagatcaa gaagcaggag attgtgaaga atcgattgga    1860
agatcatgca aaagctctcg atactgcgct gagcaaattc gacaagaagc aattcttcgt    1920
tttggaataa gcggccgc                                                  1938

<210> SEQ ID NO 43
<211> LENGTH: 3508
<212> TYPE: DNA
<213> ORGANISM: Artificial Sequence
<220> FEATURE:
<223> OTHER INFORMATION: codon optimized crotonyl-CoA reductase from
      Streptomyces collinus (Ccr_Sc(coCl))

<400> SEQUENCE: 43
ggccggccaa agtattgtta aaaagggagg tctgtttaat gagtattaaa agtgtagcgg      60
ttttaggtag tggaactatg tctcgtggaa ttgtgcaggc ttttgcagaa gcaggtatag    120
atgtaattat ccgtggaaga actgaaggta gtattggaaa aggtctagca gcagtaaaga    180
aagcttatga taaaaaagta tcaaagggga aaatttccca ggaagatgct gataaaatag    240
ttggaagagt aagtacaaca actgaacttg aaaaattggc tgattgtgat cttataatag    300
aagcagcatc agaggatatg aatataaaga aagactattt ggaaaatta gaagaaatat    360 gcaagcctga acaattttt gctactaata cttcttcatt atctataact gaagtagcaa    420
cagctacaaa gagaccagat aaattcatag gaatgcattt cttaatcca gcaaatgtta    480 tgaaattagt tgaaatcata agaggtatga atacttcaca gaaacttttt gatattataa    540
aagaagcttc cattaaaata ggaaaaactc ctgtagaagt tgcagaagct ccaggatttg    600
ttgtaaacaa gatattagta ccaatgatca atgaagcagt aggaattttg gcagaaggaa    660
tagcttcagc agaagatatc gatacagcta tgaaattagg cgctaatcac ccaatgggtc    720
ctttagcatt aggagatctt attggacttg atgtagttct tgcagttatg gatgtacttt    780
atagtgaaac tggagattca aaatatagag ctcatacatt acttagaaaa tatgtaagag    840
caggatggct tggaagaaaa tcaggaaaag gattcttcgc ttattaatta attaagttta    900
caagaatggc gctttaggag gattagtcat gaaagaagtt gtaatagcta gtgcagtaag    960
aacagcgatt ggatcttatg gaaagtctct taaggatgta ccagcagtag atttaggagc   1020
tacagctata aaggaagcag ttaaaaaagc aggaataaaa ccagaggatg ttaatgaagt   1080 catttagga atgttcttc aagcaggttt aggacagaat ccagcaagac aggcatcttt    1140
taaagcagga ttaccagttg aaattccagc tatgactatt aataaggttt gtggttcagg   1200
acttagaaca gttagcttag cagcacaaat tataaaagca ggagatgctg acgtaataat   1260
agcaggtggt atggaaaata tgtctagagc tccttactta gcgaataacg ctagatgggg   1320
atatagaatg ggaaacgcta aatttgttga tgaaatgatc actgacggat gtgtgggatgc  1380 atttaatgat taccacatgg aataacagc agaaaacata gctgagagat ggaacatttc   1440
aagagaagaa caagatgagt ttgctcttgc atcacaaaaa aaagctgaag aagctataaa   1500
atcaggtcaa tttaaagatg aaatagttcc tgtagtaatt aaaggcagaa agggagaaac   1560
tgtagttgat acagatgagc accctagatt tggatcaact atagaaggac ttgcaaaatt   1620
aaaacctgcc ttcaaaaaag atggaacagt tacagctggt aatgcatcag gattaaatga   1680
ctgtgcagca gtacttgtaa tcatgagtgc agaaaaagct aaagagcttg gagtaaaacc   1740
acttgctaag atagtttctt atggttcagc aggagttgac ccagcaataa tgggatatgg   1800
acctttctat gcaacaaaag cagctattga aaagcaggt tggacagttg atgaattaga   1860
```

| | |
|---|---|
| tttaatagaa tcaaatgaag cttttgcagc tcaaagttta gcagtagcaa aagatttaaa | 1920 |
| atttgatatg aataaagtaa atgtaaatgg aggagctatt gcccttggtt atccaattgg | 1980 |
| agcatcaggt gcaagaatac tcgttactct tgtacacgca atgcaaaaaa gagatgcaaa | 2040 |
| aaaaggctta gcaactttat gtataggtgg cggacaagga acagcaatat tgctagaaaa | 2100 |
| gtgctaggag gtaagtttat ggcgcctacc ccgtaggatc caggaggtta gttagagtga | 2160 |
| ccgtgaagga catcctggac gcgatccagt cgaaggacgc cacgtccgcc gacttcgccg | 2220 |
| ccctgcagct ccccgagtcg taccgtgcga tcaccgtgca aaggacgag acggagatgt | 2280 |
| tcgcgggtct ggagacccgt gacaaggacc cgagaaagtc gatccacctc gacgaggtgc | 2340 |
| ccgtgcccga actgggcccg gcgaagccc tggtggccgt catggcctcc tcggtcaact | 2400 |
| acaactcggt gtggacctcg atcttcgagc cggtgtcgac gttcgccttc ctggagagat | 2460 |
| acggcaagct gtcgccgctg accaagagac acgacctgcc gtaccacatc atcggctccg | 2520 |
| acctcgcggg cgtcgtcctg cgtaccggcc ccggcgtcaa cgcctggcag cccggtgacg | 2580 |
| aggtcgtcgc gcactgcctg agcgtcgagc tggagtcgcc cgacggccac gacgacacca | 2640 |
| tgctcgaccc cgagcagaga atctgggggct tcgagaccaa cttcggcggc ctcgcggaga | 2700 |
| tcgcgctggt caagacgaac cagctgatgc cgaagccgaa gcacctcacc tgggaggagg | 2760 |
| ccgcggcccc gggcctggtg aactccaccg cctaccgtca gctggtctcc agaaacggcg | 2820 |
| ccgccatgaa gcagggcgac aacgtcctga tctggggcgc gagcggcggg ctcggctcgt | 2880 |
| acgccacgca gttcgcgctc gcgggcggtg ccaacccgat ctgtgtcgtc tcctcgcccc | 2940 |
| agaaggcgga gatctgcaga tcgatgggcg ccgaggcgat catcgaccgt aacgccgagg | 3000 |
| gctacaagtt ctggaaggac gagcacaccc aggaccccaa ggagtggaag agattcggca | 3060 |
| agcgtatcag agagctgacc ggcggcgagg acatcgacat cgtcttcgag caccccggca | 3120 |
| gagagaccctt cggcgcctcc gtctacgtca cccgtaaggg cggcaccatc accacctgcg | 3180 |
| cctcgacctc gggctacatg cacgagtacg acaacaggta cctgtggatg tccctgaaga | 3240 |
| ggatcatcgg ctcgcacttc gccaactaca gagaggcgta cgaggccaac cgtctgatcg | 3300 |
| ccaagggcaa gatccacccg acgctgtcga agacgtactc cctggaggag accggccagg | 3360 |
| cggcgtacga cgtccaccgt aacctgcacc agggcaaggt cggcgtcctg tgcctcgcgc | 3420 |
| cggaggaagg cctcggcgtg agagacgcgg agatgcgtgc ccagcacatc gacgccatca | 3480 |
| acagattccg taacgtctga gcggccgc | 3508 |

<210> SEQ ID NO 44
<211> LENGTH: 938
<212> TYPE: DNA
<213> ORGANISM: Clostridium acetobutylicum

<400> SEQUENCE: 44

| | |
|---|---|
| gcgatcgccc attgctgcaa caggatcaga aatggatacg tgggcagtaa taataatat | 60 |
| ggatacaaac gaaaaactaa ttgcggcaca tccagatatg gctcctaagt tttctatatt | 120 |
| agatccaacg tatacgtata ccgtacctac caatcaaaca gcagcaggaa cagctgatat | 180 |
| tatgagtcat atatttgagg tgtattttag taatacaaaa acagcatatt tgcaggatag | 240 |
| aatggcagaa gcgttattaa gaacttgtat taaatatgga ggaatagctc ttgagaagcc | 300 |
| ggatgattat gaggcaagag ccaatctaat gtgggcttca agtcttgcga taatggact | 360 |
| tttaacatat ggtaaagaca ctaattggag tgtacactta atggaacatg aattaagtgc | 420 |

| | |
|---|---|
| ttattacgac ataacacacg gcgtagggct tgcaatttta acacctaatt ggatggagta | 480 |
| tattttaaat aatgatacag tgtacaagtt tgttgaatat ggtgtaaatg tttggggaat | 540 |
| agacaaagaa aaaaatcact atgacatagc acatcaagca atacaaaaaa caagagatta | 600 |
| ctttgtaaat gtactaggtt taccatctag actgagagat gttggaattg aagaagaaaa | 660 |
| attggacata atggcaaagg aatcagtaaa gcttacagga ggaaccatag gaaacctaag | 720 |
| accagtaaac gcctccgaag tcctacaaat attcaaaaaa tctgtgtaag gcgcgccact | 780 |
| taatgatttg ccagtaaaag agattgtttc tagctctcac attcttgcag atataatatt | 840 |
| gcctagagct gaagttatat atgattatct taagtaataa aaataagagt taccttaaat | 900 |
| ggtaactctt attttttaa tgtcgactca tagaattc | 938 |

<210> SEQ ID NO 45
<211> LENGTH: 1164
<212> TYPE: DNA
<213> ORGANISM: Escherichia coli

<400> SEQUENCE: 45

| | |
|---|---|
| atgaacaact ttaatctgca caccccaacc agaattctgt ttggtaaagg cgcaatcgct | 60 |
| ggtttaagag aacaaattcc tcacgatgct agagtattga ttacctacgg cggcggcagc | 120 |
| gtgaaaaaaa ccggcgttct cgatcaagtt ctggatgccc tgaaaggcat ggacgtgctg | 180 |
| gaatttggcg gtattgagcc aaaccccggct tatgaaacgc tgatgaacgc cgtgaaactg | 240 |
| gttagagaac agaaagtgac tttcctgctg gcggttggcg gcggttctgt actggacggc | 300 |
| accaaaattta tcgccgcagc ggctaactat ccggaaaata tcgatccgtg gcacattctg | 360 |
| caaacgggcg gtaaagagat taaaagcgcc atcccgatgg gctgtgtgct gacgctgcca | 420 |
| gcaaccggtt cagaatccaa cgcaggcgcg gtgatctccc gtaaaaccac aggcgacaag | 480 |
| caggcgttcc attctgccca tgttcagccg gtatttgccg tgctcgatcc ggtttatacc | 540 |
| tacacccctgc cgccgcgtca ggtggctaac ggcgtagtgg acgcctttgt acacaccgtg | 600 |
| gaacagtatg ttaccaaacc ggttgatgcc aaaattcagg accgtttcgc agaaggcatt | 660 |
| ttgctgacgc taatcgaaga tggtccgaaa gccctgaaag agccagaaaa ctacgatgtg | 720 |
| agagccaacg tcatgtgggc ggcgactcag gcgctgaacg gtttgattgg cgctggcgta | 780 |
| ccgcaggact gggcaacgca tatgctgggc acgaactga ctgcgatgca cggtctggat | 840 |
| cacgcgcaaa cactggctat cgtcctgcct gcactgtgga tgaaaaaag agataccaag | 900 |
| agagctaagc tgctgcaata tgctgaaaga gtctggaaca tcactgaagg ttccgatgat | 960 |
| gagcgtattg acgccgcgat tgccgcaacc agaaatttct ttgagcaatt aggcgtgccg | 1020 |
| acccacctct ccgactacgg tctggacggc agctccatcc cggctttgct gaaaaaactg | 1080 |
| gaagagcacg gcatgaccca actgggcgaa aatcatgaca ttacgttgga tgtcagcaga | 1140 |
| cgtatatacg aagccgccag ataa | 1164 |

<210> SEQ ID NO 46
<211> LENGTH: 53
<212> TYPE: DNA
<213> ORGANISM: Artificial Sequence
<220> FEATURE:
<223> OTHER INFORMATION: 2072_etfBA_fp

<400> SEQUENCE: 46

| | |
|---|---|
| cttgctttaa gcaaactact attttcatta tgaactcctc ctatttattt aaa | 53 |

```
<210> SEQ ID NO 47
<211> LENGTH: 30
<212> TYPE: DNA
<213> ORGANISM: Artificial Sequence
<220> FEATURE:
<223> OTHER INFORMATION: 2072_etfBA_rp

<400> SEQUENCE: 47
ttaaagattt aaagctttaa cttgttctac                                    30

<210> SEQ ID NO 48
<211> LENGTH: 53
<212> TYPE: DNA
<213> ORGANISM: Artificial Sequence
<220> FEATURE:
<223> OTHER INFORMATION: 2072_cat3_fp

<400> SEQUENCE: 48
acttatgaaa tagattgaaa tggtttatct gttaccccgt aggatccagg agg           53

<210> SEQ ID NO 49
<211> LENGTH: 38
<212> TYPE: DNA
<213> ORGANISM: Artificial Sequence
<220> FEATURE:
<223> OTHER INFORMATION: 2072_cat3_rp_BspEI

<400> SEQUENCE: 49
gattccggat cagtatatat atcattttta taattaag                            38

<210> SEQ ID NO 50
<211> LENGTH: 52
<212> TYPE: DNA
<213> ORGANISM: Artificial Sequence
<220> FEATURE:
<223> OTHER INFORMATION: 2072_fp_RBS_KasI

<400> SEQUENCE: 50
aggggcgcct accccgtagg atccaggagg ttagttagaa tgaaaatagt ag            52

<210> SEQ ID NO 51
<211> LENGTH: 4080
<212> TYPE: DNA
<213> ORGANISM: Artificial Sequence
<220> FEATURE:
<223> OTHER INFORMATION: pATh-LEM-02

<400> SEQUENCE: 51
ggatccagga ggttagttag aatgaaagaa gttgtaatag ctagtgcagt aagaacagcg    60
attggatctt atggaaagtc tcttaaggat gtaccagcag tagatttagg agctacagct    120 ataaggaag  cagttaaaaa agcaggaata aaaccagagg atgttaatga agtcatttta    180
ggaaatgttc ttcaagcagg tttaggacag aatccagcaa gacaggcatc ttttaaagca    240
ggattaccag ttgaaattcc agctatgact attaataagg tttgtggttc aggacttaga    300
acagttagct tagcagcaca aattataaaa gcaggagatg ctgacgtaat aatagcaggt    360
ggtatggaaa atatgtctag agctccttac ttagcgaata cgctagatg gggatataga    420 atgggaaacg ctaaatttgt tgatgaaatg atcactgacg gattgtggga tgcatttaat    480
gattaccaca tgggaataac agcagaaaac atagctgaga gatggaacat ttcaagagaa    540
gaacaagatg agtttgctct tgcatcacaa aaaaagctg aagaagctat aaaatcaggt    600
caatttaaag atgaaatagt tcctgtagta attaaaggca gaaagggaga aactgtagtt    660
```

```
gatacagatg agcaccctag atttggatca actatagaag gacttgcaaa attaaaacct    720
gccttcaaaa aagatggaac agttacagct ggtaatgcat caggattaaa tgactgtgca    780
gcagtacttg taatcatgag tgcagaaaaa gctaaagagc ttggagtaaa accacttgct    840
aagatagttt cttatggttc agcaggagtt gacccagcaa taatgggata tggacctttc    900
tatgcaacaa aagcagctat tgaaaaagca ggttggacag ttgatgaatt agatttaata    960
gaatcaaatg aagcttttgc agctcaaagt ttagcagtag caaaagattt aaaatttgat   1020
atgaataaag taaatgtaaa tggaggagct attgcccttg gtcatccaat tggagcatca   1080
ggtgcaagaa tactcgttac tcttgtacac gcaatgcaaa aagagatgc aaaaaaaggc    1140 ttagcaactt tatgtatagg tggcggacaa ggaacagcaa tattgctaga aaagtgctag   1200
aaagtattgt taaaaaggga ggtctgtttta atgagtatta aaagtgtagc ggttttaggt   1260
agtggaacta tgtctcgtgg aattgtgcag gcttttgcag aagcaggtat agatgtaatt   1320
atccgtggaa gaactgaagg tagtattgga aaaggtctag cagcagtaaa gaaagcttat   1380
gataaaaaag tatcaagggg gaaaatttcc caggaagatg ctgataaaat agttggaaga   1440
gtaagtacaa caactgaact tgaaaaattg gctgattgtg atcttataat agaagcagca   1500
tcagaggata tgaatataaa gaaagactat tttggaaaat tagaagaaat atgcaagcct   1560
gaaacaattt ttgctactaa tacttcttca ttatctataa ctgaagtagc aacagctaca   1620
aagagaccag ataaattcat aggaatgcat ttctttaatc cagcaaatgt tatgaaatta   1680
gttgaaatca taagaggtat gaatacttca caagaaactt ttgatattat aaaagaagct   1740
tccattaaaa taggaaaaac tcctgtagaa gttgcagaag ctccaggatt tgttgtaaac   1800
aagatattag taccaatgat caatgaagca gtaggaattt tggcagaagg aatagcttca   1860
gcagaagata tcgatacagc tatgaaatta ggcgctaatc acccaatggg tcctttagca   1920
ttaggagatc ttattggact tgatgtagtt cttgcagtta tggatgtact ttatagtgaa   1980
actggagatt caaaatatag agctcataca ttacttagaa aatatgtaag agcaggatgg   2040
cttggaagaa aatcaggaaa aggattcttc gcttattaat taattaagtt tacaagaatg   2100
gcgctttagg aggattagtc atggaattta aaaatatcat tcttgaaaag gatggaaatg   2160
tggcttcaat aacgttgaat agacctaagg cattaaatgc attaaatgca gcaactttaa   2220
aagagataga tgccgcaata aacgacattg ctgaagatga taacgtatat gctgtgataa   2280
ttactgggtc aggtaaagct tttgtagcag gagcagatat agctgagatg aaagatctta   2340
ctgcagttga gggaagaaag ttttcagttc ttggcaataa aatatttaga aaattagaaa   2400
atttagaaaa accagttata gcagctataa atggatttgc actgggtggt ggctgtgaat   2460
tgtcattgtc ttgcgatata agaatagctt catcaaaggc taagtttggt caaccagagg   2520
ttggtcttgg aattactcca gggtttggag gtactcaaag acttgcaaga gcaataggcg   2580
ttggtatggc taaggaactt atatataccg gaaaagtaat taatgctgaa gaggcattaa   2640
gaataggttt ggtaaataaa gtagttgagc cagataaatt attggaagaa gctaaagctt   2700
tagtagatgc tattattgtt aatgcaccta gctgttag aatgtgtaag gctgctataa     2760
atcaaggact tcagtgtgat atagatacag gtgtagctta tgaagcagaa gtatttgggg   2820
aatgttttgc tacagaagat agagtagaag gaatgacagc atttgtagaa aaaagagaca   2880
aggcttttaa aaataagtaa accggtgagg taagtttata tggatttttac attaacaaac   2940 gagcaaaaat ttgtagaaca aatggtaagt gaatttactg aaaatgaagt taaacctata   3000
gctgctgaaa tagatgaaac agaaaggttt cctcttgaga cagtagaaaa atttgctaaa   3060
```

```
tacggaatga tgggtatgcc ttttccagtt gaatacggcg gctcaggtac agattattta    3120
tcctatataa tagcagtaga aggacttgca aagagttgta cttcatcatc aactatattg    3180
tcagcacata cttcactttg tgcagcacct atttatgatt ggggtacaga agaacagaaa    3240
caaaaatact tagttcctct tgcaaaggga gaaaaacttg gagcatttgg tttaactgaa    3300
cctaatgcag gtactgatgc tgctggacag cagacaacag ctgttttaga aggggatcat    3360
tatgtattaa atggacaaaa aatatttatt acaaatggtg catatgcaga tacttttgta    3420
atatttgcaa tgacagacag aagcaagggt acaagaggaa taacagcatt tatagttgaa    3480
aaagatttcc ctggtttctc cataggaaaa tctgaagata agttgggaat tagagcttcc    3540
tcaactacag aacttatatt tgagaattgc atagttccaa aagaaaatat gttaggaaaa    3600
gaaggaaaag gatttactgt agcaatgcat actcttgatg gaggaagaat tggtatagca    3660
gcacaagcgt taggtttagc agaaggcgca ttagctgaag cacttaatta tatgaaagaa    3720
agaaaacaat ttggaaaagc tctttacaaa ttccagggat tagcatggat ggttgcagaa    3780
ttagatacta aaatagaagc tgttaaacaa cttgtttata aagcagcagt aaataaacaa    3840
atgggtcttc catattcagt ggaagctgca agagctaaat tagctgcggc tactgtagct    3900
atggaaacaa ctactaaagt tgttcaaatc tttggtggat atggattcac taaggattat    3960
ccagtagaaa gaatgatgag agatgctaag ataactgaaa tatatgaagg aacttcacaa    4020
gtacaaaaga tggttatttc agcaaattta tttaaataaa tttaaatttt aagggqcgcc    4080

<210> SEQ ID NO 52
<211> LENGTH: 1511
<212> TYPE: DNA
<213> ORGANISM: Artificial Sequence
<220> FEATURE:
<223> OTHER INFORMATION: fragment of cat3 (EcoRI and KasI cut)

<400> SEQUENCE: 52
ggcgcctacc ccgtaggatc caggaggtta gttagaatgg ttttttaaaaa ttggcaggat      60 ctttataaaa gtaaaattgt tagtgcagac gaagctgtat ctaaagtaag ctgtggagat     120
agcataattt taggcaatgc ttgtggagca tctcttacac ttttagatgc cttggctgca     180
aataaggaaa agtataagag tgtaaagata cacaatctta tacttaatta taaaaatgat     240
atatatactg atccggaatc agaaaagtat attcatggaa atactttctt tgtaagtgga     300
ggtacaaagg aagcagttaa ttgtaataga acagattata ctccatgctt tttttatgaa     360
ataccaaaat tattaaaaca aaagtatata aatgcagatg tagctttttat tcaagtaagt     420 aagcctgata gccatggata ctgtagcttt ggagtatcaa ccgattattc acaggcaatg     480
gtacagtctg caaagcttat aattgcagaa gtaaacgatc agatgccaag agttttagga     540
gacaatttta tacacatttc tgatatggat tacatagtag aaagttcacg tccaattcta     600
gaattgactc ctcctaaaat aggagaagta gagaagacaa taggaaaaata ctgtgcatct     660 cttgtagaag atggttctac acttcagctt ggaataggag ctattccaga tgcagtactt     720
ttattcttga aggataaaaa ggatttgggt atacattcag aaatgatatc cgatggtgtt     780
gttgaattag ttgaagcagg ggtaattaca aataagaaaa agtcccttca tccaggaaaa     840
ataattatta cattcttaat gggaactaag aaattatatg atttcataaa tgataatcct     900
atggtagaag gataccctgt agattatgta aatgatccta aggttattat gcaaaattct     960
aagatggtat gtataaactc ctgtgtagaa gtggatttca caggacaagt gtgtgctgaa    1020
```

| | |
|---|---:|
| agtgtaggat ttaaacaaat aagcggtgta ggtggacaag ttgattacat gagaggagct | 1080 |
| agcatggctg atggaggaaa atcaattctt gctataccat ctactgcagc tggcggcaaa | 1140 |
| atttcaagaa tagttcctat tttaactgaa ggagcggggg ttactacttc aagatatgat | 1200 |
| gttcaatatg ttgttacaga atatggtatt gcacttctca agggcaaatc cataagagaa | 1260 |
| agagctaagg agcttataaa aattgcacat cctaaattta gggaagaatt aacagctcaa | 1320 |
| tttgaaaaaa gattcagttg taagcttta aacttaatgat ttgccagtaa aagagattgt | 1380 |
| ttctagctct cacattcttg cagatataat attgcctaga gctgaagtta tatatgatta | 1440 |
| tcttaagtaa taaaaataag agttaccta aatggtaact cttatttttt taatgtcgac | 1500 |
| tcatagaatt c | 1511 |

<210> SEQ ID NO 53
<211> LENGTH: 2927
<212> TYPE: DNA
<213> ORGANISM: Artificial Sequence
<220> FEATURE:
<223> OTHER INFORMATION: pATh-Syn4-03

<400> SEQUENCE: 53

| | |
|---|---:|
| ggatccagga ggttagttag aatggaattt aaaaatatca ttcttgaaaa ggatggaaat | 60 |
| gtggcttcaa taacgttgaa tagacctaag gcattaaatg cattaaatgc agcaacttta | 120 |
| aaagagatag atgccgcaat aaacgacatt gctgaagatg ataacgtata tgctgtgata | 180 |
| attactgggt caggtaaagc ttttgtagca ggagcagata tagctgagat gaaagatctt | 240 |
| actgcagttg agggaagaaa gttttcagtt cttggcaata aaatatttag aaaattagaa | 300 |
| aatttagaaa aaccagttat agcagctata aatggatttg cactgggtgg tggctgtgaa | 360 |
| ttgtcattgt cttgcgatat aagaatagct tcatcaaagg ctaagtttgg tcaaccagag | 420 |
| gttggtcttg aattactccc agggtttgga ggtactcaaa gacttgcaag agcaataggc | 480 |
| gttggtatgg ctaaggaact tatatatacc ggaaaagtaa ttaatgctga agaggcatta | 540 |
| agaataggtt tggtaaataa agtagttgag ccagataaat tattggaaga agctaaagct | 600 |
| ttagtagatg ctattattgt taatgcacct atagctgtta aatgtgtaa ggctgctata | 660 |
| aatcaaggac ttcagtgtga tatagataca ggtgtagctt atgaagcaga agtatttggg | 720 |
| gaatgttttg ctacagaaga tagagtagaa ggaatgacag catttgtaga aaaaagagac | 780 |
| aaggctttta aaataagta aggccggcca agtattgtt aaaagggag gtctgtttaa | 840 |
| tgagtattaa aagtgtagcg ttttaggta gtggaactat gtctcgtgga attgtgcagg | 900 |
| cttttgcaga agcaggtata gatgtaatta ccgtggaag aactgaaggt agtattggaa | 960 |
| aaggtctagc agcagtaaag aaagcttatg ataaaaagt atcaaagggg aaaatttccc | 1020 |
| aggaagatgc tgataaaata gttggaagag taagtacaac aactgaactt gaaaaattgg | 1080 |
| ctgattgtga tcttataata gaagcagcat cagaggatat gaatataaag aaagactatt | 1140 |
| ttggaaaatt agaagaaata tgcaagcctg aaacaatttt tgctactaat acttcttcat | 1200 |
| tatctataac tgaagtagca acagctacaa agagaccaga taattcata ggaatgcatt | 1260 |
| tctttaatcc agcaaatgtt atgaaattag ttgaaatcat aagaggtatg aatacttcac | 1320 |
| aagaaacttt tgatattata aagaagcttc ccattaaaat aggaaaaact cctgtagaag | 1380 |
| ttgcagaagc tccaggattt gttgtaaaca agatattagt accaatgatc aatgaagcag | 1440 |
| taggaatttt ggcagaagga atagcttcag cagaagatat cgatacagct atgaaattag | 1500 |
| gcgctaatca cccaatgggt cctttagcat taggagatct tattggactt gatgtagttc | 1560 |

-continued

```
ttgcagttat ggatgtactt tatagtgaaa ctggagattc aaaatataga gctcatacat    1620
tacttagaaa atatgtaaga gcaggatggc ttggaagaaa tcaggaaaaa ggattcttcg    1680
cttattaatt aattaagttt acaagaatgg cgctttagga ggattagtca tgaaagaagt    1740
tgtaatagct agtgcagtaa gaacagcgat tggatcttat ggaaagtctc ttaaggatgt    1800
accagcagta gatttaggag ctacagctat aaaggaagca gttaaaaaag caggaataaa    1860
accagaggat gttaatgaag tcattttagg aaatgttctt caagcaggtt taggacagaa    1920
tccagcaaga caggcatctt ttaaagcagg attaccagtt gaaattccag ctatgactat    1980
taataaggtt tgtggttcag gacttagaac agttagctta gcagcacaaa ttataaaagc    2040
aggagatgct gacgtaataa tagcaggtgg tatggaaaat atgtctagag ctccttactt    2100
agcgaataac gctagatggg gatatagaat gggaaacgct aaatttgttg atgaaatgat    2160
cactgacgga ttgtgggatg catttaatga ttaccacatg gaataacag cagaaaacat     2220 agctgagaga tggaacattt caagagaaga acaagatgag tttgctcttg catcacaaaa    2280
aaaagctgaa gaagctataa atcaggtca atttaaagat gaaatagttc ctgtagtaat    2340
taaaggcaga aagggagaaa ctgtagttga tacagatgag cacctagat ttggatcaac     2400 tatagaagga cttgcaaaat taaaacctgc cttcaaaaaa gatggaacag ttacagctgg    2460
taatgcatca ggattaaatg actgtgcagc agtacttgta atcatgagtg cagaaaaagc    2520
taaagagctt ggagtaaaac cacttgctaa gatagtttct tatggttcag caggagttga    2580
cccagcaata atgggatatg gacctttcta tgcaacaaaa gcagctattg aaaaagcagg    2640
ttggacagtt gatgaattag atttaataga atcaaatgaa gcttttgcag ctcaaagttt    2700
agcagtagca aaagatttaa aatttgatat gaataaagta aatgtaaatg gaggagctat    2760
tgcccttggt catccaattg gagcatcagg tgcaagaata ctcgttactc ttgtacacgc    2820
aatgcaaaaa agagatgcaa aaaaggctt agcaactta tgtataggtg gcggacaagg     2880
aacagcaata ttgctagaaa agtgctagga ggtaagttta tggcgcc                  2927
```

<210> SEQ ID NO 54
<211> LENGTH: 1519
<212> TYPE: DNA
<213> ORGANISM: Artificial Sequence
<220> FEATURE:
<223> OTHER INFORMATION: cat3 fragment

<400> SEQUENCE: 54

```
ggcgcctacc ccgtaggatc caggaggtta gttagaatgg ttttaaaaa ttggcaggat       60 ctttataaaa gtaaaattgt tagtgcagac gaagctgtat ctaaagtaag ctgtggagat     120
agcataattt taggcaatgc ttgtggagca tctcttacac ttttagatgc cttggctgca    180
aataaggaaa agtataagag tgtaaagata cacaatctta tacttaatta taaaaatgat    240
atatatactg atccggaatc agaaaagtat attcatggaa atactttctt tgtaagtgga    300
ggtacaaagg aagcagttaa ttgtaataga acagattata ctccatgctt ttttatgaa    360 ataccaaaat tattaaaaca aaagtatata aatgcagatg tagcttttat tcaagtaagt    420
aagcctgata gccatggata ctgtagcttt ggagtatcaa ccgattattc acaggcaatg    480
gtacagtctg caaagcttat aattgcagaa gtaaacgatc agatgccaag agttttagga    540 gacaattta tacacatttc tgatatggat tacatagtag aaagttcacg tccaattcta    600
gaattgactc ctcctaaaat aggagaagta gagaagacaa taggaaaata ctgtgcatct    660
```

```
cttgtagaag atggttctac acttcagctt ggaataggag ctattccaga tgcagtactt    720
ttattcttga aggataaaaa ggatttgggt atacattcag aaatgatatc cgatggtgtt    780
gttgaattag ttgaagcagg ggtaattaca aataagaaaa agtcccttca tccaggaaaa    840
ataattatta cattcttaat gggaactaag aaattatatg atttcataaa tgataatcct    900
atggtagaag ataccctgt agattatgta aatgatccta aggttattat gcaaaattct     960
aagatggtat gtataaactc ctgtgtagaa gtggatttca caggacaagt gtgtgctgaa   1020
agtgtaggat ttaaacaaat aagcggtgta ggtggacaag ttgattacat gagaggagct   1080
agcatggctg atggaggaaa atcaattctt gctataccat ctactgcagc tggcggcaaa   1140
atttcaagaa tagttcctat tttaactgaa ggagcggggg ttactacttc aagatatgat   1200
gttcaatatg ttgttacaga atatggtatt gcacttctca agggcaaatc cataagagaa   1260
agagctaagg agcttataaa aattgcacat cctaaattta gggaagaatt aacagctcaa   1320
tttgaaaaaa gattcagttg taagctttaa gcgatcgcac ttaatgattt gccagtaaaa   1380
gagattgttt ctagctctca cattcttgca gatataaat tgcctagagc tgaagttata   1440
tatgattatc ttaagtaata aaaataagag ttaccttaaa tggtaactct tattttttta   1500
atgtcgactc atagaattc                                               1519
```

<210> SEQ ID NO 55
<211> LENGTH: 4385
<212> TYPE: DNA
<213> ORGANISM: Artificial Sequence
<220> FEATURE:
<223> OTHER INFORMATION: vector pATh-LEM-15

<400> SEQUENCE: 55

```
gaaaagtgct aggaggtaag tttatggcgc cgaggtaagt ttatatggat tttaatttaa     60
caagagaaca agaattagta agacagatgg ttagagaatt tgctgaaaat gaagttaaac    120
ctatagcagc agaaattgat gaaacagaaa gatttccaat ggaaaatgta agaaaatgg    180 gtcagtatgg tatgatggga attccatttt caaaagagta tggtggcgca ggtggagatg    240
tattatctta tataatcgcc gttgaggaat tatcaaaggt ttgcggtact acaggagtta    300
ttctttcagc acatacatca ctttgtgctt cattaataaa tgaacatggt acagaagaac    360
aaaaacaaaa atatttagta cctttagcta aaggtgaaaa aataggtgct tatgattga    420 ctgagccaaa tgcaggaaca gattctggag cacaacaaac agtagctgta cttgaaggag    480
atcattatgt aattaatggt tcaaaaatat tcataactaa tggaggagtt gcagatactt    540
ttgttatatt tgcaatgact gacagaacta aaggaacaaa aggtatatca gcatttataa    600
tagaaaaagg cttcaaaggt ttctctattg gtaaagttga acaaaagctt ggaataagag    660
cttcatcaac aactgaactt gtatttgaag atatgatagt accagtagaa aacatgattg    720
gtaaagaagg aaaaggcttc cctatagcaa tgaaaactct tgatggagga agaattggta    780
tagcagctca agctttaggt atagctgaag gtgctttcaa cgaagcaaga gcttacatga    840
aggagagaaa acaatttgga agaagccttg acaaattcca aggtcttgca tggatgatgg    900
cagatatgga tgtagctata gaatcagcta gatatttagt atataaagca gcatatctta    960
aacaagcagg acttccatac acagttgatg ctgcaagagc taagcttcat gctgcaaatg   1020
tagcaatgga tgtaacaact aaggcagtac aattatttgg tggatacgga tatcaaaaag   1080
attatccagt tgaaagaatg atgagagatg ctaagataac tgaaatatat gaaggaactt   1140
cagaagttca gaaattagtt atttcaggaa aaatttttag ataatttaag gaggttaaga   1200
```

```
ggatgaatat agttgtttgt ttaaaacaag ttccagatac agcggaagtt agaatagatc    1260
cagttaaggg aacacttata agagaaggag ttccatcaat aataaatcca gatgataaaa    1320
acgcacttga ggaagcttta gtattaaaag ataattatgg tgcacatgta acagttataa    1380
gtatgggacc tccacaagct aaaaatgctt tagtagaagc tttggctatg ggtgctgatg    1440
aagctgtact tttaacagat agagcatttg gaggagcaga tacacttgcg acttcacata    1500
caattgcagc aggaattaag aagctaaaat atgatatagt ttttgctgga aggcaggcta    1560
tagatggaga tacagctcag gttggaccag aaatagctga gcatcttgga atacctcaag    1620
taacttatgt tgagaaagtt gaagttgatg agatactttt aaagattaga aaagcttggg    1680
aagatggata tgaagttgtt gaagttaaga caccagttct tttaacagca attaaagaat    1740
taaatgttcc aagatatatg agtgtagaaa aaatattcgg agcatttgat aaagaagtaa    1800
aaatgtggac tgccgatgat atagatgtag ataaggctaa tttaggtctt aaaggttcac    1860
caactaaagt taagagtca tcaactaaag aagttaaagg acagggagaa gttattgata    1920
agcctgttaa ggaagcagct gcatatgttg tctcaaaatt aaaagaagaa cactatattt    1980
aagttaggag ggattttttca atgaataaag cagattacaa gggcgtatgg gtgtttgctg    2040
aacaaagaga cggagaatta caaaaggtat cattggaatt attaggtaaa ggtaaggaaa    2100
tggctgagaa attaggcgtt gaattaacag ctgttttact tggacataat actgaaaaaa    2160
tgtcaaagga tttattatct catggagcag ataaggtttt agcagcagat aatgaacttt    2220
tagcacattt ttcaacagat ggatatgcta agttatatg tgatttagtt aatgaaagaa    2280
agccagaaat attattcata ggagctactt tcataggaag agatttagga ccaagaatag    2340
cagcaagact ttctactggt ttaactgctg attgtacatc acttgacata gatgtagaaa    2400
atagagattt attggctaca agaccagcgt ttggtggaaa tttgatagct acaatagttt    2460
gttcagacca cagaccacaa atggctacag taagacctgg tgtgtttgaa aaattacctg    2520
ttaatgatgc aaatgtttct gatgataaaa tagaaaaagt tgcaattaaa ttaacagcat    2580
cagacataag aacaaaagtt tcaaaagttg ttaagcttgc taaagatatt gcagatatcg    2640
gagaagctaa ggtattagtt gctggtggta gaggagttgg aagcaaagaa aacttttgaaa    2700 aacttgaaga gttagcaagt ttacttggtg gaacaatagc cgcttcaaga gcagcaatag    2760
aaaaagaatg ggttgataag gaccttcaag taggtcaaac tggtaaaact gtaagaccaa    2820
ctctttatat tgcatgtggt atatcaggag ctatccagca tttagcaggt atgcaagatt    2880
cagattacat aattgctata aataaagatg tagaagcccc aataatgaag gtagcagatt    2940
tggctatagt tggtgatgta aataaagttg taccagaatt aatagctcaa gttaaagctg    3000
ctaataatta agcggccgct accccgtagg atccaggagg ttagttagaa tggttttttaa    3060 aaattggcag gatctttata aaagtaaaat tgttagtgca gacgaagctg tatctaaagt    3120
aagctgtgga gatagcataa ttttaggcaa tgcttgtgga gcatctctta cacttttaga    3180
tgccttggct gcaaataagg aaaagtataa gagtgtaaag atacacaatc ttatacttaa    3240
ttataaaaat gatatatata ctgatccgga atcagaaaag tatattcatg gaaatacttt    3300
ctttgtaagt ggaggtacaa aggaagcagt taattgtaat agaacagatt atactccatg    3360 cttttttttat gaaataccaa aattattaaa acaaaagtat ataaatgcag atgtagcttt    3420
tattcaagta agtaagcctg atagccatgg atactgtagc tttggagtat caaccgatta    3480
ttcacaggca atggtacagt ctgcaaagct tataattgca gaagtaaacg atcagatgcc    3540
```

| | |
|---|---:|
| aagagtttta ggagacaatt ttatacacat ttctgatatg gattacatag tagaaagttc | 3600 |
| acgtccaatt ctagaattga ctcctcctaa aataggagaa gtagagaaga caataggaaa | 3660 |
| atactgtgca tctcttgtag aagatggttc tacacttcag cttggaatag gagctattcc | 3720 |
| agatgcagta cttttattct tgaaggataa aaaggatttg ggtatacatt cagaaatgat | 3780 |
| atccgatggt gttgttgaat tagttgaagc agggtaatt acaaataaga aaagtccct | 3840 |
| tcatccagga aaaataatta ttacattctt aatgggaact aagaaattat atgatttcat | 3900 |
| aaatgataat cctatggtag aaggataccc tgtagattat gtaaatgatc ctaaggttat | 3960 |
| tatgcaaaat tctaagatgg tatgtataaa ctcctgtgta gaagtggatt tcacaggaca | 4020 |
| agtgtgtgct gaaagtgtag gatttaaaca aataagcggt gtaggtggac aagttgatta | 4080 |
| catgagagga gctagcatgg ctgatggagg aaaatcaatt cttgctatac catctactgc | 4140 |
| agctggcggc aaaatttcaa gaatagttcc tattttaact gaaggagcgg gggttactac | 4200 |
| ttcaagatat gatgttcaat atgttgttac agaatatggt attgcacttc tcaagggcaa | 4260 |
| atccataaga gaaagagcta aggagcttat aaaaattgca catcctaaat ttagggaaga | 4320 |
| attaacagct caatttgaaa aaagattcag ttgtaagctt taagcgccac ttaatgattt | 4380 |
| gccag | 4385 |

<210> SEQ ID NO 56
<211> LENGTH: 4512
<212> TYPE: DNA
<213> ORGANISM: Artificial Sequence
<220> FEATURE:
<223> OTHER INFORMATION: vector pATh-LEM-16

<400> SEQUENCE: 56

| | |
|---|---:|
| gcgcctaccc cgtaggatcc aggaggttag ttagaatgga ttttacatta acaaacgagc | 60 |
| aaaaatttgt agaacaaatg gtaagtgaat ttactgaaaa tgaagttaaa cctatagctg | 120 |
| ctgaaataga tgaaacagaa aggtttcctc ttgagacagt agaaaaattt gctaaatacg | 180 |
| gaatgatggg tatgcctttt ccagttgaat acggcggctc aggtacagat tatttatcct | 240 |
| atataatagc agtagaagga cttgcaaaga gttgtacttc atcatcaact atattgtcag | 300 |
| cacatacttc actttgtgca gcacctattt atgattgggg tacagaagaa cagaaacaaa | 360 |
| aatacttagt tcctcttgca aagggagaaa aacttggagc atttggttta actgaaccta | 420 |
| atgcaggtac tgatgctgct ggacagcaga caacagctgt tttagaaggg gatcattatg | 480 |
| tattaaatgg acaaaaaata tttattacaa atggtgcata tgcagatact tttgtaatat | 540 |
| ttgcaatgac agacagaagc aagggtacaa gaggaataac agcatttata gttgaaaaag | 600 |
| atttccctgg tttctccata ggaaaatctg aagataagtt gggaattaga gcttcctcaa | 660 |
| ctacagaact tatatttgag aattgcatag ttccaaaaga aaatatgtta ggaaaagaag | 720 |
| gaaaaggatt tactgtagca atgcatactc ttgatggagg aagaattggt atagcagcac | 780 |
| aagcgttagg tttagcagaa ggcgcattag ctgaagcact taattatatg aaagaaagaa | 840 |
| aacaatttgg aaaagctctt acaaattcc agggattagc atggatggtt gcagaattag | 900 |
| atactaaaat agaagctgtt aaacaacttg tttataaagc agcagtaaat aaacaaatgg | 960 |
| gtcttccata ttcagtggaa gctgcaagag ctaaattagc tgcggctact gtagctatgg | 1020 |
| aaacaactac taaagttgtt caatctttg gtggatatgg attcactaag gattatccag | 1080 |
| tagaaagaat gatgagagat gctaagataa ctgaaatata tgaaggaact tcacaagtac | 1140 |
| aaaagatggt tatttcagca aatttattta aataaatagg aggagttcat aatgaaaata | 1200 |

```
gtagtttgct taaagcaagt accagataca actgaagtta aaatagatcc aaaaacagga    1260
acattaataa gagaaggcgt tccatcaata ataaacccag atgataaaaa tgcacttgaa    1320
gaatcaattg ctttaaaaga aaaagtaggg ggtacagtta cagtagtaag catggggcct    1380
ccacaggcag tggatgcact tagagaagct ctagctatgg gagctgatga agcaatatta    1440
gtttcagaca gagcttttgc aggagcagat actcaagcta cttcctatgc attagcagga    1500
gcacttaaaa atttagaata tgatttaata tttgcaggaa gacaagctat agatggagat    1560
actgcacagg ttggacctca aatagcagaa aaattaggaa tacctcagat aacatatgta    1620 gaaaagttg atgtagatgg agatacttta acagttcaaa gagcttggga agatggatat    1680
gaagtagcaa aaattaaaac tccatgcatg ttaactgcta taaaagagtt aaatcaacca    1740
agatatatga acatgaagaa catatttgaa gttttcaaga agaagttaa aatatggagt    1800 gctgacgact tagatgtaga taaaaataaa cttggtctta atggttcctg cacaaaagtt    1860
aagagatcac atacaaaaga agcaaaagga gcaggagaaa tcgttaataa accaataaaa    1920
gaagcagtag catattcaat ttcaaaatta agagaaaaac atgtcattta atatatagga    1980
ggggtttaga atgaacttag cagaatacaa aggcgtatgg gtatttgctg aacaaaggga    2040
tggagaacta caaaaagtag cacttcaatt agttggaaaa ggaagagaat tggcagacac    2100
tttaggagta gaattaactg ctgtattact tggtagtgaa gtagatgatt tggcaaaaga    2160
attagttgca tatggagcag acaatgtttt atacgcagat agtcctcttt taaaacatta    2220
tactacagat ggatacacta aagtaataga tgaacttata aaagaaagaa accagaaat    2280 attacttata ggagctacat ttatcggaag agacttagga ccaagagttg caggtagagt    2340
ttttacaggt cttacagcag actgtacagg acttgatata gatgaggcaa caaaaaattt    2400
gatgatgaca agacctgcat ttggtggaaa cttaatggca actatagctt gcgaaaaaac    2460
aagacctcaa atgtcaacag taagaccagg agttttttaat gcgcttccaa gagatgcttc    2520
aagaactgga aaaatagaaa aaatagctgc aaatgttgca aaagatgaca tcagaattga    2580
agtgcttgaa gtagttaaat ctgctggcga tacaatagat atttcagaag cagatgtaat    2640
tgtatcaggt ggaagaggac ttggtggtcc agatggattc aaagttctta agaattagc    2700 agatttatta ggtggaacta taggtggatc ccgtgcaact atagatgctg gctggataga    2760
taagagctat caggttggac aaactggtaa aacagtaaga ccaggtcttt atattgcatg    2820
cggaatatca ggtcaaatac aacatttagc tggtatgcag gatagtggat ttatcgtagc    2880
tatcaataaa gatgaaaacg ctccaatgat gcaagtagcg gatcttgcaa ttgtaggaga    2940
tttatataag gttgttccag aatttgtaga acaagttaaa gctttaaatc tttaagcggc    3000
cgctaccccg taggatccag gaggttagtt agaatggttc ttaaaaattg gcaggatctt    3060
tataaaagta aaattgttag tgcagacgaa gctgtatcta agtaagctg tggagatagc    3120 ataattttag gcaatgcttg tggagcatct cttacacttt tagatgcctt ggctgcaaat    3180
aaggaaaagt ataagagtgt aaagatacac aatcttatac ttaattataa aaatgatata    3240
tatactgatc cggaatcaga aaagtatatt catggaaata ctttctttgt aagtggaggt    3300
acaaaggaag cagttaattg taatagaaca gattatactc catgcttttt ttatgaaata    3360
ccaaaattat taaaacaaaa gtatataaat gcagatgtag ctttattca agtaagtaag    3420 cctgatagcc atggatactg tagctttgga gtatcaaccg attattcaca ggcaatggta    3480
cagtctgcaa agcttataat tgcagaagta acgatcaga tgccaagagt tttaggagac    3540
```

| | |
|---|---:|
| aattttatac acatttctga tatggattac atagtagaaa gttcacgtcc aattctagaa | 3600 |
| ttgactcctc ctaaaatagg agaagtagag aagacaatag gaaaatactg tgcatctctt | 3660 |
| gtagaagatg gttctacact tcagcttgga ataggagcta ttccagatgc agtactttta | 3720 |
| ttcttgaagg ataaaaagga tttgggtata cattcagaaa tgatatccga tggtgttgtt | 3780 |
| gaattagttg aagcaggggt aattacaaat aagaaaaagt cccttcatcc aggaaaaata | 3840 |
| attattacat tcttaatggg aactaagaaa ttatatgatt tcataaatga taatcctatg | 3900 |
| gtagaaggat accctgtaga ttatgtaaat gatcctaagg ttattatgca aaattctaag | 3960 |
| atggtatgta taaactcctg tgtagaagtg gatttcacag gacaagtgtg tgctgaaagt | 4020 |
| gtaggattta aacaaataag cggtgtaggt ggacaagttg attacatgag aggagctagc | 4080 |
| atggctgatg gaggaaaatc aattcttgct ataccatcta ctgcagctgg cggcaaaatt | 4140 |
| tcaagaatag ttcctatttt aactgaagga gcggggggtta ctacttcaag atatgatgtt | 4200 |
| caatatgttg ttacagaata tggtattgca cttctcaagg gcaaatccat aagagaaaga | 4260 |
| gctaaggagc ttataaaaat tgcacatcct aaatttaggg aagaattaac agctcaattt | 4320 |
| gaaaaaagat tcagttgtaa gctttaagcg ccacttaatg atttgccagt aaaagagatt | 4380 |
| gtttctagct ctcacattct tgcagatata atattgccta gagctgaagt tatatatgat | 4440 |
| tatcttaagt aataaaaata agagttacct taaatggtaa ctcttatttt tttaatgtcg | 4500 |
| actcatagaa tt | 4512 |

<210> SEQ ID NO 57
<211> LENGTH: 1519
<212> TYPE: DNA
<213> ORGANISM: Artificial Sequence
<220> FEATURE:
<223> OTHER INFORMATION: DNA fragment of cat3

<400> SEQUENCE: 57

| | |
|---|---:|
| ggcgcctacc ccgtaggatc caggaggtta gttagaatgg tttttaaaaa ttggcaggat | 60 |
| ctttataaaa gtaaaattgt tagtgcagac gaagctgtat ctaaagtaag ctgtggagat | 120 |
| agcataattt taggcaatgc ttgtggagca tctcttacac ttttagatgc cttggctgca | 180 |
| aataaggaaa agtataagag tgtaaagata cacaatctta tacttaatta taaaaatgat | 240 |
| atatatactg atccggaatc agaaaagtat attcatggaa atactttctt tgtaagtgga | 300 |
| ggtacaaagg aagcagttaa ttgtaataga acagattata ctccatgctt tttttatgaa | 360 |
| ataccaaaat tattaaaaca aaagtatata aatgcagatg tagcttttat tcaagtaagt | 420 |
| aagcctgata gccatggata ctgtagcttt ggagtatcaa ccgattattc acaggcaatg | 480 |
| gtacagtctg caaagcttat aattgcagaa gtaaacgatc agatgccaag agttttagga | 540 |
| gacaatttta tacacatttc tgatatggat tacatagtag aaagttcacg tccaattcta | 600 |
| gaattgactc ctcctaaaat aggagaagta gagaagacaa taggaaaata ctgtgcatct | 660 |
| cttgtagaag atggttctac acttcagctt ggaataggag ctattccaga tgcagtactt | 720 |
| ttattcttga aggataaaaa ggatttgggt atacattcag aaatgatatc cgatggtgtt | 780 |
| gttgaattag ttgaagcagg ggtaattaca aataagaaaa agtcccttca tccaggaaaa | 840 |
| ataattatta cattcttaat gggaactaag aaattatatg atttcataaa tgataatcct | 900 |
| atggtagaag gataccctgt agattatgta aatgatccta aggttattat gcaaaattct | 960 |
| aagatggtat gtataaactc ctgtgtagaa gtggatttca caggacaagt gtgtgctgaa | 1020 |
| agtgtaggat ttaaacaaat aagcggtgta ggtggacaag ttgattacat gagaggagct | 1080 |

```
agcatggctg atggaggaaa atcaattctt gctataccat ctactgcagc tggcggcaaa    1140
atttcaagaa tagttcctat tttaactgaa ggagcggggg ttactacttc aagatatgat    1200
gttcaatatg ttgttacaga atatggtatt gcacttctca agggcaaatc cataagagaa    1260
agagctaagg agcttataaa aattgcacat cctaaattta gggaagaatt aacagctcaa    1320
tttgaaaaaa gattcagttg taagctttaa gcgatcgcac ttaatgattt gccagtaaaa    1380
gagattgttt ctagctctca cattcttgca gatataatat tgcctagagc tgaagttata    1440
tatgattatc ttaagtaata aaaataagag ttaccttaaa tggtaactct tatttttta    1500 atgtcgactc atagaattc                                                 1519

<210> SEQ ID NO 58
<211> LENGTH: 1210
<212> TYPE: DNA
<213> ORGANISM: Artificial Sequence
<220> FEATURE:
<223> OTHER INFORMATION: Butanol dehydrogenase from E. coli codon
      optimized for C. ljungdahlii (YghD_E(coCl))

<400> SEQUENCE: 58
gcgatcgcta ccccgtagga tccaggaggt tagttagaat gaacaacttt aatctgcaca      60
ccccaaccag aattctgttt ggtaaaggcg caatcgctgg tttaagagaa caaattcctc     120
acgatgctag agtattgatt acctacggcg gcggcagcgt gaaaaaaacc ggcgttctcg     180
atcaagttct ggatgccctg aaaggcatgg acgtgctgga atttggcggt attgagccaa     240
acccggctta tgaaacgctg atgaacgccg tgaaactggt tagagaacag aaagtgactt     300
tcctgctggc ggttggcggc ggttctgtac tggacggcac caaatttatc gccgcagcgg     360
ctaactatcc ggaaaatatc gatccgtggc acattctgca aacgggcggt aaagagatta     420
aaagcgccat cccgatgggc tgtgtgctga cgctgccagc aaccggttca gaatccaacg     480
caggcgcggt gatctcccgt aaaaccacag gcgacaagca ggcgttccat tctgcccatg     540
ttcagccggt atttgccgtg ctcgatccgg tttataccta caccctgccg ccgcgtcagg     600
tggctaacgg cgtagtggac gccttttgtac acaccgtgga acagtatgtt accaaaccgg     660
ttgatgccaa aattcaggac cgtttcgcag aaggcatttt gctgacgcta atcgaagatg     720
gtccgaaagc cctgaaagag ccagaaaaact cgatgtgag agccaacgtc atgtgggcgg     780
cgactcaggc gctgaacggt ttgattggcg ctggcgtacc gcaggactgg caacgcata      840 tgctgggcca cgaactgact gcgatgcacg gtctggatca cgcgcaaaca ctggctatcg     900
tcctgcctgc actgtggaat gaaaaaagag ataccaagag agctaagctg ctgcaatatg     960
ctgaaagagt ctggaacatc actgaaggtt ccgatgatga gcgtattgac gccgcgattg    1020
ccgcaaccag aaatttcttt gagcaattag gcgtgccgac ccacctctcc gactacggtc    1080
tggacggcag ctccatcccg gctttgctga aaaaactgga agagcacggc atgacccaac    1140
tgggcgaaaa tcatgacatt acgttggatg tcagcagacg tatatacgaa gccgccagat    1200
aaggcgcgcc                                                          1210

<210> SEQ ID NO 59
<211> LENGTH: 3658
<212> TYPE: DNA
<213> ORGANISM: Artificial Sequence
<220> FEATURE:
<223> OTHER INFORMATION: pATh-LEM-17

<400> SEQUENCE: 59
```

-continued

```
ggcgcctacc ccgtaggatc caggaggtta gttagaatga actttgaact caccaaagaa      60
caacaaatga ttagagataa tgttcgaaag tttgcagaag caaaaatcga gcctattgca     120
tttcaactag atgagaaaaa tatatttcct gaagaaatag ttaatgagat ggggatcta     180
tctattatgg gtcttccata cccaaaagaa tatggtggag cgggaaaaga tgtattgagc     240
tatgctattg cggtagaaga actatcaagg gtagatgcag gtgtgggtgt tatattatct     300
gcacacacat ctcttggaac ttggcctatt atggagtttg gacaaaaga acaaaaagaa     360
aaatatctag ttccactggc ctcgggcaag aaaattgctg cttttggtct tacagaacct     420
aatgctggaa gtgatgccgg caagacagaa actacagcgg ttttagaagg cgatcattat     480
gtcataaatg ttctaaggt atttataaca aatgcggatt atgcagatac ttatgtaata     540
tttgcggtta caactccagg tttgggaacc aagggaataa gtgccttat tattgagaag     600
ggtatggatg gatttacttt tggtactcat tataataaaa tgggtatacg ttcttccgct     660
acagcagagc ttttatttaa aaatttgaag gtaccaaaat ataatctttt gggaaaagaa     720
aatgagggct ttaaaattgc catgcagacc ctagaaggtg ggcgcatagg tattgcggca     780
caggcacttg gaattgccca gggtgcatat gagaaagcac taagctactc caaggaaaga     840
gttcagtttg gaaaacctat ttcaagacaa caatccatag catttaaact tgcggatatg     900
gctactaaaa ttcgggcggc tagatttatg gtatatagtg cagctgtatt aaagcaggaa     960
cataaaaatt atggaatgga atccgctatg gcgaaattgt atgcttctga tatttgcctt    1020
gaagttgtta atgatgcagt gcaaatatat gggggctcag gatttattaa aggatttcct    1080
gtagagcgta tgtaccgtga tgctaagatc tgtacaatat atgaaggaac taatgagatt    1140
caaagactta ttatctccaa tgatatttta ggtaaaccta aaaaagaacc tattgaggaa    1200
aataaagaaa ataaagttaa taagcaaaa cctataacgg gaaaccgtag gagggtcatt    1260
ataaagaag gctctccaaa agaaaaggtg gatgcatttt taaattatat taaaagtgaa    1320
aatatagata ttaataaaag tgaagcttct aaaggaagta tagcagacgc agataaagta    1380
tgcagtatag gactgggatt aaaggataaa aaagacttgc ctttaataca atcactagcg    1440
gatacagttg gtgctgaact tggctgttcc agacctgtgg ctgaagaaag gaatggctg    1500
ccacttgatc gttatgtagg catatcgggt cagaaattcg gtggaacatt ttatcttgcc    1560
attggtatat caggacaagt tcaacattta aagggaattg aaaatgctgg aattataact    1620
gctataaaca tagatgagga tgctcctata tttaagagtt cagattatgg tattgtagga    1680
gatctatatg aaattgtgcc gctgcttatt gaggctttaa aatagtaccc cgtaggatcc    1740
aggaggttag ttagaatggg tggtaccgcg gcagacattt cgcccagcg aaataggtct    1800
gtcttttat ttgccatttg tttgagagaa aggaaagaag ctttaatgga tattatagtt    1860
ttagttaaac aagttccgga tatggaaaaa gtaaatttg acagagaaaa gggagtagta    1920
gatagaacat ctgccagtgc agaaatcaat ccttttgatt taaatgcact ggaaacagca    1980
gttcaaatag ctgaaaatat cgatgccaga gttactgctg taagtatggg gcctccaaat    2040
acagaaagtg cgttaaaaga atgtattgca aggggtgctc atgaaggagt gcttgtaagt    2100
gatagaaaat ttggaggttc agatacaaag gcgacttcta aatacttgc cagtgccatt    2160
aaaaagttgg gagcctatga tctggtaatc gctggagaaa agactgtaga tggagataca    2220
ggacaggtt gtcccgaagt tgcagaattt ttaaatatac ctcatgcaag ttatgtaagt    2280
aaaattacag aaatgaataa ggacagcatg gaggtacatt ctgaaatctg ggaaggaact    2340
```

```
tatttaaaaa gtataaaatt tccatgtctt attacagtta caaaggatat caatcatcca    2400
agattgcctt cttttaaaaa taagatgaaa gccagaaaag cagagattaa gatattaaag    2460
cttgaggatt tagaagaatt tttgaatgag gataatgttg gctttaaggg ttcacctaca    2520
aaagtaaaga aaatagaaat tccccaaata gaaaaaagac agggaaaaat ttatagggag    2580
tcagatactg ttgaggcaga gaatgaatta attaatatat ttaaaaagat taaggttttg    2640
gaggtgtagt agtgggtaag gaatatagtg gtatattggt atttgcagaa caaaaaaatg    2700
gacaaattca taaagtcagt tatgaacttc tgggaaaagc aaggcagctt tctgataaat    2760
taaatgctcc ggtgtacagt gttgtgttag gagcagatgg tatagaggcc gaagaactta    2820
tatatagggg agcagataag gtattttata tacaggatga tatgtttaat ctaccagaag    2880
aagtaaccta taaattaac ctgaagaatt taattaaaga tatcaaacct gaaattttt    2940 tgattggtgc cactaccctg gaagatcat tggcacctag gctggcagcg tccttaaata    3000
cgggacttac agcagattgt acaggtcttg aaatcgatga agatagaaaa ttggttcaga    3060
taagaccggc ttttagcgaa aatatactgg ctcatataaa aacatacaca tatccccaga    3120
tggctacagt gagatataaa gaatttgacg agggcacaag agatgctaaa aggcagggag    3180
atattttaaa ggtagaggct ttaagactcg aaaatgaact ggtaaagtg ataacacaac    3240 ttagatccca ggaaattaat atatctgatg caaatgtagt agtggcagcg ggtaaaggat    3300
tgaaaaaggc agaagatatg gctatgttaa aggagttagc ggatttgctg ggaggtgtag    3360
ttggagccag cagggaaata gttgaagaag ggtttatatc caaggacttt caagtaggat    3420
acagcggcaa cagggtaaaa cctaaattat atatagcttg tggaatttca ggagcaccgc    3480
agcaccttgc aggaatgaaa gaatcggggt ttattgttgc aatcaataca gatccttcag    3540
ctcctatatt taatatagca gactacgaaa tagttgatga tatgtataag gtaatacctg    3600
atttgataac taagataaaa gaaagcagtt tagaaactat aaattgttaa gcggccgc      3658

<210> SEQ ID NO 60
<211> LENGTH: 9316
<212> TYPE: DNA
<213> ORGANISM: Artificial Sequence
<220> FEATURE:
<223> OTHER INFORMATION: vector pATh-LEM-22

<400> SEQUENCE: 60
ctcgagcgtc gatccgattc acaaaaaata ggtacacgaa aaacaagtta agggatgcag      60
tttatgcatc ccttaactta cttattaaat aatttatagc tattgaaaag agataagaat     120
tgttcaaagc taatattgtt taaatcgtca attcctgcat gttttaagga attgttaaat     180 tgatttttg taaatatttt cttgtattct ttgttaaccc atttcataac gaaataatta     240
tacttctgtt tatctttgtg tgatattctt gatttttttc tatttaatct gataagtgag     300
ctattcactt taggtttagg atgaaaatat tctcttggaa ccatacttaa tatagaaata     360
tcaacttctg ccattaaaaa taatgccaat gagcgttttg tatttaataa tcttttagca     420
aacccgtatt ccacgattaa ataaatctca tcagctatac tatcaaaaac aatttttgcgt     480 attatatccg tacttatgtt ataaggtata ttaccaaata ttttataggga ttggttttta     540 ggaaatttaa actgcaatat atccttgttt aaaacttgga aattatcgtg atcaacaagt     600 ttatttctg tagttttgca taatttatgg tctatttcaa tggcagttac gaaattacac     660
ctctgtacta attcaagggt aaaatgccct tttcctgagc cgatttcaaa gatattatca     720
tgttcattta atcttatatt tgtcattatt ttatctatat tatgtttga agtaataaag     780
```

```
ttttgactgt gttttatatt tttctcgttc attataaccc tctttatttt ttcctcctta      840
taaaattagt ataattatag cacgagctct gataaatatg aacatgatga gtgatcgtta      900
aatttatact gcaatctgat gcgattattg aataaaagat atgagagatt tatctagttt      960
ctttttttac aagaaaaaag aaagttctta aaggttttat acttttggtc gtagagcaca     1020
cggtttaacg acttaattac gaagtaaata agtctagtgt gttagacttt aatgtttttt     1080
taaggcatta gtgcatttaa gcgtcagagc atggctttat gccgagaaaa ctattggttg     1140
gaatggcgtg tgtgttagcc aaagctcctg caggtcgact ttttaacaaa atatattgat     1200
aaaaataata atagtgggta taattaagtt gttagagaaa acgtataaat tagggataaa     1260
ctatggaact tatgaaatag attgaaatgg tttatctgtt accccgtagg atccaggagg     1320
ttagttagaa tggaatttaa aaatatcatt cttgaaaagg atggaaatgt ggcttcaata     1380
acgttgaata gacctaaggc attaaatgca ttaaatgcag caactttaaa agagatagat     1440
gccgcaataa acgacattgc tgaagatgat aacgtatatg ctgtgataat tactgggtca     1500
ggtaaagctt ttgtagcagg agcagatata gctgagatga agatcttac tgcagttgag      1560 ggaagaaagt tttcagttct tggcaataaa atatttagaa aattagaaaa tttagaaaaa     1620
ccagttatag cagctataaa tggatttgca ctgggtggtg gctgtgaatt gtcattgtct     1680
tgcgatataa gaatagcttc atcaaaggct aagtttggtc aaccagaggt tggtcttgga     1740
attactccag ggtttggagg tactcaaaga cttgcaagag caataggcgt tggtatggct     1800
aaggaactta tataccgg aaaagtaatt aatgctgaag aggcattaag aataggtttg      1860
gtaaataaag tagttgagcc agataaatta ttggaagaag ctaaagcttt agtagatgct     1920
attattgtta atgcacctat agctgttaga atgtgtaagg ctgctataaa tcaaggactt     1980
cagtgtgata tagatacagg tgtagcttat gaagcagaag tatttgggga atgttttgct     2040
acagaagata gagtagaagg aatgacagca tttgtagaaa aaagagacaa ggcttttaaa     2100
aataagtaag gccggccaaa gtattgttaa aaagggaggt ctgtttaatg agtattaaaa     2160
gtgtagcggt tttaggtagt ggaactatgt ctcgtggaat tgtgcaggct tttgcagaag     2220
caggtataga tgtaattatc cgtggaagaa ctgaaggtag tattggaaaa ggtctagcag     2280
cagtaaagaa agcttatgat aaaaaagtat caaaggggaa aatttcccag gaagatgctg     2340
ataaaatagt tggaagagta agtacaacaa ctgaacttga aaaattggct gattgtgatc     2400
ttataataga agcagcatca gaggatatga atataaagaa agactatttt ggaaaattag     2460
aagaaatatg caagcctgaa acaattttg ctactaaatc ttcttcatta tctataactg      2520
aagtagcaac agctacaaag agaccagata aattcatagg aatgcatttc tttaatccag     2580
caaatgttat gaaattagtt gaaatcataa gaggtatgaa tacttcacaa gaaacttttg     2640
atattataaa agaagcttcc attaaaatag gaaaaactcc tgtagaagtt gcagaagctc     2700
caggatttgt tgtaaacaag atattagtac caatgatcaa tgaagcagta ggaatttgg      2760 cagaaggaat agcttcagca gaagatatcg atacagctat gaaattaggc gctaatcacc     2820
caatgggtcc tttagcatta ggagatctta ttggacttga tgtagttctt gcagttatgg     2880
atgtacttta tagtgaaact ggagattcaa aatatagagc tcatacatta cttagaaaat     2940
atgtaagagc aggatggctt ggaagaaaat caggaaaagg attcttcgct tattaattaa     3000
ttaagtttac aagaatggcg ctttaggagg attagtcatg aaagaagttg taatagctag     3060
tgcagtaaga acagcgattg gatcttatgg aaagtctctt aaggatgtac cagcagtaga     3120
```

```
tttaggagct acagctataa aggaagcagt taaaaaagca ggaataaaac cagaggatgt    3180
taatgaagtc attttaggaa atgttcttca agcaggttta ggacagaatc cagcaagaca    3240
ggcatctttt aaagcaggat taccagttga aattccagct atgactatta ataaggtttg    3300
tggttcagga cttagaacag ttagcttagc agcacaaatt ataaaagcag agatgctga     3360
cgtaataata gcaggtggta tggaaaatat gtctagagct ccttacttag cgaataacgc    3420
tagatgggga tatagaatgg gaaacgctaa atttgttgat gaaatgatca ctgacggatt    3480
gtgggatgca tttaatgatt accacatggg aataacagca gaaaacatag ctgagagatg    3540
gaacatttca agagaagaac aagatgagtt tgctcttgca tcacaaaaaa agctgaaga     3600
agctataaaa tcaggtcaat ttaaagatga aatagttcct gtagtaatta aaggcagaaa    3660
gggagaaact gtagttgata cagatgagca ccctagattt ggatcaacta tagaaggact    3720
tgcaaaatta aaacctgcct tcaaaaaaga tggaacagtt acagctggta atgcatcagg    3780
attaaatgac tgtgcagcag tacttgtaat catgagtgca gaaaaagcta agagcttgg     3840
agtaaaacca cttgctaaga tagttttctta tggttcagca ggagttgacc cagcaataat    3900
gggatatgga cctttctatg caacaaaagc agctattgaa aaagcaggtt ggacagttga    3960
tgaattagat ttaatagaat caaatgaagc ttttgcagct caaagtttag cagtagcaaa    4020
agatttaaaa tttgatatga ataaagtaaa tgtaaatgga ggagctattg cccttggtta    4080
tccaattgga gcatcaggtg caagaatact cgttactctt gtacacgcaa tgcaaaaaag    4140
agatgcaaaa aaaggcttag caactttatg tataggtggc ggacaaggaa cagcaatatt    4200
gctagaaaag tgctaggagg taagtttatg gcgccactta atgatttgcc agtaaaagag    4260
attgtttcta gctctcacat tcttgcagat ataatattgc ctagagctga agttatatat    4320
gattatctta agtaataaaa ataagagtta ccttaaatgg taactcttat ttttttaatg    4380
tcgactcata ggcgcgcctt aaagcttaca actgaatctt ttttcaaatt gagctgttaa    4440
ttcttcccta aatttaggat gtgcaatttt tataagctcc ttagctcttt ctcttatgga    4500
tttgccttg agaagtgcaa taccatattc tgtaacaaca tattgaacat catatcttga    4560
agtagtaacc cccgctccct tcagttaaaat aggaactatt cttgaaattt tgccgccagc    4620
tgcagtagat ggtatagcaa gaattgattt tcctccatca gccatgctag ctcctctcat    4680
gtaatcaact tgtccaccta caccgcttat ttgttttaaat cctacacttt cagcacacac    4740
ttgtcctgtg aaatccactt ctacacagga gtttatacat accatcttag aattttgcat    4800
aataaccta ggatcatttta cataatctac agggtatcct tctaccatag gattatcatt    4860
tatgaaatca tataatttct tagttcccat taagaatgta ataattattt ttcctggatg    4920
aagggacttt tcttatttg taattacccc tgcttcaact aattcaacaa caccatcgga    4980
tatcatttct gaatgtatac ccaaatcctt tttatccttc aagaataaaa gtactgcatc    5040
tggaatagct cctattccaa gctgaagtgt agaaccatct tctacaagag atgcacagta    5100
ttttcctatt gtcttctcta cttctcctat tttaggagga gtcaattcta gaattggacg    5160
tgaactttct actatgtaat ccatatcaga aatgtgtata aaattgtctc ctaaaactct    5220
tggcatctga tcgtttactt ctgcaattat aagctttgca gactgtacca ttgcctgtga    5280
ataatcggtt gatactccaa agctacagta tccatggcta tcaggcttac ttacttgaat    5340
aaaagctaca tctgcattta tactttttg ttttaataat tttggtattt cataaaaaaa    5400
gcatggagta taatctgttc tattacaatt aactgcttcc tttgtacctc cacttacaaa    5460
gaaagtattt ccatgaatat acttttctga ttccggatca gtatatatat catttttata    5520
```

```
attaagtata agattgtgta tctttacact cttatacttt tccttatttg cagccaaggc    5580
atctaaaagt gtaagagatg ctccacaagc attgcctaaa attatgctat ctccacagct    5640
tactttagat acagcttcgt ctgcactaac aattttactt ttataaagat cctgccaatt    5700
tttaaaaacc attctaacta acctcctgga tcctacgggg tagcggccgc ttaaagattt    5760
aaagctttaa cttgttctac aaattctgga acaaccttat ataaatctcc tacaattgca    5820
agatccgcta cttgcatcat tggagcgttt tcatctttat tgatagctac gataaatcca    5880
ctatcctgca taccagctaa atgttgtatt tgacctgata ttccgcatgc aatataaaga    5940
cctggtctta ctgttttacc agtttgtcca acctgatagc tcttatctat ccagccagca    6000
tctatagttg cacgggatcc acctatagtt ccacctaata aatctgctaa ttctttaaga    6060
actttgaatc catctggacc accaagtcct cttccacctg atacaattac atctgcttct    6120
gaaatatcta ttgtatcgcc agcagattta actacttcaa gcacttcaat tctgatgtca    6180
tcttttgcaa catttgcagc tatttttcct atttttccag ttcttgaagc atctcttgga    6240
agcgcattaa aaactcctgg tcttactgtt gacatttgag gtcttgtttt ttcgcaagct    6300
atagttgcca ttaagtttcc accaaatgca ggtcttgtca tcatcaaatt ttttgttgcc    6360
tcatctatat caagtcctgt acagtctgct gtaagacctg taaaaactct acctgcaact    6420
cttggtccta agtctcttcc gataaatgta gctcctataa gtaatatttc tggttttctt    6480
tcttttataa gttcatctat tactttagtg tatccatctg tagtataatg ttttaaaaga    6540
ggactatctg cgtataaaac attgtctgct ccatatgcaa ctaattcttt tgccaaatca    6600
tctacttcac taccaagtaa tacagcagtt aattctactc ctaaagtgtc tgccaattct    6660
cttccttttc caactaattg aagtgctact ttttgtagtt ctccatccct tgttcagca    6720 aatacccata cgcctttgta ttctgctaag ttcattctaa acccctccta tatattaaat    6780
gacatgtttt tctcttaatt ttgaaattga atatgctact gcttctttta ttggtttatt    6840
aacgatttct cctgctcctt ttgcttcttt tgtatgtgat ctcttaactt ttgtgcagga    6900
accattaaga ccaagtttat ttttatctac atctaagtcg tcagcactcc atattttaac    6960
ttctttcttg aaaacttcaa atatgttctt catgttcata tatcttggtt gatttaactc    7020
ttttatagca gttaacatgc atggagtttt aatttttgct acttcatatc catcttccca    7080
agctctttga actgttaaag tatctccatc tacatcaact ttttctacat atgttatctg    7140
aggtattcct aatttttctg ctatttgagg tccaacctgt gcagtatctc catctatagc    7200
ttgtcttcct gcaaatatta aatcatattc taaattttta agtgctcctg ctaatgcata    7260
ggaagtagct tgagtatctg ctcctgcaaa agctctgtct gaaactaata ttgcttcatc    7320
agctcccata gctagagctt ctctaagtgc atccactgcc tgtggaggcc ccatgcttac    7380
tactgtaact gtacccccta ctttttcttt taaagcaatt gattcttcaa gtgcattttt    7440
atcatctggg tttattattg atggaacgcc ttctcttatt aatgttcctg tttttggatc    7500
tattttaact tcagttgtat ctggtacttg ctttaagcaa actactattt tcattatgaa    7560
ctcctcctat ttatttaaat aaatttgctg aaataaccat cttttgtact tgtgaagttc    7620
cttcatatat ttcagttatc ttagcatctc tcatcattct ttctactgga taatccttag    7680
tgaatccata tccaccaaag atttgaacaa ctttagtagt tgtttccata gctacagtag    7740
ccgcagctaa tttagctctt gcagcttcca ctgaatatgg aagacccatt tgtttattta    7800
ctgctgcttt ataaacaagt tgtttaacag cttctatttt agtatctaat tctgcaacca    7860
```

```
tccatgctaa tccctggaat ttgtaaagag cttttccaaa ttgttttctt tctttcatat    7920
aattaagtgc ttcagctaat gcgccttctg ctaaacctaa cgcttgtgct gctataccaa    7980
ttcttcctcc atcaagagta tgcattgcta cagtaaatcc ttttccttct tttcctaaca    8040
tattttcttt tggaactatg caattctcaa atataagttc tgtagttgag gaagctctaa    8100
ttcccaactt atcttcagat tttcctatgg agaaaccagg gaaatctttt tcaactataa    8160
atgctgttat tcctcttgta cccttgcttc tgtctgtcat tgcaaatatt acaaaagtat    8220
ctgcatatgc accatttgta ataaatattt tttgtccatt taatacataa tgatcccctt    8280
ctaaaacagc tgttgtctgc tgtccagcag catcagtacc tgcattaggt tcagttaaac    8340
caaatgctcc aagtttttct cccttgcaa gaggaactaa gtattttgt ttctgttctt    8400 ctgtacccca atcataaata ggtgctgcac aaagtgaagt atgtgctgac aatatagttg    8460
atgatgaagt acaactcttt gcaagtcctt ctactgctat tatataggat aaataatctg    8520
tacctgagcc gccgtattca actggaaaag gcatacccat cattccgtat ttagcaaatt    8580
tttctactgt ctcaagagga aacctttctg tttcatctat ttcagcagct ataggtttaa    8640
cttcattttc agtaaattca cttaccattt gttctacaaa tttttgctcg tttgttaatg    8700
taaaatccat tctaactaac ctcctggatc ctacggggta gcgatcgctt taaatttaac    8760
acaaaattac acacacttat actataatcc tttttagttg tattttcaa taaaaatcat    8820 tcaaaaatat aactttgat aagaaattc acaaattaaa gtatcaaaaa attttgctag    8880
tcaatacttt actcaatatt atataatgta aatcaaataa gcaaaatt aatctgaaaa    8940 tagatactct atttaaaaat cctacactaa tacttatttt attgttataa tatgtatata    9000
tttcacttag gcattttaaa ataaataatc aatcaatata ctagcctatt ttttcaaatg    9060
ccctatactt tgtacttata gttctttaat gaaataaaca gagttcttga catggaataa    9120
aatattttag aaaggaaaat ttctatgaac gtaactggaa taatagttga atataatccc    9180
tttcacaatg gacataaata tcatattgaa agtgctcgtt ctgctacaaa atgtgatgct    9240
gtaatagcag ttatgagtgg taacttcgtg caaagaggtt caccatctat agttgacaaa    9300
tgcctgcagg gaattc                                                     9316
```

GENETICALLY MODIFIED ACETOGENIC CELL

CROSS REFERENCE TO RELATED APPLICATIONS

The present application is US national stage of international application PCT/EP2016/081202, which had an international filing date of Dec. 15, 2016, and which was published in English on Jun. 22, 2017. Priority is claimed to European application 15200673.0, filed on Dec. 17, 2015. The contents of these prior applications is hereby incorporated by reference in their entirety.

FIELD OF THE INVENTION

The present invention relates to a recombinant cell for the production of a higher alcohol from a carbon source. In particular, the cell is an acetogenic microorganism. The present invention also relates to a method of producing at least one higher alcohol from a carbon source in the presence of the recombinant acetogenic cell.

BACKGROUND OF THE INVENTION

Butanol and higher alcohols have several uses including being used as fuel. For example, butanol in the future can replace gasoline as the energy contents of the two fuels are nearly the same. Further, butanol has several other superior properties as an alternative fuel when compared to ethanol. These include butanol having higher energy content, butanol being less "evaporative" than ethanol or gasoline and butanol being easily transportable compared to ethanol. For these reasons and more, there is already an existing potential market for butanol and/or related higher alcohols. Butanol and other higher alcohols are also used as industrial solvents. Higher alcohols are also used in the perfume and cosmetic industry. For example, hexanol is commonly used in the perfume industry.

Currently, butanol and other higher alcohols are primarily manufactured from petroleum. These compounds are obtained by cracking gasoline or petroleum which is bad for the environment. Also, since the costs for these starting materials will be linked to the price of petroleum, with the expected increase in petroleum prices in the future, butanol and other higher alcohol prices may also increase relative to the increase in the petroleum prices.

Historically (1900s-1950s), biobutanol was manufactured from corn and molasses in a fermentation process that also produced acetone and ethanol and was known as an ABE (acetone, butanol, ethanol) fermentation typically with certain butanol-producing bacteria such as *Clostridium acetobutylicum* and *Clostridium beijerinckii*. This method has recently gained popularity again with renewed interest in green energy. However, the "cornstarch butanol production" process requires a number of energy-consuming steps including agricultural corn-crop cultivation, corn-grain harvesting, corn-grain starch processing, and starch-to-sugar-to-butanol fermentation. The "cornstarch butanol production" process could also probably cost nearly as much energy as the energy value of its product butanol.

The Alfol® Alcohol Process is a method used to producing higher alcohols from ethylene using an organoaluminium catalyst. The reaction produces linear long chain primary alcohols ($C_2$-$C_{28}$). The process uses an aluminum catalyst to oligomerize ethylene and allow the resulting alkyl group to be oxygenated. However, this method yields a wide spectrum of alcohols and the distribution pattern is maintained. This constant pattern limits the ability of the producer to make only the specific alcohol range that is in highest demand or has the best economic value. Also, the gases needed in the reaction have to be very clean and a distinct composition of the gases is needed for the reaction to be successfully carried out.

WO2009100434 also describes an indirect method of producing butanol and hexanol from a carbohydrate. The method includes a homoacetogenic fermentation to produce an acetic acid intermediate which is then chemically converted to ethanol. The ethanol and a remaining portion of the acetic acid intermediate are then used as a substrate in an acidogenic fermentation to produce butyric and caproic acid intermediates which are then chemically converted to butanol and hexanol. However, this method uses expensive raw material carbohydrates and has two additional process steps, the formation of the esters and the chemical hydrogenation of the esters which make the method not only longer but also results in loss of useful material along the way.

Perez, J. M., 2012 discloses a method of converting short-chain carboxylic acids into their corresponding alcohols in the presence of syngas with the use of *Clostridium ljungdahlii*. However, short-chain carboxylic acids have to be added as a substrate for the conversion to the corresponding higher alcohol.

The currently available methods of higher alcohol production thus has limitations in mass transfer of the gaseous substrates into fermentation broth, lower productivity, and lower concentrations of end products, resulting in higher energy costs for product purification.

Accordingly, it is desirable to find more sustainable raw materials, other than purely petroleum based or corn based sources, as starting materials for butanol and other higher alcohol production via biotechnological means which also cause less damage to the environment. In particular, there is a need for a simple and efficient one-pot biotechnological production of butanol and other higher alcohols from sustainable raw material.

DESCRIPTION OF THE INVENTION

The present invention provides a cell that has been genetically modified to produce at least one higher alcohol from a simple carbon source. In particular, the cell may be capable of converting CO and/or $CO_2$ to at least one higher alcohol. Namely, the cell may be genetically modified to express a butyryl-CoA:acetate CoA transferase (cat3) ($E_8$) at an expression level higher relative to the wild type cell. This is advantageous as a single cell may be used to produce a higher alcohol from non-petroleum based sources. Also, using the recombinant cell make the method of producing higher alcohols more efficient.

According to one aspect of the present invention, there is provided an acetogenic microbial cell which is capable of producing at least one higher alcohol from a carbon source, wherein the acetogenic microbial cell is genetically modified to comprise an increased expression relative to its wild type cell of at least one enzyme, $E_8$, butyryl-CoA:acetate CoA transferase (cat3).

The phrase "wild type" as used herein in conjunction with a cell or microorganism may denote a cell with a genome make-up that is in a form as seen naturally in the wild. The term may be applicable for both the whole cell and for individual genes. The term 'wild type' may thus also include cells which have been genetically modified in other aspects (i.e. with regard to one or more genes) but not in relation to the genes of interest. The term "wild type" therefore does not include such cells or such genes where the gene sequences have been altered at least partially by man using recombinant methods. A wild type cell according to any aspect of the present invention may thus refer to a cell that has no genetic mutation with respect to the whole genome and/or a particular gene. Therefore, in one example, a wild type cell with respect to enzyme $E_8$ may refer to a cell that has the natural/non-altered expression of the enzyme $E_8$ in the cell. The wild type cell with respect to enzyme $E_2$, $E_3$, $E_4$, $E_5$, $E_6$, $E_7$, $E_9$, $E_{10}$, $E_{11}$, $E_{12}$, etc. may be interpreted the same way and may refer to a cell that has the natural/non-altered expression of the enzyme $E_2$, $E_3$, $E_4$, $E_5$, $E_6$, $E_7$, $E_9$, $E_{10}$, $E_{11}$, $E_{12}$, etc. respectively in the cell.

A skilled person would be able to use any method known in the art to genetically modify a cell or microorganism. According to any aspect of the present invention, the genetically modified cell may be genetically modified so that in a defined time interval, within 2 hours, in particular within 8 hours or 24 hours, it forms at least twice, especially at least 10 times, at least 100 times, at least 1000 times or at least 10000 times more higher alcohol than the wild-type cell. The increase in product formation can be determined for example by cultivating the cell according to any aspect of the present invention and the wild-type cell each separately under the same conditions (same cell density, same nutrient medium, same culture conditions) for a specified time interval in a suitable nutrient medium and then determining the amount of target product (higher alcohol e.g. butanol) in the nutrient medium.

The genetically modified cell or microorganism may be genetically different from the wild type cell or microorganism. The genetic difference between the genetically modified microorganism according to any aspect of the present invention and the wild type microorganism may be in the presence of a complete gene, amino acid, nucleotide etc. in the genetically modified microorganism that may be absent in the wild type microorganism. In one example, the genetically modified microorganism according to any aspect of the present invention may comprise enzymes that enable the microorganism to produce higher alcohols. The wild type microorganism relative to the genetically modified microorganism of the present invention may have none or no detectable activity of the enzymes that enable the genetically modified microorganism to produce the at least one higher alcohol. As used herein, the term 'genetically modified microorganism' may be used interchangeably with the term 'genetically modified cell'. The genetic modification according to any aspect of the present invention is carried out on the cell of the microorganism.

The cells according to any aspect of the present invention are genetically transformed according to any method known in the art. In particular, the cells may be produced according to the method disclosed in WO/2009/077461.

The phrase 'the genetically modified cell has an increased activity, in comparison with its wild type, in enzymes' as used herein refers to the activity of the respective enzyme that is increased by a factor of at least 2, in particular of at least 10, more in particular of at least 100, yet more in particular of at least 1000 and even more in particular of at least 10000.

The phrase "increased activity of an enzyme", as used herein is to be understood as increased intracellular activity. Basically, an increase in enzymatic activity can be achieved by increasing the copy number of the gene sequence or gene sequences that code for the enzyme, using a strong promoter or employing a gene or allele that codes for a corresponding enzyme with increased activity and optionally by combining these measures. Genetically modified cells used in the method according to the invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extrachromosomally replicating vector. For example, a cell with an increase in expression of an enzyme such as enzyme $E_8$ relative to a wild type cell, may refer to a cell that may comprise:

an expression of a heterologous enzyme $E_8$,
an increase in the copy number of the gene expressing enzyme $E_8$,
an expression of enzyme $E_8$ with a heterologous promoter, or
combinations thereof.

A skilled person may be capable of measuring the activity of each of these enzymes using methods known in the art. The expression of the enzymes or genes according to any aspect of the present invention may be detected in a gel with the aid of 1- and 2-dimensional protein gel separation and subsequent visual identification of the protein concentration using suitable evaluation software. When the increase in an enzymatic activity is based exclusively on an increase in the expression of the gene in question, the quantification of the increase in the enzymatic activity can be determined in a simple manner by comparing the 1- or 2-dimensional protein separations between the wild type and the genetically modified cell. A conventional method of preparing the protein gels in coryneform bacteria, and of identifying the proteins, is the procedure described by Hermann et al. (*Electrophoresis*, 22: 1712.23 (2001)). The protein concentration can also be analysed by Western blot hybridization using an antibody which is specific for the protein to be detected (Sambrook et al., *Molecular Cloning: a laboratory manual*, $2^{nd}$ Ed. Cold Spring Harbor Laboratory Press, Cold Spring Harbor, N.Y. USA, 1989) followed by visual evaluation with suitable software for determining the concentration (Lohaus and Meyer (1989) *Biospektrum*, 5: 32-39; Lottspeich (1999), *Angewandte Chemie* 111: 2630-2647). The activity of DNA-binding proteins can be measured by means of DNA band shift assays (also referred to as gel retardation) (Wilson et al. (2001) *Journal of Bacteriology*, 183: 2151-2155). The effect of DNA-binding proteins on the expression of other genes can be detected by various, extensively described methods of the reporter gene assay (Sambrook et al., *Molecular Cloning: a laboratory manual*, $2^{nd}$ Ed. Cold Spring Harbor Laboratory Press, Cold Spring Harbor, N.Y. USA, 1989). The intracellular enzymatic activities can be detected by various methods which have been described (Donahue et al. (2000) *Journal of Bacteriology* 182 (19): 5624-5627; Ray et al. (2000) *Journal of Bacteriology* 182 (8): 2277-2284; Freedberg et al. (1973) *Journal of Bacteriology* 115 (3): 816-823). In the event that no specific methods for determining the activity of a particular enzyme are detailed in what follows, the determination of the increase in the enzymatic activity, and also the determination of the reduction in an enzymatic activity, may be carried out by means of the methods described in Hermann et al., Electrophoresis, 22: 1712-23 (2001), Lohaus et al., Biospektrum 5 32-39 (1998), Lottspeich, *Angewandte Chemie* 111: 2630-2647 (1999) and Wilson et al. *Journal of Bacteriology*, 183: 2151-2155 (2001).

The term "acetogenic bacteria" as used herein refers to a microorganism which is able to perform the Wood-Ljungdahl pathway and thus is able to convert CO, $CO_2$ and/or hydrogen to acetate. These microorganisms include microorganisms which in their wild-type form do not have a Wood-Ljungdahl pathway, but have acquired this trait as a result of genetic modification. Such microorganisms include but are not limited to *E. coli* cells. These microorganisms may be also known as carboxydotrophic bacteria. Currently, 21 different genera of the acetogenic bacteria are known in the art (Drake et al., 2006), and these may also include some clostridia (Drake & Kusel, 2005). These bacteria are able to use carbon dioxide or carbon monoxide as a carbon source with hydrogen as an energy source (Wood, 1991). Further, alcohols, aldehydes, carboxylic acids as well as numerous hexoses may also be used as a carbon source (Drake et al., 2004). The reductive pathway that leads to the formation of acetate is referred to as acetyl-CoA or Wood-Ljungdahl pathway.

In particular, the acetogenic bacteria may be selected from the group consisting of *Acetoanaerobium notera* (ATCC 35199), *Acetonema longum* (DSM 6540), *Acetobacterium carbinolicum* (DSM 2925), *Acetobacterium malicum* (DSM 4132), *Acetobacterium* species no. 446 (Morinaga et al., 1990, *J. Biotechnol., Vol.* 14, p. 187-194), *Acetobacterium wieringae* (DSM 1911), *Acetobacterium woodii* (DSM 1030), *Alkalibaculum bacchi* (DSM 22112), *Archaeoglobus fulgidus* (DSM 4304), *Blautia producta* (DSM 2950, formerly *Ruminococcus productus*, formerly *Peptostreptococcus productus*), *Butyribacterium methylotrophicum* (DSM 3468), *Clostridium aceticum* (DSM 1496), *Clostridium autoethanogenum* (DSM 10061, DSM 19630 and DSM 23693), *Clostridium carboxidivorans* (DSM 15243), *Clostridium coskatii* (ATCC no. PTA-10522), *Clostridium drakei* (ATCC BA-623), *Clostridium formicoaceticum* (DSM 92), *Clostridium glycolicum* (DSM 1288), *Clostridium ljungdahlii* (DSM 13528), *Clostridium ljungdahlii* C-01 (ATCC 55988), *Clostridium ljungdahlii* ERI-2 (ATCC 55380), *Clostridium ljungdahlii* O-52 (ATCC 55989), *Clostridium mayombei* (DSM 6539), *Clostridium methoxybenzovorans* (DSM 12182), *Clostridium neopropionicum* sp, *Clostridium ragsdalei* (DSM 15248), *Clostridium scatologenes* (DSM 757), *Clostridium* species ATCC 29797 (Schmidt et al., 1986, *Chem. Eng. Commun., Vol.* 45, p. 61-73), *Desulfotomaculum kuznetsovii* (DSM 6115), *Desulfotomaculum thermobezoicum* subsp. *thermosyntrophicum* (DSM 14055), *Eubacterium limosum* (DSM 20543), *Methanosarcina acetivorans* C2A (DSM 2834), *Moorella* sp. HUC22-1 (Sakai et al., 2004, *Biotechnol. Let., Vol.* 29, p. 1607-1612), *Moorella thermoacetica* (DSM 521, formerly *Clostridium thermoaceticum*), *Moorella thermoautotrophica* (DSM 1974), *Oxobacter pfennigii* (DSM 322), *Sporomusa aerivorans* (DSM 13326), *Sporomusa ovata* (DSM 2662), *Sporomusa silvacetica* (DSM 10669), *Sporomusa sphaeroides* (DSM 2875), *Sporomusa termitida* (DSM 4440) and *Thermoanaerobacter kivui* (DSM 2030, formerly *Acetogenium kivui*).

In particular, the acetogenic microbial cell used according to any aspect of the present invention may be selected from the group consisting of *Clostridium ljungdahlii* and *Clostridium autothenogenum*. In one example, suitable bacterium may be *Clostridium ljungdahlii*. In particular, strains selected from the group consisting of *Clostridium ljungdahlii* PETC, *Clostridium ljungdahlii* ERI2, *Clostridium ljungdahlii* COL and *Clostridium ljungdahlii* 0-52 may be used in the conversion of synthesis gas to hexanoic acid. These strains for example are described in WO 98/00558, WO 00/68407, ATCC 49587, ATCC 55988 and ATCC 55989. In another example, the acetogenic bacteria selected bacteria may be *Clostridium autothenogenum*.

The enzyme, $E_8$, a butyryl-CoA:acetate CoA transferase (cat3), the expression of which is increased in the cell according to any aspect of the present invention, relative to a wild type cell, catalyses the following reaction amongst others:

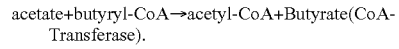

This enzyme is especially advantageous in the acetogenic cell according to any aspect of the present invention as it has a broad substrate specificity (Stadtman E R (1953). J Biol Chem 203:501-512 and Stadtman E R (1953) Fed Proc 12:692-693) and is capable of catalysing the conversion of acyl CoA to form at least one fatty acid (Seedorf et al., (2007) PNAS. 105 (6):2128-2133). The production of at least one acid from a carbon source comprising CO and/or $CO_2$ may be possible in the presence of the acetogenic cell according to any aspect of the present invention due to the presence of enzyme, $E_8$. The acid may be produced from the carbon source via acetate production where acetate may be used as the CoA acceptor. This may thus allow the cell according to any aspect of the present invention more efficient and effective in the production of a fatty acid.

In most acetogenic cells, butyrate may not be naturally produced. The production of butyrate may be introduced into an acetogenic cell by genetically modifying a cell to be capable of producing butyric acid from at least one carbon source comprising CO and/or $CO_2$. In one example, acetogenic cells already capable of producing butyrate may be used in the aspects of the present invention to introduce enzyme $E_8$ to enable the cell to produce at least one fatty acid from a carbon source comprising CO and/or $CO_2$. For example, *C. carboxidivorans* may be a cell like this.

In one example, the cell according to any aspect of the present invention may be genetically modified to comprise an increased expression relative to its wild type cell of at least one further enzyme selected from the group consisting of $E_1$ to $E_7$ and $E_9$ to $E_{11}$, wherein $E_1$ is an alcohol dehydrogenase (adh), $E_2$ is an acetaldehyde dehydrogenase (ald), $E_3$ is an acetoacetyl-CoA thiolase (thl), $E_4$ is a 3-hydroxybutyryl-CoA dehydrogenase (hbd), $E_5$ is a 3-hydroxybutyryl-CoA dehydratase (crt), $E_6$ is a butyryl-CoA dehydrogenase (bcd), $E_7$ is an electron transfer flavoprotein subunit (etf), $E_9$ is an acetate kinase (ack), $E_{11}$ is a transhydrogenase and $E_{12}$ is a trans-2-enoyl-CoA reductase (TER) or crotonyl-CoA reductase (ccr). The cell may also comprise increased expression relative to the wild type cell of $E_{10}$, phosphotransacetylase (pta).

In particular, the activity of enzymes $E_1$ and $E_2$ may be measured using the assays taught at least in Hillmer P., 1972, Lurz R., 1979; the activity of enzyme $E_2$ may also be measured using the assay taught in Smith L. T., 1980; the activity of enzymes $E_3$ and $E_4$ may be measured using the assays taught at least in Sliwkowski M. X., 1984; the activity of $E_4$ may also be measured using the assay taught in Madan, V. K., 1972; the activity of $E_5$ may also be measured using the assay taught in Bartsch, R. G., 1961; the activity of enzymes $E_6$ and $E_7$ may be measured using the assay taught in Li, F., 2008; the activity of $E_7$ may also be measured using the assay taught in Chowdhury, 2013; the activity of $E_8$ may be measured using the assay taught in Stadman, 1953. In another example, the activity of $E_8$ may be measured using the assay taught in Barker, H. A., 1955. Methods Enzymol. 1:599-600; the activity of $E_9$ may be measured using the assay taught in Winzer, K., 1997; the activity of $E_{10}$ may be measured using the assay taught in Smith L. T., 1976; and the activity of $E_{11}$ may be measured using the assay taught in Wang S, 2010. $E_{12}$ may be measured using the assay for TER activity taught in Inui et al. (1984) Eur. J. Biochem. 142, 121-126 and/or Seubert et al. (1968) Biochim. Biophys. Acta 164, 498-517 and/or Hoffmeister, M. (2005), J. Biol. Chem., 280 (6), 4329-4338.

These methods amongst others known in the art may be used by a skilled person to confirm the increase in enzyme expression and/or activity relative to a wild type cell.

In one example, the cell according to any aspect of the present invention may be genetically modified to comprise an increased expression relative to its wild type cell of all the following enzymes $E_3$ an acetoacetyl-CoA thiolase (thl), $E_4$ a 3-hydroxybutyryl-CoA dehydrogenase (hbd), $E_5$ a 3-hydroxybutyryl-CoA dehydratase (crt), and $E_6$ a butyryl-CoA dehydrogenase (bcd) In another example, the expression of $E_7$ an electron transfer flavoprotein subunit (etf) may also be increased relative to the wild type cell. The cell according to any aspect of the present invention may thus have increased expression relative of the wild type cell of enzymes $E_3$-$E_6$ and $E_8$. In another example, the cell according to any aspect of the present invention may have increased expression relative of the wild type cell of enzymes $E_3$-$E_8$.

In another example, the cell according to any aspect of the present invention may be genetically modified to comprise an increased expression relative to its wild type cell of enzymes $E_3$, an acetoacetyl-CoA thiolase (thl), $E_4$, a 3-hydroxybutyryl-CoA dehydrogenase (hbd), $E_5$, a 3-hydroxybutyryl-CoA dehydratase (crt), $E_6$, a butyryl-CoA dehydrogenase (bcd) and $E_8$. In one example, $E_3$ may comprise the sequence of SEQ ID NO:2, $E_4$ may comprise the sequence of SEQ ID NO:3, $E_5$ may comprise the sequence of SEQ ID NO: 4, $E_6$, may comprise the sequence of SEQ ID NO: 5.

In a further example, the cell according to any aspect of the present invention may be genetically modified to comprise an increased expression relative to its wild type cell of the enzymes $E_3$, an acetoacetyl-CoA thiolase (thl), $E_4$, a 3-hydroxybutyryl-CoA dehydrogenase (hbd), $E_5$, a 3-hydroxybutyryl-CoA dehydratase (crt), and $E_8$. In one example, $E_3$ may comprise the sequence of SEQ ID NO:2, $E_4$ may comprise the sequence of SEQ ID NO:3, $E_5$ may comprise the sequence of SEQ ID NO: 4, and $E_6$, may comprise the sequence of SEQ ID NO: 5.

In another example, the cell according to any aspect of the present invention may be further genetically modified to comprise an increased expression relative to its wild type cell of the enzymes $E_1$, an alcohol dehydrogenase (adh) and the enzyme $E_{12}$, trans-2-enoyl-CoA reductase or crotonyl-CoA reductase (TER). In particular, $E_1$ may be a butyrate-dehydrogenase from C. acetobutylicum or E. coli. More in particular, the butanol-dehydrogenase from C. acetobutylicum may comprise the sequence of SEQ OD NO:18 and the butanol-dehydrogenase from E. coli may comprise the sequence of SEQ ID NO: 19. More in particular, the enzyme $E_{12}$ in the cell may be selected from the group consisting of SEQ ID NOs: 14, 15 and 16.

The cell may also comprise $E_7$ an electron transfer flavoprotein subunit (etf). More in particular, $E_7$ may be etfB and etfA from C. acetobutylicum. Even more in particular, $E_7$ may comprise the sequence of SEQ ID NOs:10 and 11.

In one example, the cell according to any aspect of the present invention may be further genetically modified to comprise an increased expression relative to its wild type cell of the enzyme $E_6$, a butyrate-dehydrogenase. In particular, $E_6$ may be from C. kluyveri and/or may comprise the sequence of SEQ ID NO:7. The cell may also comprise increased expression relative to the wild type cell of an electron-transfer protein ($E_7$). In particular, $E_7$ may comprise the sequence of SEQ ID NOs: 12 and 13. The cell may also comprise an increased expression relative to the wild type cell of trans-2-enoyl-CoA reductase (TER) ($E_{12}$). In particular, the TER may be from Treponema denticola, Euglena gracilis, or Caenorhabditis elegans. Even more in particular, $E_{12}$ may be a TER selected from the group consisting of SEQ ID NOs: 14, 15 and 16. In another example, $E_{12}$ may be crotonyl-CoA reductase (ccr). In particular, the ccr may be from Streptomyces collinus. More in particular, the enzyme $E_{12}$ may be a ccr comprising the sequence of SEQ ID NO: 17.

In one further example, the cell according to any aspect of the present invention may be further genetically modified to comprise an increased expression relative to its wild type cell of the enzyme $E_6$, a butyrate-dehydrogenase. In particular, $E_6$ may be from C. kluyveri and/or may comprise the sequence of SEQ ID NO:5. The cell may also comprise increased expression relative to the wild type cell of an electron-transfer protein ($E_7$). In particular, $E_7$ may comprise the sequence of SEQ ID NOs: 8 and 9. The cell may also comprise an increased expression relative to the wild type cell of the phosphotransacetylase (pta) promoter and/or terminator.

In particular, the cell according to any aspect of the present invention may comprise an increased expression relative to the wild type cell of the following enzymes $E_3E_8$, $E_4E_8$, $E_5E_8$, $E_6E_8$, $E_7E_8$, $E_3E_4E_8$, $E_3E_5E_8$, $E_3E_6E_8$, $E_3E_7E_8$, $E_4E_5E_8$, $E_4E_6E_8$, $E_4E_7E_8$, $E_5E_6E_8$, $E_5E_7E_8$, $E_3E_4E_5E_8$, $E_3E_4E_6E_8$, $E_3E_4E_7E_8$, $E_4E_5E_6E_8$, $E_4E_5E_7E_8$, $E_5E_6E_7E_8$, $E_3E_4E_5E_6E_8$, $E_3E_4E_5E_7E_8$, $E_4E_5E_6E_7E_8$, $E_3E_4E_5E_6E_7E_8$, $E_3E_8E_{12}$, $E_4E_8E_{12}$, $E_5E_8E_{12}$, $E_6E_8E_{12}$, $E_7E_8E_{12}$, $E_3E_4E_8E_{12}$, $E_3E_5E_8E_{12}$, $E_3E_6E_8E_{12}$, $E_3E_7E_8E_{12}$, $E_4E_5E_8E_{12}$, $E_4E_6E_8E_{12}$, $E_4E_7E_8E_{12}$, $E_5E_6E_8E_{12}$, $E_5E_7E_8E_{12}$, $E_3E_4E_5E_8E_{12}$, $E_3E_4E_6E_8E_{12}$, $E_3E_4E_7E_8E_{12}$, $E_4E_5E_6E_8E_{12}$, $E_4E_5E_7E_8E_{12}$, $E_5E_6E_7E_8E_{12}$, $E_3E_4E_5E_6E_8E_{12}$, $E_3E_4E_5E_7E_8E_{12}$, $E_4E_5E_6E_7E_8E_{12}$, $E_3E_4E_5E_6E_7E_8E_{12}$, $E_3E_8E_1$, $E_4E_8E_1$, $E_5E_8E_1$, $E_6E_8E_1$, $E_7E_8E_1$, $E_3E_4E_8E_1$, $E_3E_5E_8E_1$, $E_3E_6E_8E_1$, $E_3E_7E_8E_1$, $E_4E_5E_8E_1$, $E_4E_6E_8E_1$, $E_4E_7E_8E_1$, $E_5E_6E_8E_1$, $E_5E_7E_8E_1$, $E_3E_4E_5E_8E_1$, $E_3E_4E_6E_8E_1$, $E_3E_4E_7E_8E_1$, $E_4E_5E_6E_8E_1$, $E_4E_5E_7E_8E_1$, $E_5E_6E_7E_8E_1$, $E_3E_4E_5E_6E_8E_1$, $E_3E_4E_5E_7E_8E_1$, $E_4E_5E_6E_7E_8E_1$, $E_3E_4E_5E_6E_7E_8E_1$, $E_3E_8E_{12}E_1$, $E_4E_8E_{12}E_1$, $E_5E_8E_{12}E_1$, $E_6E_8E_{12}E_1$, $E_7E_8E_{12}E_1$, $E_3E_4E_8E_{12}E_1$, $E_3E_5E_8E_{12}E_1$, $E_3E_6E_8E_{12}E_1$, $E_3E_7E_8E_{12}E_1$, $E_4E_5E_8E_{12}E_1$, $E_4E_6E_8E_{12}E_1$, $E_4E_7E_8E_{12}E_1$, $E_5E_6E_8E_{12}E_1$, $E_5E_7E_8E_{12}E_1$, $E_3E_4E_5E_8E_{12}E_1$, $E_3E_4E_6E_8E_{12}E_1$, $E_3E_4E_7E_8E_{12}E_1$, $E_4E_5E_6E_8E_{12}E_1$, $E_4E_5E_7E_8E_{12}E_1$, $E_5E_6E_7E_8E_{12}E_1$, $E_3E_4E_5E_6E_8E_{12}E_1$, $E_3E_4E_5E_7E_8E_{12}E_1$, $E_4E_5E_6E_7E_8E_{12}E_1$, $E_3E_4E_5E_6E_7E_8E_{12}E_1$, x and the like.

In particular, $E_8$ may be selected from the group consisting of butyryl-CoA:acetate CoA transferase, succinyl-CoA:coenzyme A transferase, 4-hydroxybutyryl-CoA:coenzyme A transferase and the like. More in particular, $E_8$ may comprise sequence identity of at least 50% to a polypeptide selected from the group consisting of CKL_3595, CKL_3016, CKL_3018 and the like. More in particular, $E_8$ may comprise a polypeptide with sequence identity of at least 50, 60, 65, 70, 75, 80, 85, 90, 91, 94, 95, 98 or 100% to a polypeptide selected from the group consisting of CKL_3595, CKL_3016 and CKL_3018. $E_8$ may comprise an amino acid sequence that has 50, 55, 60, 65, 70, 75, 80, 85, 90, 95 or 100% sequence identity to SEQ ID NO: 1. In particular, $E_8$ may be from Clostridium kluyveri or Clostridium carboxidivorans. More in particular, $E_8$ may be from *Clostridium kluyveri*. Even more in particular, $E_8$ may be from *Clostridium kluyveri* strain ATCC 8527.

In particular, $E_1$ may be selected from the group consisting of alcohol dehydrogenase 1, alcohol dehydrogenase 2, alcohol dehydrogenase 3, alcohol dehydrogenase B and combinations thereof. More in particular, $E_1$ may comprise sequence identity of at least 50% to a polypeptide selected from the group consisting of CKL_1075, CKL_1077, CKL_1078, CKL_1067, CKL_2967, CKL_2978, CKL_3000, CKL_3425, and CKL_2065. Even more in particular, $E_1$ may comprise a polypeptide with sequence identity of at least 50, 60, 65, 70, 75, 80, 85, 90, 91, 94, 95, 98 or 100% to a polypeptide selected from the group consisting of CKL_1075, CKL_1077, CKL_1078 and CKL_1067. $E_1$ may comprise an amino acid sequence that has 50, 55, 60, 65, 70, 75, 80, 85, 90, 95 or 100% sequence identity to SEQ ID NO: 18 or SEQ ID NO: 19. In particular, $E_1$ may be selected from the group consisting of *C. acetobutylicum* and *E. coli*.

In particular, $E_2$ may be selected from the group consisting of acetaldehyde dehydrogenase 1, alcohol dehydrogenase 2 and combinations thereof. In particular, $E_2$ may comprise sequence identity of at least 50% to a polypeptide selected from the group consisting of CKL_1074, CKL_1076 and the like. More in particular, $E_2$ may comprise a polypeptide with sequence identity of at least 50, 60, 65, 70, 75, 80, 85, 90, 91, 94, 95, 98 or 100% to a polypeptide selected from the group consisting of CKL_1074 and CKL_1076.

$E_3$ may be selected from the group consisting of acetoacetyl-CoA thiolase A1, acetoacetyl-CoA thiolase A2, acetoacetyl-CoA thiolase A3 and combinations thereof. In particular, $E_3$ may comprise sequence identity of at least 50% to a polypeptide selected from the group consisting of CKL_3696, CKL_3697, CKL_3698 and the like. More in particular, $E_3$ may comprise a polypeptide with sequence identity of at least 50, 60, 65, 70, 75, 80, 85, 90, 91, 94, 95, 98 or 100% to a polypeptide selected from the group consisting of CKL_3696, CKL_3697 and CKL_3698. More in particular, $E_3$ may comprise an amino acid sequence that has 50, 55, 60, 65, 70, 75, 80, 85, 90, 95 or 100% sequence identity to SEQ ID NO: 2. In particular, $E_3$ may be from *C. acetobutylicum*.

$E_4$ may be 3-hydroxybutyryl-CoA dehydrogenase 1, 3-hydroxybutyryl-CoA dehydrogenase 2 and the like. In particular, $E_4$ may comprise sequence identity of at least 50% to a polypeptide CKL_0458, CKL_2795 and the like. More in particular, $E_4$ may comprise a polypeptide with sequence identity of at least 50, 60, 65, 70, 75, 80, 85, 90, 91, 94, 95, 98 or 100% to the polypeptide CKL_0458 or CKL_2795. More in particular, $E_4$ may comprise an amino acid sequence that has 50, 55, 60, 65, 70, 75, 80, 85, 90, 95 or 100% sequence identity to SEQ ID NO: 3. In particular, $E_4$ may be from *Clostridium kluyveri*.

$E_5$ may be 3-hydroxybutyryl-CoA dehydratase 1, 3-hydroxybutyryl-CoA dehydratase 2 and combinations thereof. In particular, $E_5$ may comprise sequence identity of at least 50% to a polypeptide selected from the group consisting of CKL_0454, CKL_2527 and the like. More in particular, $E_5$ may comprise a polypeptide with sequence identity of at least 50, 60, 65, 70, 75, 80, 85, 90, 91, 94, 95, 98 or 100% to a polypeptide selected from the group consisting of CKL_0454 and CKL_2527. More in particular, $E_5$ may comprise an amino acid sequence that has 50, 55, 60, 65, 70, 75, 80, 85, 90, 95 or 100% sequence identity to SEQ ID NO: 4. In particular, $E_5$ may be from *Clostridium kluyveri*.

$E_6$ may be selected from the group consisting of butyryl-CoA dehydrogenase 1, butyryl-CoA dehydrogenase 2 and the like. In particular, $E_6$ may comprise sequence identity of at least 50% to a polypeptide selected from the group consisting of CKL_0455, CKL_0633 and the like. More in particular, $E_6$ may comprise a polypeptide with sequence identity of at least 50, 60, 65, 70, 75, 80, 85, 90, 91, 94, 95, 98 or 100% to a polypeptide selected from the group consisting of CKL_0455 and CKL_0633. More in particular, $E_6$ may comprise an amino acid sequence that has 50, 55, 60, 65, 70, 75, 80, 85, 90, 95 or 100% sequence identity to SEQ ID NO: 5, SEQ ID NO:6 or SEQ ID NO: 7. In particular, $E_6$ may be selected from the group consisting of *Clostridium kluyveri*, and *C. acetobutylicum*.

$E_7$ may be selected from the group consisting of electron transfer flavoprotein alpha subunit 1, electron transfer flavoprotein alpha subunit 2, electron transfer flavoprotein beta subunit 1 and electron transfer flavoprotein beta subunit 2. In particular, $E_7$ may comprise sequence identity of at least 50% to a polypeptide selected from the group consisting of CKL_3516, CKL_3517, CKL_0456, CKL_0457 and the like. More in particular, $E_7$ may comprise a polypeptide with sequence identity of at least 50, 60, 65, 70, 75, 80, 85, 90, 91, 94, 95, 98 or 100% to a polypeptide selected from the group consisting of CKL_3516, CKL_3517, CKL_0456 and CKL_0457. More in particular, $E_7$ may comprise an amino acid sequence that has 50, 55, 60, 65, 70, 75, 80, 85, 90, 95 or 100% sequence identity to SEQ ID NO: 8, SEQ ID NO:9, SEQ ID NO:10, SEQ ID NO:11. SEQ ID NO:12 or SEQ ID NO: 13. In particular, $E_7$ may be selected from the group consisting of *Clostridium kluyveri*, and *C. acetobutylicum*.

$E_9$ may be an acetate kinase A (ack A). In particular, $E_9$ may comprise sequence identity of at least 50% to a polypeptide sequence of CKL_1391 and the like. More in particular, $E_9$ may comprise a polypeptide with sequence identity of at least 50, 60, 65, 70, 75, 80, 85, 90, 91, 94, 95, 98 or 100% to a polypeptide of CKL_1391.

$E_{10}$ may be phosphotransacetylase (pta). In particular, $E_{10}$ may comprise sequence identity of at least 50% to a polypeptide sequence of CKL_1390 and the like. More in particular, $E_{10}$ may comprise a polypeptide with sequence identity of at least 50, 60, 65, 70, 75, 80, 85, 90, 91, 94, 95, 98 or 100% to a polypeptide of CKL_1390. In particular, $E_{10}$ may be selected from *C. acetobutylicum*.

$E_{11}$ may be a tranhydrogenase. In particular, $E_{11}$ may be the transhydrogenase disclosed in Hatefi, Y., (1977) Proc. Natl. Acad. Sci. USA 74 (3). 846-850 and/or Anderlund M. (1999), Appl Environ Microbiol., 65(6): 2333-2340.

$E_{12}$ may comprise an amino acid sequence that has 50, 55, 60, 65, 70, 75, 80, 85, 90, 95 or 100% sequence identity to SEQ ID NO: 14, SEQ ID NO:15, SEQ ID NO:16 or SEQ ID NO: 17. In particular, $E_{12}$ may be selected from the group consisting of *Treponema denticola, Euglena gracilis, Caenorhabditis elegans*, and *Streptomyces collinus*.

Throughout this application, any data base code, unless specified to the contrary, refers to a sequence available from the NCBI data bases, more specifically the version online on 12 Jun. 2014, and comprises, if such sequence is a nucleotide sequence, the polypeptide sequence obtained by translating the former.

According to another aspect of the present invention there is provided a method of producing a higher alcohol, the method comprising contacting a recombinant microbial cell according to any aspect of the present invention with a medium comprising a carbon source.

The term "contacting", as used herein, means bringing about direct contact between the cell according to any aspect of the present invention and the medium comprising the carbon source.

For example, the cell, and the medium comprising the carbon source may be in different compartments. On particular, the carbon source may be in a gaseous state and added to the medium comprising the cells according to any aspect of the present invention.

The term "acetate" as used herein, refers to both acetic acid and salts thereof, which results inevitably, because as known in the art, since the microorganisms work in an aqueous environment, and there is always a balance between salt and acid present.

The term 'about' as used herein refers to a variation within 20 percent. In particular, the term "about" as used herein refers to +/−20%, more in particular, +/−10%, even more in particular, +/−5% of a given measurement or value.

All percentages (%) are, unless otherwise specified, volume percent.

The carbon source used according to any aspect of the present invention may be any carbon source known in the art. In particular, the carbon source may be selected from the group consisting of carbohydrates such as, for example, glucose, sucrose, lactose, fructose, maltose, molasses, starch and cellulose. In one example, hydrocarbons such as methane, amino acids such as L-glutamate or L-valine, or organic acids such as, for example, acetic acid may be used as a carbon source. These substances may be used singularly or as a mixture. It is especially preferred to employ carbohydrates, in particular monosaccharides, oligosaccharides or polysaccharides, as described in U.S. Pat. No. 601,494 and U.S. Pat. No. 6,136,576, or C5-sugars, or glycerol. In one example, the carbon source may comprise carbon dioxide and/or carbon monoxide. A skilled person would understand that many possible sources for the provision of CO and/or $CO_2$ as a carbon source exist. It can be seen that in practice, as the carbon source according to any aspect of the present invention any gas or any gas mixture can be used which is able to supply the microorganisms with sufficient amounts of carbon, so that acetate and/or ethanol, may be formed from the source of CO and/or $CO_2$.

Generally, for the mixed culture according to any aspect of the present invention the carbon source comprises at least 50% by volume, at least 70% by volume, particularly at least 90% by volume of CO and/or $CO_2$, wherein the percentages by volume—% relate to all carbon sources that are available to the first microorganism in the mixed culture. In one example, the carbon source may be a gas mixture comprising 5-25% by volume of CO, 25-35% by volume $CO_2$ and 50-65 $H_2$ gas. In another example, the carbon source may be a gas mixture comprising 22% by volume of CO, 6% by volume $CO_2$ and 44% $H_2$ gas. In a further example, the carbon source may be a gas mixture comprising 33% by volume $CO_2$ and 67% $H_2$ gas. In a particular example, the carbon source may be a gas mixture comprising 25% by volume of CO, 25% by volume $CO_2$ and 50% $H_2$ gas.

In the mixed culture according to any aspect of the present invention, the carbon material source may be provided. Examples of carbon sources in gas forms include exhaust gases such as synthesis gas, flue gas and petroleum refinery gases produced by yeast fermentation or clostridial fermentation. These exhaust gases are formed from the gasification of cellulose-containing materials or coal gasification. In one example, these exhaust gases may not necessarily be produced as by-products of other processes but can specifically be produced for use with the mixed culture according to any aspect of the present invention.

According to any aspect of the present invention, the carbon source may be synthesis gas. Synthesis gas can for example be produced as a by-product of coal gasification. Accordingly, the microorganism of the mixed culture according to any aspect of the present invention may be capable of converting a substance which is a waste product into a valuable resource. In another example, synthesis gas may be a by-product of gasification of widely available, low-cost agricultural raw materials for use with the mixed culture of the present invention to produce at least one higher alcohol.

There are numerous examples of raw materials that can be converted into synthesis gas, as almost all forms of vegetation can be used for this purpose. In particular, raw materials are selected from the group consisting of perennial grasses such as *miscanthus*, corn residues, processing waste such as sawdust and the like.

In general, synthesis gas may be obtained in a gasification apparatus of dried biomass, mainly through pyrolysis, partial oxidation and steam reforming, wherein the primary products of the synthesis gas are CO, $H_2$ and $CO_2$. Syngas may also be a product of electrolysis of $CO_2$. A skilled person would understand the suitable conditions to carry out electrolysis of $CO_2$ to produce syngas comprising CO in a desired amount.

Usually, a portion of the synthesis gas obtained from the gasification process is first processed in order to optimize product yields, and to avoid formation of tar. Cracking of the undesired tar and CO in the synthesis gas may be carried out using lime and/or dolomite. These processes are described in detail in for example, Reed, 1981.

Mixtures of sources can be used as a carbon source.

According to any aspect of the present invention, a reducing agent, for example hydrogen may be supplied together with the carbon source. In particular, this hydrogen may be supplied when the C and/or $CO_2$ is supplied and/or used. In one example, the hydrogen gas is part of the synthesis gas present according to any aspect of the present invention. In another example, where the hydrogen gas in the synthesis gas is insufficient for the method of the present invention, additional hydrogen gas may be supplied.

'Higher alcohols' as used herein refers to alcohols that contain 4 to 12 carbon atoms, in particular, 4 to 10 carbon atoms, 4 to 8 carbon atoms, 6 to 10 carbon atoms and may be somewhat viscous, or oily, and have heavier fruity odours. More in particular, the 'higher alcohol' may be comprise the formula I below and has 4 to 10 carbon atoms

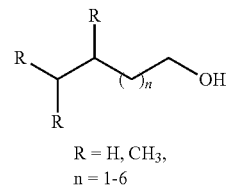

Formula I

R = H, $CH_3$,
n = 1-6

Higher alcohols may include but are not limited to hexanol, heptanol, octanol, nonanol, decanol and the like. More in particular, the higher alcohol may be selected from the group consisting of 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol and combinations thereof.

A skilled person would understand the other conditions necessary to carry out the method according to any aspect of the present invention. In particular, the conditions in the container (e.g. fermenter) may be varied depending on the first and second microorganisms used. The varying of the conditions to be suitable for the optimal functioning of the microorganisms is within the knowledge of a skilled person.

In one example, the method according to any aspect of the present invention may be carried out in an aqueous medium with a pH between 5 and 8, 5.5 and 7. The pressure may be between 1 and 10 bar.

In particular, the aqueous medium may comprise a carbon source comprising CO and/or $CO_2$. More in particular, the carbon source comprising CO and/or $CO_2$ is provided to the aqueous medium in a continuous gas flow. Even more in particular, the continuous gas flow comprises synthesis gas. In one example, the gases are part of the same flow/stream. In another example, each gas is a separate flow/stream provided to the aqueous medium. These gases may be divided for example using separate nozzles that open up into the aqueous medium, frits, membranes within the pipe supplying the gas into the aqueous medium and the like.

According to another aspect of the present invention, there is provided a use of the cell according to any aspect of the present invention for the production of a higher alcohol.

In the reaction mixture according to any aspect of the present invention, there may be oxygen present. Accordingly, the microorganisms according to any aspect of the present invention may be grown aerobically. In particular, oxygen may be provided to the aqueous medium according to any aspect of the present invention in a continuous gas flow. More in particular, the $O_2$ concentration in the gas flow may be may be present at less than 1% by volume of the total amount of gas in the gas flow. In particular, the oxygen may be present at a concentration range of 0.000005 to 2% by volume, at a range of 0.00005 to 2% by volume, 0.0005 to 2% by volume, 0.005 to 2% by volume, 0.05 to 2% by volume, 0.00005 to 1.5% by volume, 0.0005 to 1.5% by volume, 0.005 to 1.5% by volume, 0.05 to 1.5% by volume, 0.5 to 1.5% by volume, 0.00005 to 1% by volume, 0.0005 to 1% by volume, 0.005 to 1% by volume, 0.05 to 1% by volume, 0.5 to 1% by volume, 0.55 to 1% by volume, 0.60 to 1% by volume, particularly at a range of 0.60 to 1.5%, 0.65 to 1%, and 0.70 to 1% by volume. In particular, the acetogenic microorganism is particularly suitable when the proportion of 02 in the gas phase/flow is about 0.00005, 0.0005, 0.005, 0.05, 0.5, 0.6, 0.7, 0.8, 0.9, 1, 1.5, 2% by volume in relation to the volume of the gas in the gas flow. A skilled person would be able to use any one of the methods known in the art to measure the volume concentration of oxygen in the gas flow. In particular, the volume of oxygen may be measured using any method known in the art. In one example, a gas phase concentration of oxygen may be measured by a trace oxygen dipping probe from PreSens Precision Sensing GmbH. Oxygen concentration may be measured by fluorescence quenching, where the degree of quenching correlates to the partial pressure of oxygen in the gas phase. Even more in particular, the first and second microorganisms according to any aspect of the present invention are capable of working optimally in the aqueous medium when the oxygen is supplied by a gas flow with concentration of oxygen of less than 1% by volume of the total gas, in about 0.015% by volume of the total volume of gas in the gas flow supplied to the reaction mixture.

The aqueous medium according to any aspect of the present invention may comprise oxygen. The oxygen may be dissolved in the medium by any means known in the art. In particular, the oxygen may be present at 0.5 mg/L. In particular, the dissolved concentration of free oxygen in the aqueous medium may at least be 0.01 mg/L. In another example, the dissolved oxygen may be about 0.01, 0.02, 0.03, 0.04, 0.05, 0.1, 0.2, 0.3, 0.4, 0.5 mg/L. In particular, the dissolved oxygen concentration may be 0.01-0.5 mg/L, 0.01-0.4 mg/L, 0.01-0.3 mg/L, 0.01-0.1 mg/L. In particular, the oxygen may be provided to the aqueous medium in a continuous gas flow. More in particular, the aqueous medium may comprise oxygen and a carbon source comprising CO and/or $CO_2$. More in particular, the oxygen and a carbon source comprising CO and/or $CO_2$ is provided to the aqueous medium in a continuous gas flow. Even more in particular, the continuous gas flow comprises synthesis gas and oxygen. In one example, both gases are part of the same flow/stream. In another example, each gas is a separate flow/stream provided to the aqueous medium. These gases may be divided for example using separate nozzles that open up into the aqueous medium, frits, membranes within the pipe supplying the gas into the aqueous medium and the like. The oxygen may be free oxygen.

According to any aspect of the present invention, 'a reaction mixture comprising free oxygen' refers to the reaction mixture comprising elemental oxygen in the form of $O_2$. The $O_2$ may be dissolved oxygen in the reaction mixture. In particular, the dissolved oxygen may be in the concentration of >5 ppm (0.000005% vol; $5 \times 10^{-6}$). A skilled person may be capable of using any method known in the art to measure the concentration of dissolved oxygen. In one example, the dissolved oxygen may be measured by Oxygen Dipping Probes (Type PSt6 from PreSens Precision Sensing GmbH, Regensburg, Germany.

In one example according to any aspect of the present invention, the carbon source is synthesis gas and the carbon source may be blended with the oxygen gas before being supplied into the aqueous medium. This blending step may improve the efficiency and the production of higher alcohols in the reaction. The overall efficiency, alcohol productivity and/or overall carbon capture of the method of the present invention may be dependent on the stoichiometry of the $CO_2$, CO, $H_2$ and $O_2$ in the continuous gas flow. The continuous gas flows applied may be of composition $O_2$, $CO_2$ and $H_2$. In particular, in the continuous gas flow, concentration range of $O_2$ may be within 0.000005 to 1% by volume, $CO/CO_2$ about 10-50%, in particular 33% by volume and $H_2$ would be within 44% to 84%, in particular, 64 to 66.04% by volume. More in particular, the concentration of gases in the continuous gas flow may be 0.15% by volume of $O_2$, 32% by volume of $CO/CO_2$ and 64% by volume of $H_2$. In another example, the continuous gas flow can also comprise inert gases like $N_2$, up to a $N_2$ concentration of 50% by volume.

A skilled person would understand that it may be necessary to monitor the composition and flow rates of the streams at relevant intervals. Control of the composition of the stream can be achieved by varying the proportions of the constituent streams to achieve a target or desirable composition. The composition and flow rate of the blended stream can be monitored by any means known in the art. In one example, the system is adapted to continuously monitor the flow rates and compositions of at least two streams and combine them to produce a single blended substrate stream in a continuous gas flow of optimal composition, and means for passing the optimised substrate stream to the mixed culture according to any aspect of the present invention.

BRIEF DESCRIPTION OF THE FIGURES

FIG. 1 is the vector pSOS95

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

All the sequences within the examples are of the genes connected together and does not include the actual vector pSOS95 backbone sequence.

Example 1

Generation of a genetically modified acetogenic bacteria for the formation of Butanol Vectors pATh-LEM-04 and pATh-LEM-14

The genes Thiolase from *C. acetobutylicum* ATTC 824 (thl_Ca) (SEQ ID NO:28), hydroxybutyryl-CoA dehydrogenase from *C. kluyveri* (hbdl_Ck) (SEQ ID NO: 29), crotonase from *C. kluyveri* (crtl_Ck) (SEQ ID NO:30) and butyryl-CoA dehydrogenase form *C. kluyveri* (bcd1_Ck) (SEQ ID NO:31) are amplified from the corresponding genome and were inserted into the vector pEmpty by using KasI and BamHI. This plasmid (pEmpty) was based on the plasmid backbone pSOS95 (FIG. 1). To use pSOS95, it was digested with BamHI and KasI. This removed the operon ctfA-ctfB-adc, but leaves the thl promoter and the rho-independent terminator of adc. The newly generated vector, which bore the named genes, was called pATh-LEM-02 (SEQ ID NO:51 refers to the sequences of the genes connected together in pATh-LEM-02 without the sequence of the actual vector).

In a second cloning step, the vector pATh-LEM-02 was digested with EcoRI and KasI and the CoA-Transferase from *C. kluyveri* (cat3_Ck) (SEQ ID NO:26) was amplified from genomic DNA and integrated into the vector. The newly designed vector was named pATh-LEM-04. To create the vector pATh-LEM-14, the vector pATH-LEM-04 was digested with KasI and BspEI. The genes etfBA were amplified from genomic DNA of *Clostridium kluyveri* by using the oligonucleotides of SEQ ID NOs: 46 and 47.

A fragment of cat3 was amplified from pATh-LEM-04 by using the oligonucleotides of SEQ ID NOs: 48 and 49. The resultant fragment has sequence of SEQ ID NO:52. The two fragments of cat3 and etfBA were then fused using PCR with primers of SEQ ID NO: 50 and 49. This fusion insert of cat3 and etfBA was then added to the KasI and BspEI opened vector pATH-LEM-04. The resultant vector was called pATH-LEM-14 (SEQ ID NO:20 is the sequence of the target genes fused together that can be easily inserted into the vector).

Vectors pATh-Syn4-03 and pATh-LEM-23

To generate a vector named pATh-Syn4-03 a cassette with SEQ ID NO:53 was first formed. This cassette comprised the genes: Thiolase from *C. acetobutylicum* ATTC 824 (thl_Ca) (SEQ ID NO:28), hydroxybutyryl-CoA dehydrogenase from *C. kluyveri* (hbdl_Ck) (SEQ ID NO: 29), and crotonase from *C. klyuveri* (crtl_Ck) (SEQ ID NO:30). The cassette with SEQ ID NO:53 was then inserted into the vector pEmpty by using KasI and BamHI.

This plasmid (pEmpty) was based on the plasmid backbone pSOS95 (FIG. 1). To use pSOS95, it was digested with BamHI and KasI. This removes the operon ctfA-cfB-adc, but leaves the thl promoter and the rho-independent terminator of adc. In a second step, the thl promoter was removed from the vector by digesting it with SbfI and BamHI. The pta promoter fragment (SEQ ID NO: 25 (Ueki et al. (2014) mBio. 585): 1636-14) was synthesized and was ligated to the BamHI/SbfI digested vector. The newly generated vector, which bears the named genes and the pta promoter, was called pATh-Syn4-14.

The vector pATh-Syn4-14 was opened with KasI and EcoRI and ligated with SEQ ID NO:54 which was synthesized from CoA-Transferase from *C. kluyveri*. The generated vector was named pATh-LEM-23 (SEQ ID NO:21)

Vectors pATh-LEM-15, pATh-LEM-16, pATh-LEM-24, pATh-LEM-25, pATh-LEM-26

A cassette containing Thiolase from *C. acetobutylicum* ATTC 824 (thl_Ca) (SEQ ID NO:29), hydroxybutyryl-CoA dehydrogenase from *C. kluyveri* (hbdl_Ck) (SEQ ID NO: 29), and crotonase from *C. klyuveri* (crtl_Ck) (SEQ ID NO:30) were synthesized and were inserted into the vector pEmpty by using KasI and BamHI. This plasmid (pEmpty) is based on the plasmid backbone pSOS95 (FIG. 1). To use pSOS95, it was digested with BamHI and KasI. This removes the operon ctfA-ctfB-adc, but leaves the thl promoter and the rho-independent terminator of adc. The newly generated vector, which bears the named genes, was called pATh-Syn4-03.

The vector pATh-Syn4-03 was opened with KasI and a cassette containing butyrate-dehydrogenase from *C. acetobutylicum* (bcd_Ca) (SEQ ID NO:34), electron-transfer protein from *C. acetobutylicum* (etfBA_Ca) (SEQ ID NOs: 35 and 36) and CoA-transferase from *C. kluyveri* (cat3_Ck) (SEQ ID NO:26) was ligated by in vitro cloning. The newly constructed vector is named pATh-LEM-15 (SEQ ID NO:55).

The vector pATh-Syn4-03 was opened with KasI/EcoRI and ligated with a cassette (SEQ ID NO:56 without the full sequence of the vector containing butyrate-dehydrogenase from *C. kluyveri* (bcd1_Ck) (SEQ ID NO:5), electron-transfer protein from *C. kluyveri* (etfBA1_Ck) (SEQ ID NOs:8 and 9) and CoA-transferase from *C. kluyveri* (cat3_Ck) (SEQ ID NO:1). The newly constructed vector is named pATh-LEM-16.

The vector pATh-Syn4-03 was opened with KasI and EcoRI. A DNA fragment of CoA-Transferase from *C. kluyveri* (SEQ ID NO:57) was synthesized and ligated to the prepared vector. The generated vector was named pATh-LEM-24 (SEQ ID NO:22).

To generate the vector pATh-LEM-25, the plasmid pATh-Syn4-24 was opened with AsiSI and EcoRI. A DNA fragment containing the Butanol dehydrogenase B from *C. acetobutylicum* (bdhB_Ca) (SEQ ID NO:44) was synthesized and ligated to the prepared vector. The generated vector was named pATh-LEM-25 (SEQ ID NO:23).

To generate the vector pATh-LEM-26, the plasmid pATh-Syn4-25 (SEQ ID NO:23) was opened with AsiSI and AscI. The Butanol dehydrogenase from *E. coli* codon optimized for *C. ljungdahlii* (YghD_E(coCl)) (SEQ ID NO:58) was amplified, fused with a ribosome binding site and ligated to the prepared vector. The generated vector was named pATh-LEM-26 (SEQ ID NO:24).

Vectors pATh-LEM-17, pATh-LEM-18, pATh-LEM-19, pATh-LEM-20, pATh-LEM-21

The vector pATh-LEM-16 was opened with KasI and NotI. A DNA fragment of SEQ ID NO: 59 containing butyrate-dehydrogenase 2 from *C. kluyveri* (bcd2_Ck) (SEQ ID NO:37) and electron-transfer protein 2 from *C. klyuveri* (etfBA2_Ck) (SEQ ID NOs: 39 and 38) was ligated. The newly constructed vector was named pATh-LEM-17.

To create pATh-LEM-18 the vector pATh-LEM-16 was opened with KasI and NotI. The DNA fragment containing the codon optimized trans-2-enoyl-CoA reductase from *Treponema denticola* (TER_Td(coCl)) (SEQ ID NO:41) was ligated. The newly constructed vector is named pATh-LEM-18.

To create pATh-LEM-19 the vector pATh-LEM-16 was opened with Not and AarI. The DNA fragment containing the codon optimized trans-2-enoyl-CoA reductase from *Euglena gracilis* (TER_Eg(coCl)) (SEQ ID NO:40) was ligated. The newly constructed vector was named pATh-LEM-19.

The vector pATh-LEM-16 was opened with AarI and NotI. The DNA fragment containing the codon optimized trans-2-enoyl-CoA reductase from *Caenorhabditis elegans* (TER_Ce(coCl)) (SEQ ID NO:42) was ligated. The newly constructed vector was named pATh-LEM-20.

The vector pATh-LEM-16 was opened with FseI and NotI. The synthetic DNA fragment containing the codon optimized crotonyl-CoA reductase from *Streptomyces collinus* (Ccr_Sc(coCl)) (SEQ ID NO:43) was ligated. The newly constructed vector was named pATh-LEM-21.

Vector pATh-LEM-22

A DNA fragment (SEQ ID NO: 60) containing the butyryl-CoA dehydrogenase from *C. klyveri* (bcd1_Ck) (SEQ ID NO:31), electron-transfer protein from *C. kluyveri* (etfBA1_Ck) (SEQ ID NOs:32 and 33), the CoA-transferase from *C. kluyveri* (cat3_Ck) (SEQ ID NO:26) and transcriptional elements (pta-Promoter and a Terminator). The parental vector pATh-Syn4-03 was opened with EcoRI/XhoI and the DNA fragment (SEQ ID NO: 60) ligated in to produce the vector pATh-LEM-22.

Transformation of Acetogens:

The transformation of *C. ljungdahlii* DSMZ 13528 and *C. autoethanogenum* DSMZ 10061 was done as disclosed in Leang et al. (2013) Applied and Environmental Microbiology 79(4): 1102-1109.

Example 2

Fermentation of Genetically Modified Strains on Mixtures of $H_2$, $CO_2$ and CO Showing Acid and Higher Alcohol Formation.

For cell culture of
*C. ljungdahlii* pATh-LEM-04
*C. ljungdahlii* pATh-LEM-14
*C. ljungdahlii* pATh-LEM-15
*C. ljungdahlii* pATh-LEM-16
*C. ljungdahlii* pATh-LEM-17
*C. ljungdahlii* pATh-LEM-18
*C. ljungdahlii* pATh-LEM-19
*C. ljungdahlii* pATh-LEM-20
*C. ljungdahlii* pATh-LEM-21
*C. ljungdahlii* pATh-LEM-22
*C. ljungdahlii* pATh-LEM-23
*C. ljungdahlii* pATh-LEM-24
*C. ljungdahlii* pATh-LEM-25
*C. ljungdahlii* pATh-LEM-26
*C. ljungdahlii* pEmpty
*C. autoethanogenum* pATh-LEM-04
*C. autoethanogenum* pATh-LEM-14
*C. autoethanogenum* pATh-LEM-15
*C. autoethanogenum* pATh-LEM-16
*C. autoethanogenum* pATh-LEM-17
*C. autoethanogenum* pATh-LEM-18
*C. autoethanogenum* pATh-LEM-19
*C. autoethanogenum* pATh-LEM-20
*C. autoethanogenum* pATh-LEM-21
*C. autoethanogenum* pATh-LEM-22
*C. autoethanogenum* pATh-LEM-23
*C. autoethanogenum* pATh-LEM-24
*C. autoethanogenum* pATh-LEM-25
*C. autoethanogenum* pATh-LEM-26
*C. autoethanogenum* pEmpty 5 mL of the culture will be anaerobically grown in 500 ml of LM33-medium with 100 mg/L of erythromycin.

LM 33 media was prepared at pH 5.5 as follows in tables 1-3. All ingredients with the exception of cysteine HCL were mixed in $dH_2O$ to a total volume of 1 L. This solution was made anaerobic by heating to boiling point and allowing it to cool to room temperature under a constant flow of $N_2$ gas. Once cool, the cysteine HCL (0.5 g/L) was added and the pH of the solution adjusted to 5.5; anaerobicity was maintained throughout the experiments.

TABLE 1

Media component (LM-33) used in Example 1

| Media component | concentration |
| --- | --- |
| $MgCl_2 \times 6H_2O$ | 0.5 g/L |
| NaCl | 0.2 g/L |
| $CaCl_2 \times 2H_2O$ | 0.135 g/L |
| $NaH_2PO_4 \times 2H_2O$ | 2.65 g/L |
| KCl | 0.5 g/L |
| $NH_4Cl$ | 2.5 g/L |
| MES | 20.0 g/L |
| LS06-trace element solution | 10 mL/L |
| LS03-vitamin solution | 10 mL/L |
| $FeCl_3$-Solution | 2 mL/L |

TABLE 2

LS06-trace element solution

| components | concentration |
| --- | --- |
| Nitriloacetic acid | 1.5 g/L |
| $MgSO_4 \times 7H_2O$ | 3 g/L |
| $MnSO_4 \times H_2O$ | 0.5 g/L |
| NaCl | 1 g/L |
| $FeSO_4 \times 7H_2O$ | 0.1 g/L |
| $Fe(SO_4)_2(NH4)_2 \times 6H_2O$ | 0.8 g/L |
| $CoCl_2 \times 6H_2O$ | 0.2 g/L |
| $ZnSO_4 \times 7H_2O$ | 0.2 g/L |
| $CuCl_2 \times 2H_2O$ | 0.02 g/L |
| $KAl(SO_4)_2 \times 12H_2O$ | 0.02 g/L |
| $H_3BO_3$ | 0.3 g/L |
| $Na_2MoO_4 \times 2H_2O$ | 0.03 g/L |
| $Na_2SeO_3$ | 0.02 g/L |
| $NiCl_2 \times 6H_2O$ | 0.02 g/L |
| $Na_2WO_4 \times 6H_2O$ | 0.02 g/L |

TABLE 3

| component | concentration |
|---|---|
| LS03-vitamin-solution | |
| Biotin | 20 mg/L |
| Folic Acid | 20 mg/L |
| Pyridoxine HCl | 10 mg/L |
| Thiamin HCl | 50 mg/L |
| Riboflavin | 50 mg/L |
| Nicotinic Acid | 50 mg/L |
| CalciumD-(+)-pantothenate | 50 mg/L |
| Vitamin B12 | 50 mg/L |
| p-Aminobenzoic acid | 50 mg/L |
| Lipoic Acid | 50 mg/L |

Cultivation is carried out in duplicate into 1 L glass bottles with a premixed gas mixture composed of around $H_2$, $CO_2$ and CO in an open water bath shaker at 37° C., 150 rpm and aeration of 3 L/h for 70 h. The gas will enter the medium through a filter with a pore size of 10 microns, which will mount in the middle of the reactor, at a gassing tube. When sampling each 5 ml sample will be removed for determination of OD600 nm, pH and the product range. The determination of the product concentration will be performed by semi-quantitative 1 H-NMR spectroscopy. As an internal quantification standard sodium trimethylsilylpropionate will be used. In contrast to the negative controls *C. ljungdalii* pEmpty and *C. autoethanogenum* pEmpty the modified strains will produce butyrate, butanol, hexanoate, hexanol, octanoate and octanol.

Example 3

Materials and Methods

In the following examples, genetically modified *Clostridium ljungdahlii* or *Clostridium autoethanogenum* were cultivated in order to produce butanol and/or the precursors 3-hydroxybutyrate and/or butyrate. A complex medium with 5 g/L fructose was used, consisting of 1 g/L $NH_4Cl$, 0.1 g/L KCl, 0.2 g/L $MgSO_4 \times 7\ H_2O$, 0.8 g/L NaCl, 0.1 g/L $KH_2PO_4$, 20 mg/L $CaCl_2 \times 2\ H_2O$, 20 g/L MES, 1 g/L yeast extract, 0.4 g/L L-cysteine-HCl, 0.4 g/L $Na_2S \times 9\ H_2O$, 20 mg/L nitrilotriacetic acid, 10 mg/L $MnSO_4 \times H_2O$, 8 mg/L $(NH_4)_2Fe(SO_4)_2 \times 6\ H_2O$, 2 mg/L $CoCl_2 \times 6\ H_2O$, 2 mg/L $ZnSO_4 \times 7\ H_2O$, 0.2 mg/L $CuCl_2 \times 2\ H_2O$, 0.2 mg/L $Na_2MoO_4 \times 2\ H_2O$, 0.2 mg/L $NiCl_2 \times 6\ H_2O$, 0.2 mg/L $Na_2SeO_4$, 0.2 mg/L $Na_2WO_4 \times 2\ H_2O$, 20 µg/L biotin, 20 µg/L folic acid, 100 µg/L pyridoxine-HCl, 50 µg/L thiamine-HCl×$H_2O$, 50 µg/L riboflavin, 50 µg/L nicotinic acid, 50 µg/L Ca-pantothenoic acid, 1 µg/L vitamin B12, 50 µg/L p-aminobenzoic acid, 50 µg/L lipoic acid.

The heterotrophic cultivations were performed in 50 mL medium in a 250 mL serum bottle. The serum bottle was continuously shaken in an open water bath Innova 3100 from New Brunswick Scientific at 37° C. and a shaking rate of 150 $min^{-1}$.

The experiments were inoculated with 5 mL cell suspension grown in Hungate tubes in above described medium. During the experiment samples of 5 mL were taken for the determination of $OD_{600}$, pH and product concentrations. The latter were determined by quantitative $^1$H-NMR-spectroscopy.

Results and Discussion:

Example 3a

Cultivation of Genetically Modified *Clostridium ljungdahlii* pATh-LEM-14

Genetically modified *C. ljungdahlii* pATh-LEM-14 as shown in Examples 1 and 2, was heterotrophically cultivated under above described conditions.

After inoculation, cells grew up to a maximal optical density of 1.82 after 56.6 hours. Besides the natural products acetate and ethanol a maximal butanol concentration of 59 mg/L was measured after 56.6 h. Butyrate was produced up to a concentration of 200 mg/L. The results are shown in Table 4.

TABLE 4

Results of *C. ljungdahlii* pATh-LEM-14 fermentation

| | | | NMR-analytics | | | | |
|---|---|---|---|---|---|---|---|
| Process time, h | pH | $OD_{600}$ | Acetate, mg/L | Ethanol, mg/L | 3-Hydroxy-butyrate, mg/L | n-Butanol, mg/L | Butyrate, mg/L |
| 0.0 | 5.96 | 0.14 | 160 | 17 | n.d. | n.d. | 41 |
| 56.6 | 5.01 | 1.82 | 2650 | 500 | n.d. | 59 | 190 |
| 117.7 | 5.03 | 1.21 | 2700 | 490 | n.d. | 59 | 200 |

(n.d. = not detected)

Example 3b

Cultivation of Genetically Modified *Clostridium ljungdahlii* pATh-LEM-23

Genetically modified *C. ljungdahlii* pATh-LEM-23 was heterotrophically cultivated under above described conditions. After inoculation, cells grew up to a maximal optical density of 1.21 after 113.6 hours. Besides the natural products acetate and ethanol a maximal butanol concentration of 8 mg/L was measured after 113.6 h. 3-hydroxybutyrate and butyrate were produced up to concentrations of 230 mg/L and 15 mg/L respectively. The results are shown in Table 6.

TABLE 5

Results of *C. ljungdahlii* pATh-LEM-23 fermentation

| Process time, h | pH | OD$_{600}$ | Acetate, mg/L | Ethanol, mg/L | 3-Hydroxy-butyrate, mg/L | n-Butanol, mg/L | Butyrate, mg/L |
|---|---|---|---|---|---|---|---|
| 0.0 | 5.91 | 0.14 | 210 | 25 | 25 | n.d. | n.d. |
| 113.6 | 4.99 | 1.21 | 2950 | 520 | 230 | 8 | 15 |

(n.d. = not detected)

Example 3c

Cultivation of Genetically Modified *Clostridium ljungdahlii* pATh-LEM-24

Genetically modified *C. ljungdahlii* pATh-LEM-24 was heterotrophically cultivated under above described conditions. After inoculation, cells grew up to a maximal optical density of 1.92 after 113.6 hours. Besides the natural products acetate and ethanol a maximal butanol concentration of 7 mg/L was measured after 113.6 h. 3-hydroxybutyrate and butyrate were produced up to concentrations of 170 mg/L and 12 mg/L respectively. The results are shown in Table 7.

TABLE 6

Results of *C. ljungdahlii* pATh-LEM-24 fermentation

| Process time, h | pH | OD$_{600}$ | Acetate, mg/L | Ethanol, mg/L | 3-Hydroxy-butyrate, mg/L | n-Butanol, mg/L | Butyrate, mg/L |
|---|---|---|---|---|---|---|---|
| 0.0 | 5.94 | 0.06 | 91 | 15 | 17 | n.d. | n.d. |
| 113.6 | 4.95 | 1.92 | 3000 | 580 | 170 | 7 | 12 |

(n.d. = not detected)

Example 3d

Cultivation of Genetically Modified *Clostridium ljungdahlii* pATh-LEM-25

Genetically modified *C. ljungdahlii* pATh-LEM-25 was heterotrophically cultivated under above described conditions. After inoculation, cells grew up to a maximal optical density of 1.52 after 117.4 hours. Besides the natural products acetate and ethanol no butanol was detected. Butyrate had a peak of 13 mg/L after 51.1 hours, but was consumed again thereafter. The precursor 3-hydroxybutyrate was produced up to a concentration of 73 mg/L. The results are shown in Table 8.

TABLE 7

Results of *C. ljungdahlii* pATh-LEM-25 fermentation

| Process time, h | pH | OD$_{600}$ | Acetate, mg/L | Ethanol, mg/L | 3-Hydroxy-butyrate, mg/L | n-Butanol, mg/L | Butyrate, mg/L |
|---|---|---|---|---|---|---|---|
| 0.0 | 6.01 | 0.07 | 88 | 19 | 17 | n.d. | n.d. |
| 51.1 | 5.82 | 0.61 | 730 | 320 | 55 | n.d. | 13 |
| 117.4 | 5.04 | 1.52 | 2800 | 640 | 73 | n.d. | n.d. |

(n.d. = not detected)

Example 3e

Cultivation of Genetically Modified *Clostridium autoethanogenum* pATh-LEM-23

In this example, genetically modified *C. autoethanogenum* pATh-LEM-23 was heterotrophically cultivated under above described conditions.

After inoculation, cells grew to a maximal optical density of 0.98 after 117.4 hours. Besides the natural products acetate and ethanol no butanol was detected. The precursor butyrate had a peak of 6 mg/L after 51.1 hours, but was consumed again thereafter. The precursor 3-hydroxybutyrate was produced up to a concentration of 140 mg/L. The results are shown in Table 9.

TABLE 8

Results of *C. autoethanogenum* pATh-LEM-23 fermentation

| Process time, h | pH | $OD_{600}$ | Acetate, mg/L | Ethanol, mg/L | 3-Hydroxy-butyrate, mg/L | n-Butanol, mg/L | Butyrate, mg/L |
|---|---|---|---|---|---|---|---|
| 0.0 | 5.98 | 0.08 | 120 | 31 | 12 | n.d. | n.d. |
| 51.1 | 5.93 | 0.27 | 350 | 180 | 16 | n.d. | 6 |
| 117.4 | 5.26 | 0.98 | 2200 | 760 | 140 | n.d. | n.d. |

(n.d. = not detected)

Example 3f

Cultivation of Wildtype *Clostridium ljungdahlii* DSM 13528 (Wildtype)

The wildtype of *C. ljungdahlii* (DSM 13528) was heterotrophically cultivated under above described conditions. After inoculation, cells began to grow up to a maximal optical density of 1.20 after 68.5 hours. Only the natural products acetate and ethanol were measured after 68.5 h to maximal concentrations of 1197 mg/L and ethanol respectively.

TABLE 9

Results of *C. ljungdahlii* wt fermentation

| Process time, h | pH | $OD_{600}$ | Acetate, mg/L | Ethanol, mg/L | 3-Hydroxy-butyrate, mg/L | n-Butanol, mg/L | Butyrate, mg/L |
|---|---|---|---|---|---|---|---|
| 0.0 | 6.00 | 0.11 | 156 | 15 | n.d. | n.d. | n.d. |
| 68.5 | 5.61 | 1.20 | 1197 | 402 | n.d. | n.d. | n.d. |

(n.d. = not detected)

The invention claimed is:

1. An acetogenic microbial cell which is capable of producing at least one higher alcohol from a carbon source, wherein the acetogenic microbial cell is genetically modified to comprise at least one enzyme, $E_8$, a butyryl-CoA: acetate CoA transferase (cat3), wherein said $E_8$ comprises an amino acid sequence having at least 100% sequence identity with the amino acid sequence of SEQ ID NO:1 of an enzyme obtained from *Clostridium kluyveri*, and wherein the higher alcohol comprises the structure of formula I below and has 4 to 10 carbon atoms:

Formula I

R—CH(R)—CH(R)—(CH$_2$)$_n$—OH

R = H, CH$_3$
n = 1-6 wherein the acetogenic microbial cell is *Clostridium ljungdahlii* or *Clostridium autothenogenum*.

2. The acetogenic microbial cell of claim 1, wherein the cell is genetically modified to comprise an increased expression relative to its wild type cell of at least one further enzyme selected from the group consisting of $E_1$, $E_3$ to $E_7$ and $E_{12}$, wherein $E_1$ is an alcohol dehydrogenase (adh) comprising at least a 90% sequence identity with SEQ ID NO: 18 or SEQ ID NO: 19 and comprises alcohol dehydrogenase activity, $E_3$ is an acetoacetyl-CoA thiolase (thl) comprising at least a 90% sequence identity with SEQ ID NO: 2 and comprises acetoacetyl-CoA thiolase activity, $E_4$ is a 3-hydroxybutyryl-CoA dehydrogenase (hbd) comprising at least a 90% sequence identity with SEQ ID NO: 3 and comprises 3-hydroxybutyryl-CoA dehydrogenase activity, $E_5$ is a 3-hydroxybutyryl-CoA dehydratase (crt) comprising at least a 90% sequence identity with SEQ ID NO: 4 and comprises 3-hydroxybutyryl-CoA dehydratase activity, $E_6$ is a butyryl-CoA dehydrogenase (bcd) comprising at least a 90% sequence identity with an amino acid sequence selected from the group consisting of SEQ ID NOs: 5-7 and comprises butyryl-CoA dehydrogenase activity, $E_7$ is an electron transfer flavoprotein subunit (etf) comprising at least a 90% sequence identity with an amino acid sequence selected from the group consisting of SEQ ID NOs: 8-13 and comprises electron transfer flavoprotein subunit activity, and $E_{12}$ is a trans-2-enoyl-CoA reductase or crotonyl-CoA reductase comprising at least a 90% sequence identity with an amino acid sequence selected from the group consisting of SEQ ID NOs: 15-17 and comprises trans-2-enoyl-CoA reductase or crotonyl-CoA reductase activity.

3. The acetogenic microbial cell of claim 1, wherein the increased expression of the $E_8$ increases due to an increase in the copy number of a gene for $E_8$.

4. The acetogenic microbial cell of claim 2, wherein:
$E_1$ comprises at least a 95% sequence identity with SEQ ID NO: 18 or SEQ ID NO: 19 and comprises alcohol dehydrogenase activity;
$E_3$ comprises at least a 95% sequence identity with SEQ ID NO: 2 and comprises acetoacetyl-CoA thiolase activity;
$E_4$ comprises at least a 95% sequence identity with SEQ ID NO: 3 and comprises 3-hydroxybutyryl-CoA dehydrogenase activity;
$E_5$ comprises at least a 95% sequence identity with SEQ ID NO: 4 and comprises 3-hydroxybutyryl-CoA dehydratase activity;
$E_6$ comprises at least a 95% sequence identity with at least one amino acid sequence selected from the group consisting of SEQ ID NOs: 5-7 and comprises butyryl-CoA dehydrogenase activity;
$E_7$ comprises at least a 95% sequence identity with an amino acid sequence selected from the group consisting of SEQ ID NOs: 8-13 and comprises electron transfer flavoprotein subunit activity;
$E_{12}$ comprises at least a 95% sequence identity with an amino acid sequence selected from the group consisting of SEQ ID NO: 15-17 and comprises trans-2-enoyl-CoA reductase or crotonyl-CoA reductase activity.

5. The acetogenic microbial cell of claim 1, wherein the higher alcohol is selected from the group consisting of 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol and combinations thereof.

6. A method of producing at least one higher alcohol, the method comprising
contacting the acetogenic microbial cell of claim 1 with a medium comprising a carbon source.

7. The method of claim 6, wherein the carbon source comprises CO and/or $CO_2$.

8. The method of claim 6, wherein the microbial cell is genetically modified to comprise an increased expression relative to its wild type cell of at least one further enzyme selected from the group consisting of $E_1$, $E_3$ to $E_7$ and $E_{12}$, wherein $E_1$ is an alcohol dehydrogenase (adh) comprising at least a 90% sequence identity with SEQ ID NO: 18 or SEQ ID NO: 19, $E_3$ is an acetoacetyl-CoA thiolase (thl) comprising at least a 90% sequence identity with SEQ ID NO: 2, $E_4$ is a 3-hydroxybutyryl-CoA dehydrogenase (hbd) comprising at least a 90% sequence identity with SEQ ID NO: 3, $E_5$ is a 3-hydroxybutyryl-CoA dehydratase (crt) comprising at least a 90% sequence identity with SEQ ID NO: 4, $E_6$ is a butyryl-CoA dehydrogenase (bcd) comprising at least a 90% sequence identity with an amino acid sequence selected from the group consisting of SEQ ID NOs: 5-7, $E_7$ is an electron transfer flavoprotein subunit (etf) comprising at least a 90% sequence identity with an amino acid sequence selected from the group consisting of SEQ ID NOs: 8-13, and $E_{12}$ is a trans-2-enoyl-CoA reductase or crotonyl-CoA reductase comprising at least a 90% sequence identity with an amino acid sequence selected from the group consisting of SEQ ID NOs: 15-17.

9. The method of claim 8, wherein the acetogenic microbial cell is genetically modified to comprise an increased expression relative to its wild type cell of $E_3$, $E_4$ and $E_{12}$.

10. The method of claim 6, wherein the higher alcohol is selected from the group consisting of 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol and combinations thereof.

11. The method of claim 6, wherein increased expression of $E_8$ is due to expression of a heterologous $E_8$ enzyme, an increase in the copy number of a gene for $E_8$, the use of a heterologous promoter, or combinations thereof.

12. An acetogenic microbial cell which is capable of producing at least one higher alcohol from a carbon source, wherein:
the acetogenic microbial cell is genetically modified to comprise increased butyryl-CoA: acetate CoA transferase (cat3 activity) relative to the acetogenic microbial cell before being genetically modified, said increased activity being at least partially due to the enzyme $E_8$, wherein said $E_8$ comprises an amino acid sequence having at least 100% sequence identity with the amino acid sequence of SEQ ID NO: 1 of an enzyme of obtained from *Clostridium kluyveri*;
the higher alcohol comprises the structure of formula I below and has 4 to 10 carbon atoms:

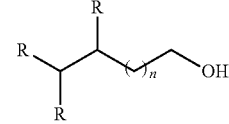

Formula I wherein R = H or $CH_3$, and n = 1-6;

wherein R=H or $CH_3$, and n=1-6;
and wherein the acetogenic microbial cell is *Clostridium ljungdahlii* or *Clostridium* autothenogenum.

13. The acetogenic microbial cell of claim 12, wherein the cell is genetically modified to comprise increased expression relative to its wild type cell of at least one enzyme selected from the group consisting of $E_1$, $E_3$ to $E_7$ and $E_{12}$, wherein $E_1$ is an alcohol dehydrogenase (adh) comprising at least a 90% sequence identity with SEQ ID NO: 18 or SEQ ID NO: 19 and comprises alcohol dehydrogenase activity, $E_3$ is an acetoacetyl-CoA thiolase (thl) comprising at least a 90% sequence identity with SEQ ID NO: 2 and comprises acetoacetyl-CoA thiolase activity, $E_4$ is a 3-hydroxybutyryl-CoA dehydrogenase (hbd) comprising at least a 90% sequence identity with SEQ ID NO: 3 and comprises 3-hydroxybutyryl-CoA dehydrogenase activity, $E_5$ is a 3-hydroxybutyryl-CoA dehydratase (crt) comprising at least a 90% sequence identity with SEQ ID NO: 4 and comprises 3-hydroxybutyryl-CoA dehydratase activity, $E_6$ is a butyryl-CoA dehydrogenase (bcd) comprising at least a 90% sequence identity with an amino acid sequence selected from the group consisting of SEQ ID NOs: 5-7 and comprises butyryl-CoA dehydrogenase activity, $E_7$ is an electron transfer flavoprotein subunit (etf) comprising at least a 90% sequence identity with an amino acid sequence selected from the group consisting of SEQ ID NOs: 8-13 and comprises electron transfer flavoprotein subunit activity, and $E_{12}$ is a trans-2-enoyl-CoA reductase or crotonyl-CoA reductase comprising at least a 90% sequence identity with an amino acid sequence selected from the group consisting of SEQ ID NOs: 15-17 and comprises trans-2-enoyl-CoA reductase or crotonyl-CoA reductase activity.

14. The acetogenic microbial cell of claim 13, wherein:
- $E_1$ comprises at least a 95% sequence identity with SEQ ID NO: 18 or SEQ ID NO: 19 and comprises alcohol dehydrogenase activity;
- $E_3$ comprises at least a 95% sequence identity with SEQ ID NO: 2 and comprises acetoacetyl-CoA thiolase activity;
- $E_4$ comprises at least a 95% sequence identity with SEQ ID NO: 3 and comprises 3-hydroxybutyryl-CoA dehydrogenase activity;
- $E_5$ comprises at least a 95% sequence identity with SEQ ID NO: 4 and comprises 3-hydroxybutyryl-CoA dehydratase activity;
- $E_6$ comprises at least a 95% sequence identity with at least one amino acid sequence selected from the group consisting of SEQ ID NOs: 5-7 and comprises butyryl-CoA dehydrogenase activity;
- $E_7$ comprises at least a 95% sequence identity with an amino acid sequence selected from the group consisting of SEQ ID NOs: 8-13 and comprises electron transfer flavoprotein subunit activity;
- $E_{12}$ comprises at least a 95% sequence identity with an amino acid sequence selected from the group consisting of SEQ ID NO: 15-17 and comprises trans-2-enoyl-CoA reductase or crotonyl-CoA reductase activity.

15. The acetogenic microbial cell of claim 14, wherein the higher alcohol is selected from the group consisting of 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol and combinations thereof.

16. The acetogenic microbial cell of claim 12, wherein the higher alcohol is selected from the group consisting of 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol and combinations thereof.

* * * * *